(12) United States Patent
Ingimundarson et al.

(10) Patent No.: US 11,259,948 B2
(45) Date of Patent: *Mar. 1, 2022

(54) ORTHOPEDIC DEVICE FOR TREATING COMPLICATIONS OF THE HIP

(71) Applicant: OSSUR HF, Reykjavik (IS)

(72) Inventors: Arni Thor Ingimundarson, Reykjavik (IS); Thorvaldur Ingvarsson, Reykjavik (IS); Nina Bakken, Reykjavik (IS); Valgeir Petursson, Reykjavik (IS); Helga Run Palsdottir, Reykjavik (IS); Thorleifur Stefansson, Reykjavik (IS); Hronn Kristinsdottir, Reykjavik (IS); Stefan Orn Stefansson, Reykjavik (IS); Henry Hsu, Foothill Ranch, CA (US)

(73) Assignee: OSSUR HF, Reykjavik (IS)

( * ) Notice: Subject to any disclaimer, the term of this patent is extended or adjusted under 35 U.S.C. 154(b) by 996 days.

This patent is subject to a terminal disclaimer.

(21) Appl. No.: 15/784,759

(22) Filed: Oct. 16, 2017

(65) Prior Publication Data

US 2018/0049904 A1 Feb. 22, 2018

Related U.S. Application Data

(63) Continuation of application No. 14/809,823, filed on Jul. 27, 2015, now Pat. No. 9,795,500, which is a
(Continued)

(51) Int. Cl.
*A61F 5/01* (2006.01)

(52) U.S. Cl.
CPC .......... *A61F 5/0193* (2013.01); *A61F 5/0102* (2013.01)

(58) Field of Classification Search
CPC .......... A61F 5/022; A61F 5/024; A61F 5/026; A61F 5/028; A61F 5/03;
(Continued)

(56) References Cited

U.S. PATENT DOCUMENTS

| 7,916 | A | 1/1851 | Knapp |
|---|---|---|---|
| 61,487 | A | 1/1867 | Vollschwitz |

(Continued)

FOREIGN PATENT DOCUMENTS

| AU | 20 1027 10 20 A1 | 2/2012 |
|---|---|---|
| AU | 20 1027 10 20 A2 | 2/2012 |

(Continued)

OTHER PUBLICATIONS

Pamphlet—"Bledsoe Phillippon K.A.F. Positioning Kit, Application Instructions (CP020205 Rev B Apr. 2007), New Hip Arthroscopy Padding and Positioning Kit", Council Directive 93/42/EEC of Jun. 14, 1993 concerning Medical Devices, 2 pages.
(Continued)

*Primary Examiner* — Michelle J Lee
(74) *Attorney, Agent, or Firm* — Workman Nydegger

(57) ABSTRACT

An orthopedic device is provided for treating complications of the hip and has means for trochanter compression, pelvis support, lumbar compression, variously directed straps, and thigh support. The trochanter compression and an internal/external rotation strap provide pain relief through compression and skin protection, unloading of joints through compression and sealing, and unloading by load transfer. Means for adjustably dosing of straps enables pain management and ease of use.

8 Claims, 33 Drawing Sheets

Related U.S. Application Data continuation-in-part of application No. 14/162,958, filed on Jan. 24, 2014, now Pat. No. 9,393,144.

(60) Provisional application No. 61/894,953, filed on Oct. 24, 2013, provisional application No. 61/756,220, filed on Jan. 24, 2013, provisional application No. 61/756,438, filed on Jan. 24, 2013.

(58) Field of Classification Search
CPC ............ A61F 5/01–0109; A61F 5/0123; A61F 5/0193; A61F 5/02–03; A61F 5/3715; A61F 5/0102–0109; A63B 21/065; A63B 21/068; A63B 21/4011; A63B 21/4023; A63B 21/4025; A41D 13/05; A41D 13/0506; A41D 13/0525; A41D 13/0537–0587
USPC .......................................................... 602/19
See application file for complete search history.

(56) References Cited

U.S. PATENT DOCUMENTS

| | | | |
|---|---|---|---|
| 181,948 A | 9/1876 | Kleinschuster | |
| 232,420 A | 9/1880 | Smith | |
| 321,145 A | 6/1885 | Spencer | |
| 321,146 A | 6/1885 | Spencer | |
| 328,638 A | 10/1885 | Battershall | |
| 368,699 A | 8/1887 | Zervas | |
| 386,642 A | 7/1888 | Mann | |
| 507,172 A | 10/1893 | Shelden | |
| 571,749 A | 11/1896 | Colton | |
| 596,849 A | 1/1898 | Combier | |
| 601,446 A | 3/1898 | Mestler | |
| 616,196 A | 12/1898 | Medbury | |
| 629,900 A | 8/1899 | Fosburgh | |
| 639,072 A | 12/1899 | Lyons | |
| 664,250 A | 12/1900 | Fitzpatrick | |
| 709,055 A | 9/1902 | Sheldon | |
| 714,124 A | 11/1902 | Adams | |
| 746,563 A | 12/1903 | McMahon | |
| 772,926 A | 10/1904 | Colton | |
| 787,894 A | 4/1905 | Colton | |
| 888,490 A | 5/1908 | Haas | |
| 894,066 A | 7/1908 | Scapra | |
| 980,457 A | 1/1911 | Toles | |
| 1,124,596 A | 1/1915 | Dalpe | |
| 1,316,915 A | 9/1919 | Meyer et al. | |
| 1,393,188 A | 10/1921 | Whiteman | |
| 1,463,579 A | 7/1923 | Funck | |
| 1,469,661 A | 10/1923 | Migita | |
| 1,481,903 A | 1/1924 | Hart | |
| 1,530,713 A | 3/1925 | Clark | |
| 1,558,661 A | 10/1925 | Yeganian | |
| 1,607,032 A | 11/1926 | Whitley | |
| 1,727,668 A * | 9/1929 | Parkison | A61F 5/03 128/96.1 |
| 1,755,641 A | 4/1930 | Foulke | |
| 1,948,785 A | 2/1934 | Dondelinger | |
| 1,981,157 A | 11/1934 | Walter | |
| 2,036,484 A | 4/1936 | Le May | |
| 2,100,964 A | 11/1937 | Kendrick | |
| 2,117,309 A | 5/1938 | Fritsch | |
| 2,219,475 A | 10/1940 | Flaherty | |
| 2,332,119 A * | 10/1943 | Springer | A61F 5/0193 602/19 |
| 2,409,381 A | 10/1946 | Pease, Jr. | |
| 2,543,370 A | 2/1951 | Kludt et al. | |
| 2,554,337 A | 5/1951 | Lampert | |
| 2,630,801 A | 3/1953 | Mest et al. | |
| 2,696,011 A | 12/1954 | Galdik | |
| 2,749,550 A | 6/1956 | Pease | |
| 2,775,767 A | 1/1957 | Gould | |
| 2,793,368 A | 5/1957 | Nouel | |
| 2,808,050 A | 10/1957 | Ward | |
| 2,815,021 A | 12/1957 | Freeman | |
| 2,828,737 A | 4/1958 | Hale | |
| 2,904,040 A | 9/1959 | Hale | |
| 2,906,260 A | 9/1959 | Myers | |
| 2,906,261 A | 9/1959 | Craig | |
| 3,095,875 A | 7/1963 | Davidson et al. | |
| 3,096,760 A | 7/1963 | Nelkin | |
| 3,128,514 A | 4/1964 | Parker et al. | |
| 3,274,996 A | 9/1966 | Jewett | |
| 3,282,264 A | 11/1966 | Connelly | |
| 3,351,053 A | 11/1967 | Stuttle | |
| 3,371,351 A | 3/1968 | Allain | |
| 3,434,469 A | 3/1969 | Swift | |
| 3,441,027 A * | 4/1969 | Lehman | A61F 5/03 450/154 |
| 3,480,012 A | 11/1969 | Smithers et al. | |
| 3,509,875 A | 5/1970 | Richter | |
| 3,548,817 A | 12/1970 | Mittasch | |
| 3,563,431 A | 2/1971 | Pletz | |
| 3,570,480 A | 3/1971 | Stubbs | |
| 3,578,773 A | 5/1971 | Schultz | |
| 3,600,717 A | 8/1971 | McKeehan | |
| 3,601,819 A | 8/1971 | Herrmann | |
| 3,603,316 A | 9/1971 | Lehman | |
| 3,762,421 A | 10/1973 | Sax, Sr. | |
| 3,771,513 A | 11/1973 | Velazquez | |
| 3,793,749 A | 2/1974 | Gertsch et al. | |
| 3,808,644 A | 5/1974 | Schoch | |
| 3,812,850 A | 5/1974 | Reiman | |
| 3,816,211 A | 6/1974 | Haigh | |
| 3,834,048 A | 9/1974 | Maurer | |
| 3,889,664 A | 6/1975 | Heuser et al. | |
| 3,902,503 A | 9/1975 | Gaylord, Jr. | |
| 3,920,008 A | 11/1975 | Lehman | |
| 3,926,182 A | 12/1975 | Stabholz | |
| 3,927,665 A | 12/1975 | Wax | |
| 3,945,376 A | 3/1976 | Kuehnegger | |
| 4,042,433 A | 8/1977 | Hardy et al. | |
| 4,055,168 A | 10/1977 | Miller et al. | |
| 4,071,387 A | 1/1978 | Schlaepfer | |
| 4,099,524 A | 7/1978 | Cueman et al. | |
| 4,114,788 A | 9/1978 | Zufich | |
| 4,162,672 A | 7/1979 | Yazaki | |
| 4,173,973 A | 11/1979 | Hendricks | |
| 4,175,553 A | 11/1979 | Rosenberg | |
| 4,182,338 A | 1/1980 | Stanulis | |
| 4,230,101 A | 10/1980 | Gold | |
| 4,261,081 A | 4/1981 | Lott | |
| 4,285,336 A | 8/1981 | Oebser et al. | |
| 4,308,861 A | 1/1982 | Kelly | |
| 4,322,092 A | 3/1982 | Feucht et al. | |
| 4,383,523 A | 5/1983 | Schurman | |
| 4,392,489 A | 7/1983 | Wagner, Sr. | |
| 4,433,456 A | 2/1984 | Baggio | |
| RE31,564 E | 4/1984 | Hendricks | |
| 4,475,543 A | 10/1984 | Brooks et al. | |
| 4,479,495 A | 10/1984 | Isaacson | |
| 4,494,536 A | 1/1985 | Latenser | |
| 4,502,471 A | 3/1985 | Owens | |
| 4,508,110 A | 4/1985 | Modglin | |
| 4,531,515 A | 7/1985 | Rolfes | |
| 4,555,830 A | 12/1985 | Petrini et al. | |
| 4,559,933 A | 12/1985 | Batard et al. | |
| 4,569,336 A | 2/1986 | Wheeler | |
| 4,574,500 A | 3/1986 | Aldinio et al. | |
| 4,574,789 A | 3/1986 | Forster | |
| 4,574,790 A | 3/1986 | Wellershaus | |
| 4,590,939 A | 5/1986 | Sakowski | |
| 4,608,971 A | 9/1986 | Borschneck | |
| 4,616,524 A | 10/1986 | Bidoia | |
| 4,619,657 A | 10/1986 | Keates et al. | |
| 4,628,913 A | 12/1986 | Lerman | |
| 4,631,839 A | 12/1986 | Bonetti et al. | |
| 4,631,840 A | 12/1986 | Gamm | |
| 4,635,626 A | 1/1987 | Lerman | |
| 4,640,269 A | 2/1987 | Goins | |
| 4,648,390 A | 3/1987 | Friddle | |
| 4,649,574 A | 3/1987 | Michels | |
| 4,654,985 A | 4/1987 | Chalmers | |

(56) References Cited

U.S. PATENT DOCUMENTS

| | | | |
|---|---|---|---|
| 4,655,201 A | 4/1987 | Pirmantgen | |
| 4,658,807 A | 4/1987 | Swain | |
| 4,660,302 A | 4/1987 | Arieh et al. | |
| 4,677,699 A | 7/1987 | Barabe | |
| 4,677,969 A | 7/1987 | Calabrese | |
| 4,680,878 A | 7/1987 | Pozzobon et al. | |
| 4,691,696 A | 9/1987 | Farfan De Los Godos | |
| 4,696,291 A | 9/1987 | Tyo | |
| 4,697,583 A | 10/1987 | Mason et al. | |
| 4,697,592 A | 10/1987 | Maddux et al. | |
| 4,716,898 A | 1/1988 | Chauve et al. | |
| 4,719,670 A | 1/1988 | Kurt | |
| 4,719,709 A | 1/1988 | Vaccari | |
| 4,761,834 A * | 8/1988 | Kolb | A41D 13/0506 2/267 |
| 4,796,610 A | 1/1989 | Cromartie | |
| 4,799,297 A | 1/1989 | Baggio et al. | |
| 4,802,291 A | 2/1989 | Sartor | |
| 4,805,605 A | 2/1989 | Glassman | |
| 4,807,605 A | 2/1989 | Mattingly | |
| 4,811,503 A | 3/1989 | Iwama | |
| 4,843,688 A | 7/1989 | Ikeda | |
| 4,854,308 A * | 8/1989 | Drillio | A61F 5/0123 602/16 |
| 4,862,878 A | 9/1989 | Davison et al. | |
| 4,870,761 A | 10/1989 | Tracy | |
| 4,905,678 A | 3/1990 | Cumins et al. | |
| 4,923,474 A | 5/1990 | Klasson et al. | |
| 4,937,952 A | 7/1990 | Olivieri | |
| 4,961,544 A | 10/1990 | Bidoia | |
| 4,963,208 A | 10/1990 | Muncy et al. | |
| 4,976,257 A | 12/1990 | Akin et al. | |
| 4,986,263 A | 1/1991 | Dickerson et al. | |
| 4,997,438 A | 3/1991 | Nipper | |
| 5,027,482 A | 7/1991 | Torppey | |
| 5,072,725 A | 12/1991 | Miller | |
| 5,074,288 A | 12/1991 | Miller | |
| 5,092,321 A | 3/1992 | Spademan | |
| 5,098,770 A | 3/1992 | Paire | |
| 5,105,828 A | 4/1992 | Grant | |
| 5,111,807 A | 5/1992 | Spahn et al. | |
| 5,117,567 A | 6/1992 | Berger | |
| 5,120,288 A | 6/1992 | Sinaki | |
| 5,121,741 A | 6/1992 | Bremer et al. | |
| 5,127,897 A | 7/1992 | Roller | |
| 5,135,470 A | 8/1992 | Reeves | |
| 5,135,471 A | 8/1992 | Houswerth | |
| 5,154,690 A | 10/1992 | Shiono | |
| 5,157,813 A | 10/1992 | Carroll | |
| 5,170,505 A | 12/1992 | Rohrer | |
| 5,171,296 A | 12/1992 | Herman | |
| 5,176,131 A | 1/1993 | Votel et al. | |
| 5,177,882 A | 1/1993 | Berger | |
| 5,181,331 A | 1/1993 | Berger | |
| 5,183,036 A | 2/1993 | Spademan | |
| D334,063 S | 3/1993 | Dewall | |
| 5,199,940 A | 4/1993 | Morris et al. | |
| 5,201,074 A | 4/1993 | Dicker | |
| 5,203,765 A | 4/1993 | Friddle, Jr. | |
| 5,215,518 A | 6/1993 | Rosen | |
| 5,226,874 A | 7/1993 | Heinz et al. | |
| 5,230,698 A | 7/1993 | Garth | |
| 5,259,831 A | 11/1993 | Lebron | |
| 5,259,833 A | 11/1993 | Barnett | |
| 5,267,928 A * | 12/1993 | Barile | A63B 21/4025 2/228 |
| 5,286,251 A * | 2/1994 | Thompson | A61F 5/3715 128/100.1 |
| 5,295,947 A | 3/1994 | Muncy | |
| 5,295,996 A | 3/1994 | Blair | |
| 5,307,521 A | 5/1994 | Davis | |
| 5,313,952 A | 5/1994 | Hoch | |
| 5,318,575 A | 6/1994 | Chesterfield et al. | |
| 5,327,662 A | 7/1994 | Hallenbeck | |
| 5,334,135 A | 8/1994 | Grim et al. | |
| 5,342,289 A | 8/1994 | Munny | |
| 5,346,461 A | 9/1994 | Heinz et al. | |
| 5,363,863 A | 11/1994 | Lelli et al. | |
| 5,365,947 A | 11/1994 | Bonutti | |
| 5,368,552 A | 11/1994 | Williamson et al. | |
| 5,376,129 A | 12/1994 | Faulkner et al. | |
| 5,383,893 A | 1/1995 | Daneshvar | |
| 5,387,245 A | 2/1995 | Fay et al. | |
| 5,399,151 A | 3/1995 | Smith | |
| 5,421,809 A | 6/1995 | Rise | |
| 5,423,852 A | 6/1995 | Daneshvar | |
| 5,429,587 A | 7/1995 | Gates | |
| 5,433,648 A | 7/1995 | Frydman | |
| 5,433,697 A | 7/1995 | Cox | |
| 5,435,015 A | 7/1995 | Ellis-Brewer | |
| 5,437,614 A | 8/1995 | Grim | |
| 5,437,617 A | 8/1995 | Heinz et al. | |
| 5,437,619 A | 8/1995 | Malewicz et al. | |
| 5,449,338 A | 9/1995 | Trudell | |
| 5,450,858 A | 9/1995 | Zablotsky et al. | |
| 5,465,428 A * | 11/1995 | Earl | A63B 21/0552 2/227 |
| 5,466,214 A | 11/1995 | Calderon-Garciduenas | |
| 5,484,395 A | 1/1996 | Deroche | |
| 5,499,965 A | 3/1996 | Sanchez | |
| 5,500,959 A | 3/1996 | Yewer, Jr. | |
| 5,502,902 A | 4/1996 | Sussmann | |
| 5,503,314 A | 4/1996 | Fiscus | |
| 5,503,620 A | 4/1996 | Danzger | |
| 5,507,681 A | 4/1996 | Smith et al. | |
| 5,507,834 A | 4/1996 | Laghi | |
| 5,520,619 A | 5/1996 | Martin | |
| 5,522,792 A | 6/1996 | Bassett et al. | |
| 5,531,669 A | 7/1996 | Varnau | |
| 5,536,246 A | 7/1996 | Saunders | |
| 5,539,020 A | 7/1996 | Bracken et al. | |
| 5,548,843 A | 8/1996 | Chase et al. | |
| 5,551,950 A | 9/1996 | Oppen | |
| 5,556,374 A | 9/1996 | Grace et al. | |
| 5,558,628 A | 9/1996 | Bzoch | |
| 5,569,171 A | 10/1996 | Muncy | |
| 5,571,355 A | 11/1996 | Kornylo | |
| 5,599,287 A | 2/1997 | Beczak, Sr. et al. | |
| 5,599,288 A | 2/1997 | Shirley et al. | |
| 5,603,122 A | 2/1997 | Kania | |
| 5,620,412 A | 4/1997 | Modglin | |
| 5,622,529 A | 4/1997 | Calabrese | |
| 5,632,724 A | 5/1997 | Lerman et al. | |
| 5,634,891 A | 6/1997 | Beczak, Sr. et al. | |
| 5,638,588 A | 6/1997 | Jungkind | |
| 5,669,116 A | 9/1997 | Jungkind | |
| 5,674,187 A | 10/1997 | Zepf | |
| 5,681,270 A | 10/1997 | Klearman et al. | |
| 5,685,830 A | 11/1997 | Bonutti | |
| 5,685,831 A | 11/1997 | Floyd | |
| 5,688,137 A | 11/1997 | Bustance | |
| 5,690,260 A | 11/1997 | Aikins et al. | |
| 5,690,609 A | 11/1997 | Heinze, III | |
| 5,695,452 A | 12/1997 | Grim et al. | |
| 5,695,520 A | 12/1997 | Bruckner et al. | |
| 5,704,904 A | 1/1998 | Dunfee | |
| 5,704,937 A | 1/1998 | Martin | |
| 5,708,977 A | 1/1998 | Morkunas | |
| 5,718,670 A | 2/1998 | Bremer | |
| 5,722,940 A | 3/1998 | Gaylord, Jr. et al. | |
| 5,724,993 A | 3/1998 | Dunfee | |
| 5,725,139 A | 3/1998 | Smith | |
| 5,728,054 A | 3/1998 | Martin | |
| 5,728,168 A | 3/1998 | Laghi et al. | |
| 5,732,483 A | 3/1998 | Cagliari | |
| 5,735,807 A | 4/1998 | Cropper | |
| 5,737,854 A | 4/1998 | Sussmann | |
| 5,746,218 A | 5/1998 | Edge | |
| 5,752,640 A | 5/1998 | Proulx | |
| 5,778,565 A | 7/1998 | Holt et al. | |
| 5,782,782 A | 7/1998 | Miller | |
| 5,795,316 A | 8/1998 | Gaylord | |
| RE35,940 E | 10/1998 | Heinz et al. | |
| 5,816,251 A | 10/1998 | Glisan | |

(56) References Cited

U.S. PATENT DOCUMENTS

| | | | |
|---|---|---|---|
| 5,819,378 | A | 10/1998 | Doyle |
| 5,823,981 | A | 10/1998 | Grim et al. |
| 5,826,766 | A | 10/1998 | Aftanas |
| 5,827,211 | A | 10/1998 | Sellinger |
| 5,830,167 | A | 11/1998 | Jung |
| 5,836,493 | A | 11/1998 | Grunsted et al. |
| 5,840,050 | A | 11/1998 | Lerman |
| 5,840,051 | A | 11/1998 | Towsley |
| 5,848,979 | A | 12/1998 | Bonutti et al. |
| 5,853,378 | A | 12/1998 | Modglin |
| 5,853,379 | A | 12/1998 | Ostojic |
| 5,857,988 | A | 1/1999 | Shirley |
| 5,868,292 | A | 2/1999 | Stephens et al. |
| 5,890,640 | A | 4/1999 | Thompson |
| 5,891,061 | A | 4/1999 | Kaiser |
| 5,893,871 | A | 4/1999 | Tanaka |
| 5,911,697 | A | 6/1999 | Biedermann et al. |
| 5,916,070 | A | 6/1999 | Donohue |
| 5,925,010 | A * | 7/1999 | Caprio, Jr. ............ A61F 5/0109 602/62 |
| 5,938,629 | A | 8/1999 | Bloedau |
| 5,950,628 | A | 9/1999 | Dunfee |
| 5,954,250 | A | 9/1999 | Hall et al. |
| 5,954,253 | A | 9/1999 | Swetish |
| 5,967,998 | A | 10/1999 | Modglin |
| 5,968,002 | A | 10/1999 | Morrisseau |
| 5,993,403 | A | 11/1999 | Martin |
| 6,007,503 | A | 12/1999 | Berger et al. |
| 6,010,472 | A | 1/2000 | Schiller |
| 6,027,466 | A | 2/2000 | Diefenbacher et al. |
| 6,029,273 | A | 2/2000 | McCrane |
| 6,036,664 | A | 3/2000 | Martin, Sr. et al. |
| 6,039,707 | A | 3/2000 | Crawford et al. |
| 6,063,047 | A | 5/2000 | Minne |
| 6,066,108 | A | 5/2000 | Lundberg |
| 6,070,776 | A | 6/2000 | Furnary et al. |
| 6,090,057 | A | 7/2000 | Collins et al. |
| 6,099,490 | A | 8/2000 | Turtzo |
| 6,110,138 | A | 8/2000 | Shirley |
| 6,117,096 | A | 9/2000 | Hassard |
| RE36,905 | E | 10/2000 | Noble et al. |
| 6,125,792 | A | 10/2000 | Gee |
| 6,129,638 | A | 10/2000 | Davis |
| 6,129,691 | A | 10/2000 | Ruppert |
| 6,156,001 | A | 12/2000 | Frangi et al. |
| 6,159,248 | A | 12/2000 | Gramnas |
| 6,182,288 | B1 | 2/2001 | Kibbee |
| 6,189,538 | B1 | 2/2001 | Thorpe |
| 6,190,343 | B1 | 2/2001 | Heinz et al. |
| D438,624 | S | 3/2001 | Reina |
| 6,206,932 | B1 | 3/2001 | Johnson |
| 6,213,968 | B1 | 4/2001 | Heinz et al. |
| 6,227,937 | B1 | 5/2001 | Principe |
| 6,245,033 | B1 | 6/2001 | Martin |
| 6,254,561 | B1 | 7/2001 | Borden |
| 6,256,798 | B1 | 7/2001 | Egolf et al. |
| 6,267,390 | B1 | 7/2001 | Maravetz et al. |
| 6,282,729 | B1 | 9/2001 | Oikawa et al. |
| 6,289,558 | B1 | 9/2001 | Hammerslag |
| 6,315,746 | B1 | 11/2001 | Garth et al. |
| 6,322,529 | B1 | 11/2001 | Chung |
| 6,325,023 | B1 | 12/2001 | Elnatan |
| 6,338,723 | B1 | 1/2002 | Carpenter et al. |
| 6,375,632 | B1 | 4/2002 | Albrecht et al. |
| 6,401,786 | B1 | 6/2002 | Tedeschi et al. |
| 6,413,232 | B1 | 7/2002 | Townsend et al. |
| 6,416,074 | B1 | 7/2002 | Maravetz et al. |
| 6,419,652 | B1 | 7/2002 | Slautterback |
| 6,425,876 | B1 | 7/2002 | Frangi et al. |
| 6,428,493 | B1 | 8/2002 | Pior et al. |
| 6,432,073 | B2 | 8/2002 | Pior et al. |
| 6,471,665 | B1 | 10/2002 | Milbourn et al. |
| 6,478,759 | B1 | 11/2002 | Modglin et al. |
| 6,494,853 | B1 | 12/2002 | Rossi et al. |
| 6,502,577 | B1 | 1/2003 | Bonutti |
| 6,503,213 | B2 | 1/2003 | Bonutti |
| 6,517,502 | B2 | 2/2003 | Heyman et al. |
| 6,540,703 | B1 | 4/2003 | Lerman |
| 6,589,195 | B1 | 7/2003 | Schwenn et al. |
| 6,602,214 | B2 | 8/2003 | Heinz et al. |
| 6,605,052 | B1 | 8/2003 | Cool et al. |
| 6,609,642 | B2 | 8/2003 | Heinz et al. |
| 6,623,419 | B1 | 9/2003 | Smith et al. |
| 6,652,596 | B2 | 11/2003 | Smith et al. |
| 6,656,144 | B1 | 12/2003 | Coligado |
| 6,676,617 | B1 | 1/2004 | Miller |
| 6,676,620 | B2 | 1/2004 | Schwenn et al. |
| 6,688,943 | B2 | 2/2004 | Nagaoka |
| 6,689,080 | B2 | 2/2004 | Castillo |
| 6,702,770 | B2 | 3/2004 | Bremer et al. |
| 6,711,750 | B1 | 3/2004 | Yoo |
| 6,711,787 | B2 | 3/2004 | Jungkind et al. |
| 6,726,643 | B1 | 4/2004 | Martin |
| 6,769,155 | B2 | 8/2004 | Hess et al. |
| 6,770,047 | B2 | 8/2004 | Bonutti |
| 6,773,411 | B1 | 8/2004 | Alvarez |
| 6,790,191 | B1 | 9/2004 | Hendricks |
| 6,802,442 | B1 | 10/2004 | Thompson |
| D499,806 | S | 12/2004 | Machin et al. |
| 6,827,653 | B2 | 12/2004 | Be |
| D501,078 | S | 1/2005 | Cabana |
| 6,852,088 | B2 * | 2/2005 | Gaylord .................... A61F 5/32 602/19 |
| 6,893,098 | B2 | 5/2005 | Kohani |
| 6,893,411 | B1 | 5/2005 | Modglin |
| 6,913,585 | B2 | 7/2005 | Salmon et al. |
| 6,921,375 | B2 | 7/2005 | Kihara |
| 6,921,377 | B2 | 7/2005 | Bonutti |
| 6,923,780 | B2 | 8/2005 | Price et al. |
| 6,926,685 | B1 | 8/2005 | Modglin |
| 6,936,021 | B1 | 8/2005 | Smith |
| 6,942,630 | B2 | 9/2005 | Behan |
| 6,951,547 | B1 | 10/2005 | Park et al. |
| 6,962,572 | B1 | 11/2005 | Zahiri |
| 6,964,644 | B1 | 11/2005 | Garth |
| 6,991,611 | B2 | 1/2006 | Rhee |
| 7,001,348 | B2 | 2/2006 | Garth et al. |
| 7,001,350 | B2 | 2/2006 | Grosso |
| 7,025,737 | B2 | 4/2006 | Modglin |
| 7,028,873 | B1 | 4/2006 | Collier et al. |
| 7,034,251 | B1 | 4/2006 | Child et al. |
| 7,048,707 | B2 | 5/2006 | Schwenn et al. |
| 7,074,204 | B2 | 7/2006 | Fujii et al. |
| 7,083,584 | B2 | 8/2006 | Coligado |
| 7,083,585 | B2 | 8/2006 | Latham |
| 7,087,032 | B1 | 8/2006 | Ikeda |
| 7,101,348 | B2 | 9/2006 | Garth et al. |
| 7,118,543 | B2 | 10/2006 | Telles et al. |
| 7,128,724 | B2 | 10/2006 | Marsh |
| 7,134,224 | B2 | 11/2006 | Elkington et al. |
| 7,137,973 | B2 | 11/2006 | Plauche et al. |
| 7,140,691 | B2 | 11/2006 | Kohani |
| 7,166,083 | B2 | 1/2007 | Bledsoe |
| 7,186,229 | B2 | 3/2007 | Schwenn et al. |
| 7,198,610 | B2 | 4/2007 | Ingimundarson et al. |
| 7,201,727 | B2 | 4/2007 | Schwenn et al. |
| 7,235,059 | B2 | 6/2007 | Mason et al. |
| 7,281,341 | B2 | 10/2007 | Reagan et al. |
| 7,306,571 | B2 | 12/2007 | Schwenn et al. |
| 7,306,573 | B2 | 12/2007 | Bonutti |
| 7,309,304 | B2 | 12/2007 | Stewart et al. |
| 7,316,660 | B1 | 1/2008 | Modglin |
| 7,320,670 | B1 | 1/2008 | Modglin |
| 7,322,950 | B2 | 1/2008 | Modglin |
| 7,329,231 | B2 | 2/2008 | Frank |
| 7,331,126 | B2 | 2/2008 | Johnson |
| 7,351,368 | B2 | 4/2008 | Abrams |
| 7,389,547 | B1 | 6/2008 | Wiens |
| 7,402,147 | B1 | 7/2008 | Allen |
| 7,404,804 | B2 | 7/2008 | Bonutti |
| 7,416,565 | B1 | 8/2008 | Al-Turaikl |
| 7,438,698 | B2 | 10/2008 | Daiju |
| 7,473,235 | B2 | 1/2009 | Schwenn et al. |
| 7,476,185 | B2 | 1/2009 | Drennan |

(56) References Cited

U.S. PATENT DOCUMENTS

| | | |
|---|---|---|
| 7,513,018 B2 | 4/2009 | Koenig et al. |
| 7,549,970 B2 | 6/2009 | Tweardy |
| 7,578,798 B2 | 8/2009 | Rhee |
| 7,591,050 B2 | 9/2009 | Hammerslag |
| 7,597,671 B2 | 10/2009 | Baumgartner et al. |
| 7,597,672 B2 | 10/2009 | Kruijsen et al. |
| 7,600,660 B2 | 10/2009 | Kasper et al. |
| 7,615,021 B2 | 11/2009 | Nordt, III et al. |
| 7,618,386 B2 | 11/2009 | Nordt, III et al. |
| 7,618,389 B2 | 11/2009 | Nordt, III et al. |
| 7,654,972 B2 | 2/2010 | Alleyne |
| 7,662,121 B2 | 2/2010 | Zours |
| 7,670,306 B2 | 3/2010 | Nordt, III et al. |
| 7,682,219 B2 | 3/2010 | Falla |
| 7,699,797 B2 | 4/2010 | Nordt, III et al. |
| 7,704,219 B2 | 4/2010 | Nordt, III et al. |
| 7,727,048 B2 | 6/2010 | Gransberry |
| 7,727,172 B2 | 6/2010 | Wang |
| 7,727,174 B2 | 6/2010 | Chang et al. |
| 7,757,307 B2 | 7/2010 | Wong |
| 7,775,999 B2 | 8/2010 | Brown |
| 7,806,842 B2 | 10/2010 | Stevenson et al. |
| 7,815,585 B2 | 10/2010 | Vollbrecht |
| 7,819,831 B2 | 10/2010 | Dellanno |
| 7,833,182 B2 | 11/2010 | Hughes |
| 7,842,000 B2 | 11/2010 | Lai et al. |
| 7,857,776 B2 | 12/2010 | Frisbie |
| 7,862,529 B2 | 1/2011 | Brown |
| 7,862,621 B2 | 1/2011 | Kloos et al. |
| 7,871,388 B2 | 1/2011 | Brown |
| 7,878,998 B2 | 2/2011 | Nordt, III et al. |
| 7,887,500 B2 | 2/2011 | Nordt, III et al. |
| 7,914,473 B2 | 3/2011 | Josey |
| D636,494 S | 4/2011 | Garth et al. |
| 7,922,680 B2 | 4/2011 | Nordt, III et al. |
| 7,950,112 B2 | 5/2011 | Hammerslag et al. |
| 7,954,204 B2 | 6/2011 | Hammerslag et al. |
| 7,959,591 B2 | 6/2011 | Powers et al. |
| 7,993,296 B2 | 8/2011 | Nordt, III et al. |
| 8,002,724 B2 | 8/2011 | Hu et al. |
| 8,006,877 B2 | 8/2011 | Lowry et al. |
| 8,038,635 B2 | 10/2011 | Dellanno |
| 8,038,637 B2 | 10/2011 | Bonutti |
| 8,047,893 B2 | 11/2011 | Fenske |
| 8,048,014 B2 | 11/2011 | Brown |
| 8,066,161 B2 | 11/2011 | Green et al. |
| 8,066,654 B2 | 11/2011 | Sandifer et al. |
| 8,091,182 B2 | 1/2012 | Hammerslag et al. |
| 8,142,377 B2 | 3/2012 | Garth et al. |
| 8,162,194 B2 | 4/2012 | Gleason |
| 8,162,864 B2 | 4/2012 | Kruijsen et al. |
| 8,172,779 B2 | 5/2012 | Ingimundarson et al. |
| 8,214,926 B2 | 7/2012 | Brown |
| 8,216,167 B2 | 7/2012 | Garth et al. |
| 8,303,528 B2 | 11/2012 | Ingimundarson et al. |
| 8,308,669 B2 | 11/2012 | Nace |
| 8,308,670 B2 | 11/2012 | Sandifer et al. |
| 8,308,869 B2 | 11/2012 | Gardner et al. |
| 8,372,023 B2 | 2/2013 | Garth et al. |
| 8,381,314 B2 | 2/2013 | Takamoto et al. |
| 8,556,840 B2 | 10/2013 | Burke et al. |
| 8,597,222 B2 | 12/2013 | Lucero et al. |
| 8,657,769 B2 | 2/2014 | Ingimundarson et al. |
| 8,728,019 B2 | 5/2014 | Kruijsen et al. |
| 8,795,215 B2 | 8/2014 | Rossi |
| 8,893,312 B2 | 11/2014 | Takamoto et al. |
| 9,370,440 B2 | 6/2016 | Ingimundarson et al. |
| 9,468,554 B2 | 10/2016 | Petursson et al. |
| 9,554,935 B2 | 1/2017 | Ingimundarson et al. |
| 9,572,705 B2 | 2/2017 | Ingimundarson et al. |
| 9,795,500 B2 | 10/2017 | Ingimundarson et al. |
| 9,987,158 B2 * | 6/2018 | Ingimundarson ..... A61F 5/0102 |
| 2001/0020144 A1 | 9/2001 | Heinz et al. |
| 2001/0031936 A1 | 10/2001 | Pior et al. |
| 2002/0032397 A1 | 3/2002 | Coligado |
| 2002/0068890 A1 | 6/2002 | Schwenn et al. |
| 2002/0148461 A1 | 10/2002 | Heinz et al. |
| 2002/0158097 A1 | 10/2002 | Beale |
| 2003/0000986 A1 | 1/2003 | Smith |
| 2003/0028952 A1 | 2/2003 | Fujii et al. |
| 2003/0125650 A1 | 7/2003 | Grosso |
| 2003/0125705 A1 | 7/2003 | Ruman et al. |
| 2003/0139698 A1 | 7/2003 | Hyson |
| 2003/0220594 A1 | 11/2003 | Halvorson et al. |
| 2003/0229301 A1 | 12/2003 | Coligado |
| 2004/0024340 A1 | 2/2004 | Schwenn et al. |
| 2004/0050391 A1 | 3/2004 | Kiwala et al. |
| 2004/0082895 A1 | 4/2004 | Price et al. |
| 2004/0097857 A1 | 5/2004 | Reinecke et al. |
| 2004/0108350 A1 | 6/2004 | Warren |
| 2004/0116260 A1 | 6/2004 | Drennan |
| 2004/0132380 A1 | 7/2004 | Kihara |
| 2004/0133138 A1 | 7/2004 | Modglin |
| 2004/0143204 A1 | 7/2004 | Salmon et al. |
| 2004/0162582 A1 | 8/2004 | Banziger |
| 2004/0254505 A1 | 12/2004 | Begley et al. |
| 2005/0054960 A1 | 3/2005 | Telles et al. |
| 2005/0059917 A1 | 3/2005 | Garth et al. |
| 2005/0067816 A1 | 3/2005 | Buckman |
| 2005/0081339 A1 | 4/2005 | Sakabayashi |
| 2005/0131323 A1 | 6/2005 | Bledsoe |
| 2005/0137508 A1 | 6/2005 | Miller |
| 2005/0154337 A1 | 7/2005 | Meyer |
| 2005/0160627 A1 | 7/2005 | Dalgaard et al. |
| 2005/0165338 A1 | 7/2005 | Iglesias et al. |
| 2005/0228325 A1 | 10/2005 | Zours et al. |
| 2005/0240134 A1 | 10/2005 | Brown |
| 2005/0251074 A1 | 11/2005 | Latham |
| 2005/0267390 A1 | 12/2005 | Garth et al. |
| 2005/0273025 A1 | 12/2005 | Houser |
| 2006/0011690 A1 | 1/2006 | Bareno |
| 2006/0052733 A1 | 3/2006 | Schwenn et al. |
| 2006/0064048 A1 | 3/2006 | Stano |
| 2006/0074365 A1 * | 4/2006 | Brown ................... A61F 13/06 602/24 |
| 2006/0079821 A1 | 4/2006 | Rauch |
| 2006/0129077 A1 | 6/2006 | Parizot |
| 2006/0135900 A1 | 6/2006 | Ingimundarson et al. |
| 2006/0135901 A1 | 6/2006 | Ingimundarson et al. |
| 2006/0135903 A1 | 6/2006 | Ingimundaron et al. |
| 2006/0155229 A1 | 7/2006 | Ceriani et al. |
| 2006/0156517 A1 | 7/2006 | Hammerslag et al. |
| 2006/0206992 A1 | 9/2006 | Godshaw et al. |
| 2006/0254598 A1 | 11/2006 | Saul |
| 2006/0260620 A1 | 11/2006 | Kazerooni et al. |
| 2007/0152007 A1 | 7/2007 | Kauss et al. |
| 2007/0167895 A1 | 7/2007 | Gramza et al. |
| 2007/0179417 A1 | 8/2007 | Schwenn et al. |
| 2007/0185425 A1 | 8/2007 | Einarsson et al. |
| 2008/0045873 A1 | 2/2008 | Zours |
| 2008/0091132 A1 | 4/2008 | Bonutti |
| 2008/0195010 A1 | 8/2008 | Lai et al. |
| 2008/0208090 A1 | 8/2008 | Vollbrecht |
| 2008/0208091 A1 | 8/2008 | Vollbrecht et al. |
| 2008/0249448 A1 | 10/2008 | Stevenson et al. |
| 2008/0262401 A1 | 10/2008 | Wagner et al. |
| 2008/0302839 A1 | 12/2008 | Murdoch et al. |
| 2008/0319362 A1 | 12/2008 | Joseph |
| 2009/0025115 A1 | 1/2009 | Duffy et al. |
| 2009/0030353 A1 | 1/2009 | Bonutti et al. |
| 2009/0030359 A1 | 1/2009 | Wikenheiser et al. |
| 2009/0062704 A1 | 3/2009 | Brown et al. |
| 2009/0082707 A1 | 3/2009 | Rumsey |
| 2009/0100649 A1 | 4/2009 | Bar et al. |
| 2009/0124948 A1 | 5/2009 | Ingimundarson et al. |
| 2009/0127308 A1 | 5/2009 | Mori et al. |
| 2009/0182253 A1 | 7/2009 | Grim et al. |
| 2009/0192425 A1 | 7/2009 | Garth et al. |
| 2009/0198166 A1 | 8/2009 | Shlomovitz |
| 2009/0275871 A1 | 11/2009 | Liu |
| 2009/0287128 A1 | 11/2009 | Ingimundarson et al. |
| 2010/0010568 A1 | 1/2010 | Brown |
| 2010/0037369 A1 | 2/2010 | Reichert |
| 2010/0139057 A1 | 6/2010 | Soderberg et al. |

(56) References Cited

U.S. PATENT DOCUMENTS

| | | | |
|---|---|---|---|
| 2010/0204630 A1 | 8/2010 | Sandifer et al. | |
| 2010/0205713 A1 | 8/2010 | Takamoto et al. | |
| 2010/0217167 A1 | 8/2010 | Ingimundarson et al. | |
| 2010/0228170 A1 | 9/2010 | Imai | |
| 2010/0234780 A1* | 9/2010 | Allen | A61F 5/0193 602/1 |
| 2010/0256717 A1 | 10/2010 | Brown | |
| 2010/0268139 A1 | 10/2010 | Garth | |
| 2010/0268141 A1 | 10/2010 | Bannister | |
| 2010/0274364 A1 | 10/2010 | Pacanowsky et al. | |
| 2010/0292622 A1 | 11/2010 | Weissleder et al. | |
| 2010/0299959 A1 | 12/2010 | Hammerslag et al. | |
| 2010/0318010 A1 | 12/2010 | Sandifer et al. | |
| 2011/0000005 A1* | 1/2011 | Brown | A61F 5/0111 2/227 |
| 2011/0009793 A1 | 1/2011 | Lucero et al. | |
| 2011/0046528 A1 | 2/2011 | Stevenson et al. | |
| 2011/0082402 A1 | 4/2011 | Oddou et al. | |
| 2011/0098618 A1 | 4/2011 | Fleming | |
| 2011/0105971 A1 | 5/2011 | Ingimundarson et al. | |
| 2011/0137221 A1 | 6/2011 | Brown | |
| 2011/0144551 A1 | 6/2011 | Johnson | |
| 2011/0152737 A1 | 6/2011 | Burke et al. | |
| 2011/0178448 A1 | 7/2011 | Einarsson | |
| 2011/0184326 A1 | 7/2011 | Ingimundarson et al. | |
| 2011/0266384 A1 | 11/2011 | Goodman et al. | |
| 2012/0010547 A1 | 1/2012 | Hinds | |
| 2012/0022420 A1 | 1/2012 | Sandifer et al. | |
| 2012/0029404 A1 | 2/2012 | Weaver, II et al. | |
| 2012/0078151 A1 | 3/2012 | Cropper | |
| 2012/0197167 A1 | 8/2012 | Kruijsen et al. | |
| 2012/0204381 A1 | 8/2012 | Ingimundarson et al. | |
| 2012/0220910 A1 | 8/2012 | Gaylord et al. | |
| 2012/0232450 A1 | 9/2012 | Garth et al. | |
| 2012/0270708 A1* | 10/2012 | Paulos | A61F 5/0102 482/124 |
| 2012/0245502 A1 | 11/2012 | Garth et al. | |
| 2012/0323154 A1 | 12/2012 | Ingimundarson et al. | |
| 2013/0006158 A1 | 1/2013 | Ingimundarson et al. | |
| 2013/0007946 A1 | 1/2013 | Brown | |
| 2013/0012853 A1 | 1/2013 | Brown | |
| 2013/0158457 A1 | 6/2013 | Garth et al. | |
| 2013/0174326 A1 | 7/2013 | Takamoto et al. | |
| 2013/0178775 A1* | 7/2013 | Paaske | A61F 5/0193 602/23 |
| 2013/0184628 A1 | 7/2013 | Ingimundarson et al. | |
| 2013/0190670 A1 | 7/2013 | Von Zieglauer | |
| 2013/0211302 A1 | 8/2013 | Brown | |
| 2013/0237891 A1 | 9/2013 | Fryman et al. | |
| 2013/0281901 A1 | 10/2013 | Ochoa | |
| 2013/0298914 A1 | 11/2013 | Shibaya et al. | |
| 2014/0081189 A1 | 3/2014 | Ingimundarson et al. | |
| 2014/0116452 A1 | 5/2014 | Ingimundarson et al. | |
| 2014/0135672 A1 | 5/2014 | Joseph et al. | |
| 2014/0207040 A1 | 6/2014 | Ingimundarson et al. | |
| 2014/0200121 A1 | 7/2014 | Von Hoffmann et al. | |
| 2014/0207041 A1 | 7/2014 | Ingimundarson et al. | |
| 2014/0336020 A1 | 11/2014 | Von Hoffmann et al. | |
| 2016/0228279 A1 | 8/2016 | Modglin et al. | |
| 2016/0250061 A1 | 9/2016 | Ingimundarson et al. | |

FOREIGN PATENT DOCUMENTS

| | | |
|---|---|---|
| AU | 20 1028 68 51 A1 | 3/2012 |
| AU | 20 1028 68 51 A2 | 5/2012 |
| CA | 2 112 789 A1 | 8/1994 |
| CA | 2 114 387 A1 | 8/1994 |
| CA | 2 767 353 A1 | 1/2011 |
| CA | 2 772 296 A1 | 3/2011 |
| CH | 577 282 A5 | 7/1976 |
| CH | 612 076 A5 | 7/1979 |
| CH | 624 001 A5 | 7/1981 |
| CN | 1311648 A | 9/2001 |
| CN | 1383799 A | 12/2002 |
| CN | 1461190 A | 12/2003 |
| CN | 101219079 A | 7/2008 |
| CN | 201101603 Y | 8/2008 |
| CN | 101444443 A | 6/2009 |
| CN | 101820783 A | 9/2010 |
| CN | 102470040 A | 5/2012 |
| DE | 1 197 192 B | 7/1965 |
| DE | 88 04 683 U1 | 6/1988 |
| DE | 38 22 113 A1 | 1/1990 |
| DE | 94 17 221 U1 | 1/1995 |
| DE | 93 15 776 U1 | 2/1995 |
| DE | 295 03 552 U1 | 4/1995 |
| DE | 199 45 045 A1 | 3/2001 |
| DE | 202 04 747 U1 | 7/2002 |
| DE | 103 29 454 A1 | 1/2005 |
| DE | 20 2004 015 328 U1 | 2/2005 |
| DE | 20 2005 007 124 U1 | 6/2005 |
| DE | 10 2005 017 587 A1 | 4/2006 |
| DE | 202009004817 U1 | 9/2010 |
| EP | 0 393 380 B1 | 9/1992 |
| EP | 0 589 233 A1 | 3/1994 |
| EP | 0 614 624 A1 | 9/1994 |
| EP | 0 614 625 A1 | 9/1994 |
| EP | 0 657 149 A1 | 6/1995 |
| EP | 0 589 232 B1 | 11/1995 |
| EP | 0 693 260 B1 | 9/1998 |
| EP | 0 651 954 B1 | 2/1999 |
| EP | 1016351 A1 | 7/2000 |
| EP | 1 159 940 A2 | 12/2001 |
| EP | 1 236 412 A1 | 9/2002 |
| EP | 1 342 423 A1 | 9/2003 |
| EP | 1 588 678 A1 | 10/2005 |
| EP | 1 743 608 A2 | 1/2007 |
| EP | 1 985 264 A1 | 10/2008 |
| EP | 2 200 545 A1 | 6/2010 |
| EP | 2 451 412 A1 | 5/2012 |
| EP | 2 473 072 A1 | 7/2012 |
| FR | 1 104 562 A | 11/1955 |
| FR | 2 757 073 A1 | 6/1998 |
| FR | 2 952 807 A1 | 5/2011 |
| GB | 826 041 A | 12/1959 |
| GB | 909 970 A | 11/1962 |
| GB | 2 133 289 A | 7/1984 |
| JP | H07-246212 A | 9/1995 |
| JP | 3031760 U | 12/1996 |
| JP | H09-273582 A | 10/1997 |
| JP | H10-237708 A | 9/1998 |
| JP | 2000-290331 A | 10/2000 |
| JP | 2001-204851 A | 7/2001 |
| JP | 3091470 U | 1/2003 |
| JP | 2003-175063 A | 6/2003 |
| JP | 2004-016732 A | 1/2004 |
| JP | 2004-041666 A | 2/2004 |
| JP | 2004-160075 A | 6/2004 |
| JP | 2004-209050 A | 7/2004 |
| JP | 2007-291536 A | 11/2007 |
| JP | 3142546 U | 6/2008 |
| JP | 2008-178618 A | 8/2008 |
| JP | 2009-082697 A | 4/2009 |
| JP | 2012-011550 A | 1/2012 |
| JP | 2013-503268 A | 1/2013 |
| JP | 2013-536010 A | 9/2013 |
| WO | 94/01496 A1 | 1/1994 |
| WO | 95/03720 A2 | 2/1995 |
| WO | 97/03581 A1 | 2/1997 |
| WO | 00/53045 A1 | 9/2000 |
| WO | 2004/110197 A2 | 12/2004 |
| WO | 2005/086752 A3 | 4/2005 |
| WO | 2005/086752 A2 | 9/2005 |
| WO | 2006/121413 A1 | 11/2006 |
| WO | 2007003148 A1 | 1/2007 |
| WO | 2009/017499 A1 | 2/2009 |
| WO | 2009/017949 A1 | 2/2009 |
| WO | 2009/052031 A1 | 4/2009 |
| WO | 2009/068503 A1 | 6/2009 |
| WO | 2010/141958 A1 | 12/2010 |
| WO | 2011/005430 A1 | 1/2011 |
| WO | 2011/025675 A1 | 3/2011 |
| WO | 2011066323 A1 | 6/2011 |

(56) References Cited

FOREIGN PATENT DOCUMENTS

| WO | 2012/029917 A1 | 3/2012 |
|---|---|---|
| WO | 2013-016670 A1 | 1/2013 |
| WO | 2016138215 A1 | 9/2016 |

OTHER PUBLICATIONS

Mehlman, Charles T. et al., "Hyphenated History: Knight-Taylor Spinal Orthosis"; American Journal of Orthopedics; Jun. 2000; pp. 479-483, vol. 29, Issue 6.

Pamphlet—"Bledsoe Phillippon K.A.F. Positioning Kit", Bledsoe Brace Systems, Medical Technology Inc., 2004, 2 pages.

Posture Control Brace. Soft Form, Orthopaedic by Design, FLA Orthopedics, Inc., 1 page; 2004. http://www.flaorthopedics.com.

Michael Pfiefer, MD et al., "Effects of a New Spinal Orthosis on Posture, Trunk Strength, and Quality of Life in Women with Postmenopausal Osteoporosis—a Randomized Trial", American Journal of Physical Medicine & Rehabilitation, vol. 83, No. 3, Mar. 2004, USA, pp. 177-186.

Scoliosis Specialists About the SpineCor Brace; 2006-2012; http://www.scoliosisspecialists.com/aboutspinecorbrace.html. Retrieved from Internet on Aug. 1, 2013.

Hsu et al., "Principles and Components of Spinal Orthoses", AAOS Atlas of Orthoses and Assistive Devices, 4th Ed., Chapter 7, 2008, pp. 89-111.

Spinomed Brochure—Spinal Orthosis for Vertebral Extension in Osteoporosis; Stellar Orthotics and Prosthetics Group, 2 pages, retrieved from Internet Sep. 23, 2013. http://www.stellaroandp.com/spotlight.html.

Sato, Ena et al., "Effect of the WISH-type hip brace on functional mobility in patients with osteoarthritis of the hip: evaluation using the timed Up & Go Test", Prosthetics and Orthotics International 2012 36:25 originally published online Nov. 17, 2011, http://poi.sagepub.com/content/36/125 [retrieved from internet on Jan. 22, 2014].

Silosheath Brochure, Soft Socket Gel Liner, 4 pages, 1994.

International Search Report from International PCT Application No. PCT/US2014/012860, dated Apr. 17, 2014.

International Search Report from PCT Application No. PCT/US2016/043505, dated Oct. 13, 2016.

International Search Report from PCT Application No. PCT/US2018/049969, dated Nov. 16, 2018.

Partial International Search Report from PCT Application No. PCT/US2017/052143, dated Dec. 22, 2017.

\* cited by examiner

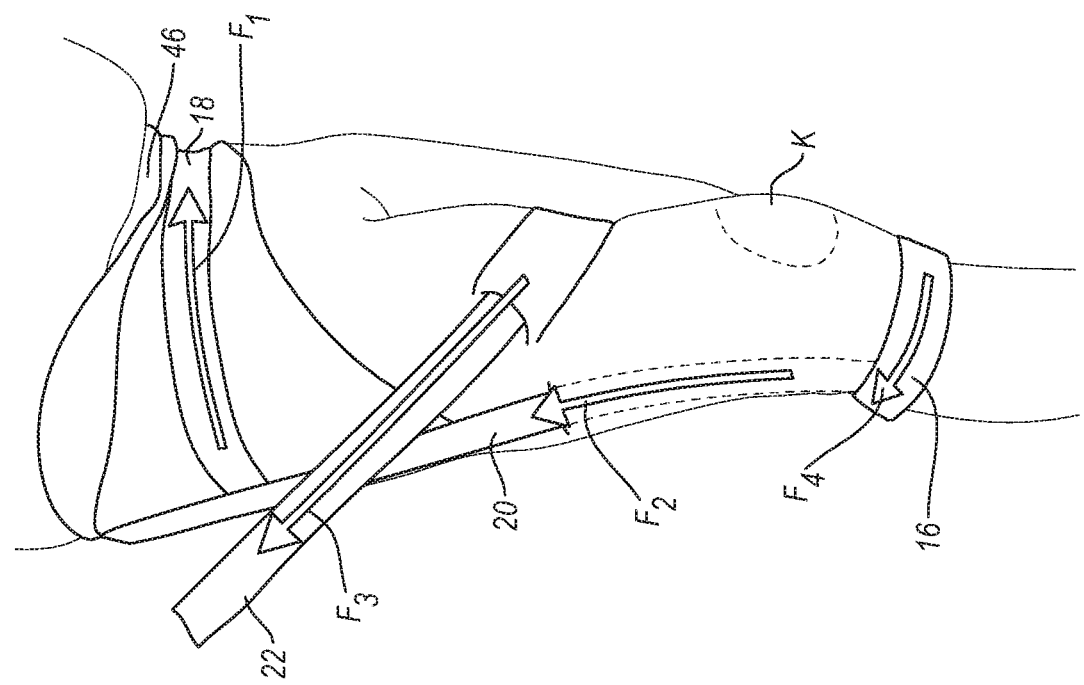
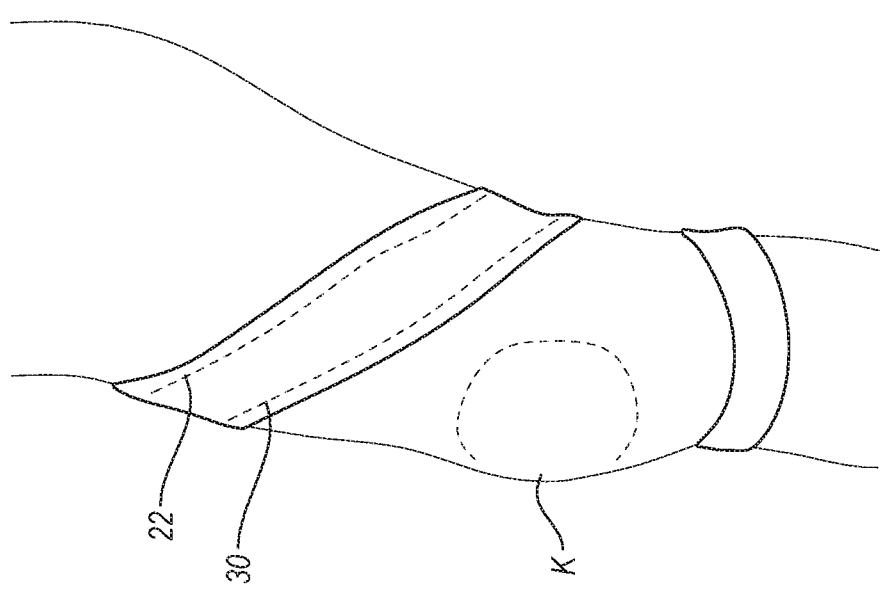

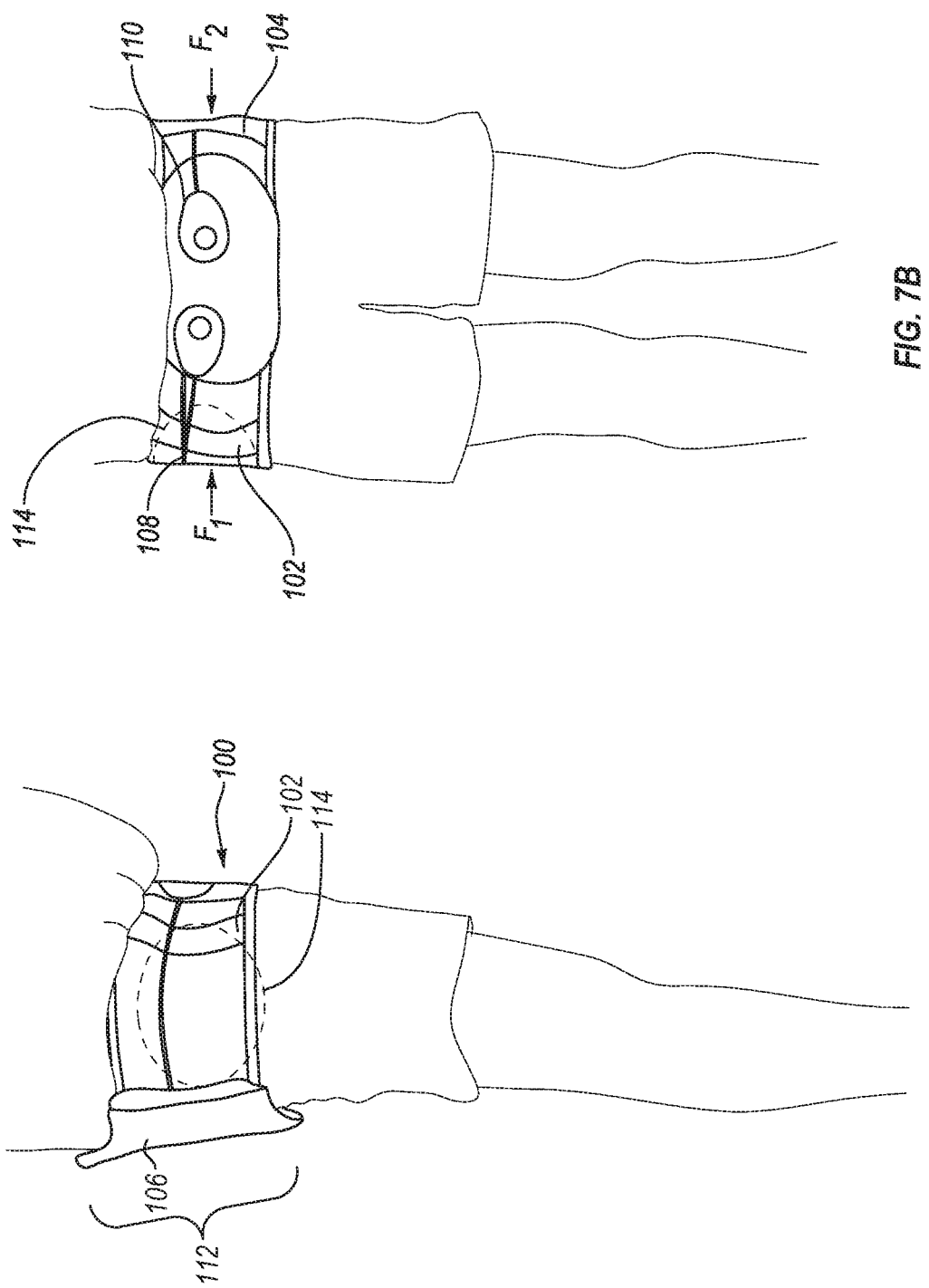

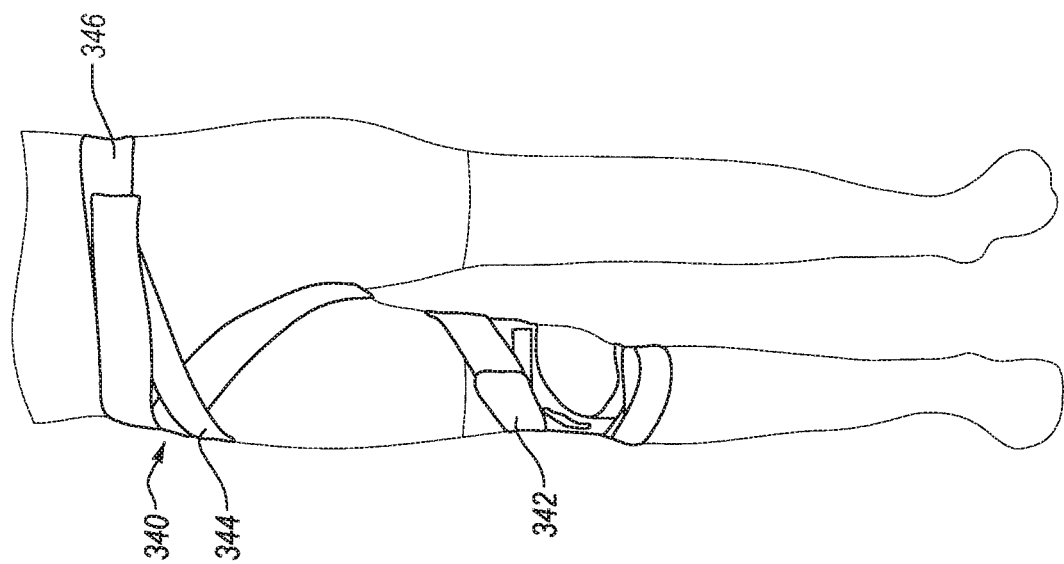
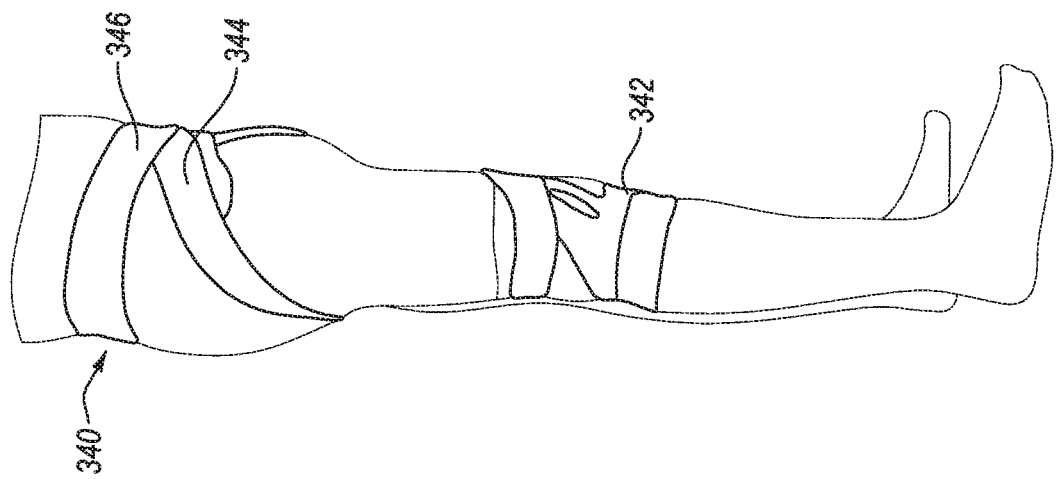
FIG. 24

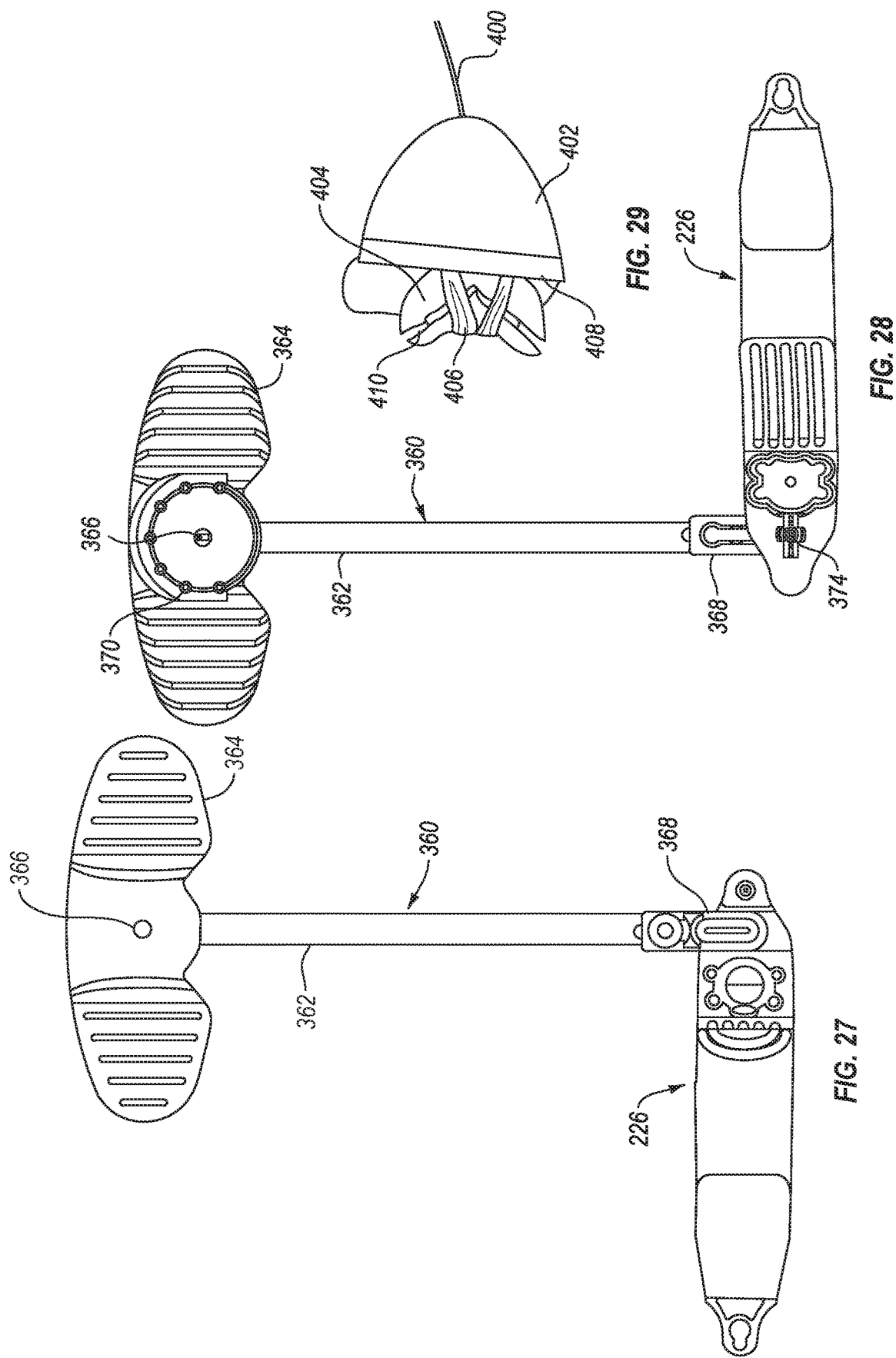

ORTHOPEDIC DEVICE FOR TREATING COMPLICATIONS OF THE HIP

FIELD OF ART

The embodiments of this disclosure are directed to orthopedic devices, particularly to a garment and/or hip orthosis for treating complications of the hip and methods for using the same.

BACKGROUND

Conventional hip braces and supports are mainly directed towards post-operative treatment of arthritis related surgeries (such as arthroplasties and arthroscopies). Few if any braces and supports are designed to treat osteoarthritis development or reduce the symptoms related to arthritis of the hip.

Braces and supports can assist weak muscles such as gluteus medius believed to be implicated in the sensation of pain. Re-positioning of the joint is also considered to be beneficial for other indications, such as anterior-collateral-ligament (ACL) injuries, and may offer improved control of the knee. One particular group of patients at risk includes female athletes who experience pain caused by non-contact ACL injuries because of landing from a jump.

A common problem with landing from a jump is a hyperextended valgus knee position causing internal rotation. It is believed that the root cause of this problem may be a weak gluteus medius causing the hip to over-extend and transfer the landing load onto the quadriceps instead of the gluteus medius. Therefore by flexing, abducting and externally rotating the hip one may alter the knee position and reduce the load on the ACL when landing from a jump.

Re-positioning or encouraging a preferred position of the hip relative to the joint may also reduce the load in the medial compartment of the knee and control proper tracking of the patella. Patella pain may be caused by lateral shift. Most patella braces and supports attempt to push the patella medially, however, by rotating the femur externally one may achieve better results by moving the femur relative to the patella instead of trying to push straight on the patella. It is known that the medial compartment loading for a patient having osteoarthritis is linked to the adduction moment of the knee.

It is more recently understood the medial compartment load is also linked to the knee extension moment. By rotating the femur externally, one may create a "toe-out" gait shown to reduce the load on the quadriceps and may directly reduce the load on the medial compartment.

Hip orthoses may be used for preventing hip dislocation, and provide early mobilization after hip surgery while minimizing post-surgical complications. Certain surgical operations include hip joint replacements or complete or partial revision surgery, and hip arthroscopy. These orthoses can reduce the length of hospitalization and rehabilitation, and the total period for convalescence. Hip orthoses may also treat persistent hip pain and non-operable hip deformities.

Prophylaxis or hip dislocation is a problem that occurs when the femoral head is displaced in the acetabulum or the hip socket. Typically, after hip surgery, a hip orthosis is needed for immobilization and support to aid in rehabilitation by preventing such a dislocation again.

The head of the femur meets the pelvis at the acetabulum and forms the hip joint. The head of the femur ("femoral head") and the acetabulum form as a ball-and-socket joint that allows for flexion, extension, abduction, adduction and circumduction. The hip is arranged for weight bearing, and there are connective ligaments for supporting the hip joint. The trochanter of the femur is located generally opposite the femoral head, and includes a lateral surface that serves at the insertion of the tendon of the gluteus medius.

Known hip orthoses used to prevent hip dislocation typically may have an adjustable hinge, which only allows for rotation of the upper leg about the hip joint in forward and backward directions. These hip orthoses have the drawback of failing to provide a dynamic abducting force on the leg throughout an entire range of motion. The abducting force may be provided while standing, but is not applied when sitting. Because the conventional orthoses hold the leg in abduction rigidly, this may lead to abnormal gait patterns and compliance issues.

Like other joints, hips may develop osteoarthritis of the hip as the articular cartilage between the femoral head and the acetabulum breaks down. The breakdown of the cartilage causes pain, swelling and deformity. As a result of the osteoarthritis, a patient having osteoarthritis of the hip may have difficulty walking. While osteoarthritis cannot be reversed, nonsurgical treatment may involve rest, anti-inflammatories and/or weight loss. If one has later stages of osteoarthritis of the hip, one may undergo total hip replacement surgery.

The wear of cartilage is particularly troublesome when loads are placed on the hip. Although there are plenty of solutions for treating osteoarthritis of the knee, few, if any, braces and supports have been offered to successfully treat hip osteoarthritis, specifically for reducing a load on the hip. Thus, there is a need and demand for an orthopedic device arranged for treating hip osteoarthritis.

Another concern regarding complications of the hip and associated vertebral column involves pelvic tilt and lordosis. Pelvic tilt refers to the orientation of the pelvis in regard to the femurs upon which they rest and in space. There are various forms of pelvic tilt including anterior pelvic tilting result in front tilt and rear rising of the pelvis when hip flexors shorten and hip extensors lengthen, and posterior pelvic tilt involving front rise and rear tilt of the pelvis when hip flexors lengthen and the hip extensors shorten. Lateral pelvic tilt describes tilting in both directions.

Lordosis is often associated with pelvic tilt, and is the inward curvature of the lumbar and cervical vertebral column. A major factor of lordosis is anterior pelvic tilt, which results in the pelvis tipping forward when resting on top of the femurs. A variety of health conditions can cause lordosis and include imbalances in muscle strength and length such as in the hamstrings and hip extensors and flexors.

Another spinal disorder is spinal stenosis, which involves the abnormal narrowing of the spinal canal. One form of spinal stenosis is lumbar spinal stenosis that occurs at the lower back. In lumbar stenosis, the spinal nerve roots in the lower back are compressed which can lead to symptoms of sciatica. Sciatica refers to tingling, weakness or numbness radiating from the lower back and into the buttocks and lower legs.

A variety of solutions exist for treatment of excessive pelvic tilt, lordosis and spinal stenosis of the lower back, however rare are solutions including orthopedic devices capable of treating both the hip and these aforementioned disorders.

SUMMARY

The orthopedic devices described are designed to reduce the load on the hip joint and encourage a positional shift of the joint believed to reduce pain by guiding the hip away from areas having worn or damaged cartilage. With mobility improved or restored, a user can engage in various activities without limitations of a constantly painful hip. Increased mobility helps avoid weight gain that may exacerbate symptoms of osteoarthritis of the hip.

According to a preferred embodiment, the orthopedic device is a garment and/or hip orthosis for treating complications of the hip. The garment and/or hip orthosis may provide means for trochanter compression, pelvis support, lumbar compression, variously directed straps, and thigh support. The trochanter compression and internal/external rotation strap provide pain relief through compression and skin protection, unloading of joints through compression and sealing, and unloading by load transfer. Adjustable dosing of straps enables pain management and ease of use. Reduced pelvis drop is allowed on the contralateral side by the pelvis support. The lumbar compression increases stability and support. Thigh support with a dosing system provides easy and consistent use for anchoring the orthopedic device on the leg, and hip adduction when required.

The garment (for example, a pair of tights extending over the waist and at least the upper leg) according to this disclosure may protect primary arthroplasty patients at risk of dislocation, hip revision, recurrent dislocations, and inoperable hip abnormalities or for preventative use in everyday living. Certain embodiments may also treat osteoarthritis of the hip, pelvic tilt, lordosis and spinal stenosis.

Embodiments of the garment described secure and control the femoral head in the acetabulum by providing a dynamic force on the leg and hip socket to prevent dislocation and treat instances of osteoarthritis. Forces may be exerted on the trochanter to urge the femoral head into the acetabulum.

The garment allows the user freedom of movement since the upper leg can move in all directions and not only in one direction while a desired interplay of forces can continue to act on the hip. This offers more comfort and the possibility of more efficient exercise of the muscles around the hip joint, which muscles may be weakened due to surgery.

In a first embodiment, the garment includes an upper belt member or belt and a lower wrap securing about the knee and/or thigh to position and anchor garment onto a user's body. A plurality of straps is arranged on the garment in a plurality of orientations to provide different directional forces over the user. The straps may be detachable and attachable at a plurality of predetermined locations. The straps may be also semi-elastic to encourage certain movements through their elasticity and softly prevent certain movements through their resistance. The prevention of movement is neither rigid nor stops movement but rather provides feedback and inhibits certain movement.

The straps can be integrated into a garment. The functionality from the straps can be achieved using textile patterns where portions of the textile will have different elastic properties providing feedback, or straps integrated into the garment separately adjustable using hook and loop or other tightening methods. The straps may extend at least in part through various sleeves formed on the garment to control movement. The sleeves may be formed from inelastic material to stabilize the straps and provide additional support while not inhibiting the elasticity of the straps.

The straps are preferably anchored at a first end to the garment and movably adjustable at a second, free end at various locations on the garment according to the tension and anatomy of the user.

A flexion strap may be attached to the anterior portion of the belt and anterior portion of the lower wrap. The strap encourages flexion and prevents extension of the hip. An abduction strap may be attached to the lateral portion of the upper belt member and the lateral portion of the lower wrap. The abduction strap encourages abduction and prevents adduction of the hip.

An exorotational strap may be attached to the lateral side over the posterior of the garment and spirals over the anterior side of the thigh and to the medial side towards posterior portion of the lower wrap. The strap encourages exorotation of the hip, and prevents endorotation. The strap encourages abduction and flexion of the hip, while preventing adduction and extension.

The garment may include a waist strap or belt extending laterally about the pelvis and circumferentially tightening over the trochanter of the femur to encourage placing or securing the femoral head in the hip socket. A lower wrap or band may extend laterally near the knee and form part of the lower wrap to serve as an anchor point for at least the abduction and the exorotational straps. The lower wrap may include first and second straps extending above and below the knee respectively, or the lower leg strap may be located singularly either above or below the knee.

The hip orthosis according to this disclosure may protect primary arthroplasty patients at risk of dislocation, hip revision, recurrent dislocations, and inoperable hip abnormalities or for preventative use in everyday living. Certain embodiments may also treat osteoarthritis of the hip. The hip orthosis may form part of the garment and/or be in supplement to the hip garment.

Pain relief is achieved by various embodiments by applying pressure on the greater trochanter by using a tensioning system, such as a pulley-type, to tension the orthosis over the trochanter. The upper part of the garment may be made from a non-stretchable material to better transmit the force from the tensioning system to the trochanter area. Using an elastic strap creates rotation of the leg. The upper part of the strap is fixed to the back area of the garment. Depending on the required rotation, internal or external, the strap is taken between the legs and to the front of the thigh or directly to the front of the thigh and then in both cases secured to a lower tightening unit using a fastening device. Using a frame fastened to the garment once the tensioning system has been tightened and fully secured creates abduction of the leg.

The orthopedic device, particularly the lumbar support in combination or considered alone with the tensioning system, may be used to improve immobilization of the lower back, by resisting flexion, extension, pelvic tilt, spinal rotation, and lateral bending. Another mechanism is pelvic stabilization in which the lumbar support maintains proper alignment of the pelvis in relation to the spine, and reduces pain in the lumbo-sacral region. Yet another mechanism is hydrostatic lift that occurs when the abdominal cavity is gently compressed, and the intra-abdominal pressure is increased. In yet another mechanism, the lumbar support introduces lordosis support or maintains lumbar support in order to provide correct lumbar lordosis for pain relief, spinal stabilization and improved posture.

The orthopedic device may include a plate system in combination with the tensioning system, or the tensioning system alone whether by placement or structure, may provide lordosis support to exert pressure to introduce and maintain correct lumbar lordosis for pain relief, spinal stabilization and improved posture such as by decreasing lordosis and increasing pelvic tilt.

Embodiments of the hip orthosis described secure and control the femoral head in the acetabulum by providing a dynamic force on the leg and hip socket to prevent dislocation and treat instances of osteoarthritis. This dynamic force mechanism follows the anatomical motion of the hip joint by maintaining the prescribed flexion and extension restrictions. Forces may be exerted on the trochanter to urge the femoral head into the acetabulum. Features of the hip orthosis attribute to a more stable and versatile orthosis over conventional braces.

Because of the versatility in sizing of the garment, there is only need for a few sizes, and a clinician may make further size adjustments by trimming belt segments and various cables. The garment provides pain relief and comfort through compression and skin protection. The orthosis enables trochanter compression with an optional pad, which allows for pain relief by unloading through compression and sealing, and unloading by load transfer.

The embodiments may include an internal or external rotation strap that permits adjustable dosing for pain management and versatility depending on whether internal or external rotation control is desired. The embodiments also allow for pelvis support by inhibiting reduced pelvis drop on a contralateral side. Lumbar compression is also allowed which increases stability and support. Thigh support is achieved with dial tensioning providing easy and consistent use for anchor and effective hip abduction when required.

The hip orthosis according to this disclosure may protect primary arthroplasty patients at risk of dislocation, hip revision, recurrent dislocations, and inoperable hip abnormalities or for preventative use in everyday living. Certain embodiments may also treat osteoarthritis of the hip.

In an embodiment of the hip orthosis, it may include a spring assembly for operatively preventing adduction movement of an upper leg by a spring force. The spring assembly operatively exerts a force and/or a moment on the upper leg which makes the upper leg abduct, viewed from the front side of the person, preferably independently of the position of the upper leg regarding the trunk.

The hip orthosis allows the user freedom of movement since the upper leg can move in all directions and not only in one direction while a desired interplay of forces can continue to act on the hip. This offers more comfort and the possibility of more efficient exercise of the muscles around the hip joint, which muscles are weakened due to surgery.

In use, the spring assembly exerts a force on the hip joint, such that the hip is pressed into its socket under the influence of that force, so the risk of dislocation is reduced further. The spring assembly also exerts a moment on the hip joint. This allows the upper leg to be given a preferred position regarding the trunk and/or to rotate it to a preferred position. The moment is directed so the upper leg is rotated substantially outwards, at least into a direction transverse to the sagittal plane. This prevents excessive abduction of the upper leg (towards the other leg), and reduces the risk of hip dislocation.

Other embodiments of the hip orthosis may be hingedly attached to the garment, such at a portion located above the knee. The hip orthosis may be without the spring assembly, but rather include a strut connecting at one end to a trochanter support and another end to the garment above the knee.

From these features, the various embodiments described herein provide pain relief, especially for users suffering from superior lateral osteoarthritis. The embodiments are compliant and provide comfort to encourage users to wear the garment throughout the day and prevent discouragement from wearing the brace. The features of the embodiments are simple to use, so after the initial fitting, the user does not feel encumbered by adjusting the orthosis. Because of the streamlined configuration of the orthosis, a user may wear it under clothing to avoid public display of its use.

The hip orthosis may be modified to include attachments and kits to treat additional indications than just osteoarthritis. Embodiments include maternity and spinal stenosis. Modifications may be made to any of the components described herein to offer improved functioning, lighter weight features and other improvements discussed in this disclosure.

The numerous advantages, features and functions of the embodiments will become readily apparent and better understood in view of the following description and accompanying drawings. The following description is not intended to limit the scope of the orthopedic device, but instead merely provides exemplary embodiments for ease of understanding.

BRIEF DESCRIPTION OF THE DRAWINGS

These and other features, aspects, and advantages of the embodiments will become better understood regarding the following description, appended claims, and accompanying drawings.

FIG. 5 is a detailed medial side view of the garment according to FIG. 1.

FIG. 6 is a schematic view of the garment according to FIG. 1 showing the directional forces created by tensioning various straps.

FIGS. 7A-7C are side, front and rear views of another hip orthosis embodiment according to the disclosure.

FIG. 24 includes schematic views showing a hip orthosis embodiment arranged for derotational strapping in a hip.

FIGS. 27 and 28 disclose frontal and rear views of a strut assembly for use with embodiments described herein.

FIG. 29 is a schematic view of a length adjustment assembly for tensioning devices.

Figure 2:
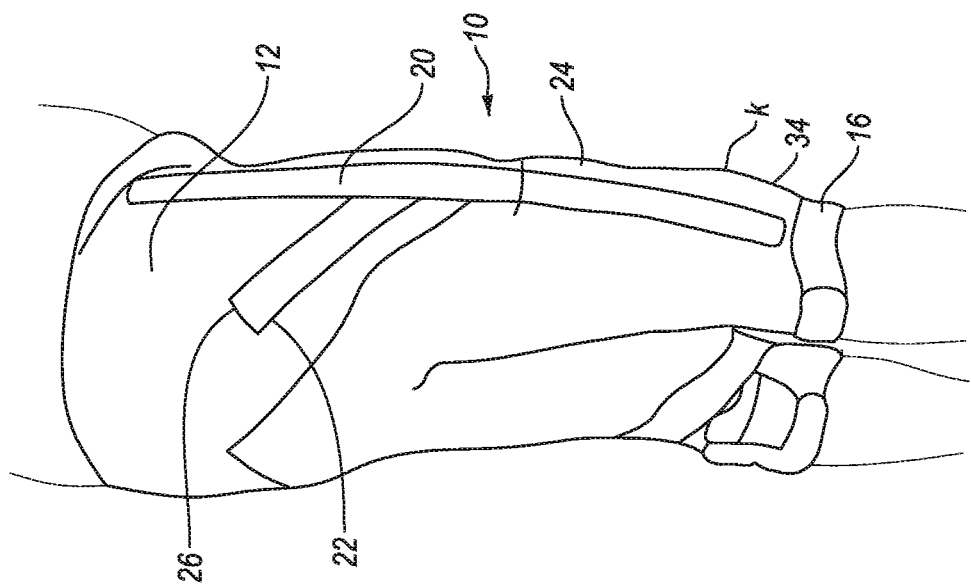
FIG. 2 is a perspective rear view of the garment according to FIG. 1.

In the various figures, similar elements are provided with similar reference numbers. The drawing figures are not drawn to scale, or proportion, but instead are drawn to provide a better understanding of the components, and are not intended to be limiting in scope, but rather provide exemplary illustrations.

DETAILED DESCRIPTION OF VARIOUS EMBODIMENTS

A. Overview

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

B. Environment and Context of Embodiments

For further ease of understanding the embodiments of an orthopedic device in the exemplary form of a garment and/or hip orthosis for treating complications of the hip and variants as disclosed, a description of a few terms is necessary.

The terms "rigid," "flexible," "compliant," and "resilient" may distinguish characteristics of portions of certain features of the straps and garment. The term "rigid" should denote an element of the device is generally devoid of flexibility. Within the context of features that are "rigid," it is intended to indicate that they do not lose their overall shape when force is applied, and may break if bent with sufficient force. The term "flexible" should denote that features are capable of repeated bending such that the features may be bent into retained shapes or the features do not retain a general shape, but continuously deform when force is applied.

The term "compliant" may qualify such flexible features as generally conforming to the shape of another object when placed in contact therewith, via any suitable natural or applied forces, such as gravitational forces, or forces applied by external mechanisms, for example, strap mechanisms. The term "resilient" may qualify such flexible features as generally returning to an initial general shape without permanent deformation. As for the term "semi-rigid," this term may be used to connote properties of support members or shells that provide support and are freestanding; however such support members or shells may have some degree of flexibility or resiliency. The term "elastic" may connote stretchability, and the term "semi-elastic" connotes various degrees of elasticity as compared to the term "inelastic" which may mean devoid or substantially devoid of any elasticity.

The embodiments of the disclosure are adapted for a human body, and may be dimensioned to accommodate different types, shapes and sizes of human body sizes and contours. For explanatory purposes, the orthopedic device embodiments described are referred to as corresponding to different sections of a body and are denoted by general anatomical terms for the human body.

For explanatory purposes, each orthopedic brace embodiment or component described may be divided into sections denoted by general anatomical terms for the human body. Such anatomical terms are provided to distinguish various elements of the brace embodiments from one another, but which are not to be considered to limit the scope of the invention.

Each of these terms is used in reference to a human leg, for example, which is divided in similar sections with a proximal-distal plane extending along the meniscus of the knee between the femur and tibia. The terms "proximal" and "distal" refer to locations of the brace that correspond to the location of the leg relative to the point of attachment of the leg to the body. The terms "upper" and "lower" may be used in combination with "proximal" and "distal" to connote gradations in location of "proximal" and "distal." The location at where the brace corresponds to the knee joint is used to generally delimit the proximal and distal sections of the brace.

The embodiments of the orthopedic device can also be considered to fall within "anterior" and "posterior" sections by an anterior-posterior plane. The anterior-posterior plane generally corresponds to the coronal or frontal plane of a human leg lying along the central longitudinal axis of a body. A posterior side or element is therefore located behind this anterior-posterior plane, whereas an anterior side or element is in front of the anterior-posterior plane.

The terms "inwardly" or "inner" commonly used to distinguish the side of the brace may be directed to the posterior side of the brace and adjacent to the leg of the user of the brace. Contrariwise, the terms "outwardly" or "outer" are used to denote the side of the brace opposite to the inwardly side.

The terms "medial" and "lateral" are relative terms generally understood as indicating location near the midsagittal plane or midline. Therefore, elements located near the midline are referred to as "medial" and those elements further from the midline are "lateral." The term "central" is used to denote the area along the midline of a joint dividing and sharing regions of the medial and lateral regions.

The term "adduction" is defined as being a movement towards the trunk. The term "abduction" is defined as being a movement by which a body part is moved away from the axis of the body.

The hip region is commonly considered as being located lateral to the gluteal region (i.e., the buttock), inferior to the iliac crest, and overlying the greater trochanter of the femur, or "thigh bone". In adults, three of the bones of the pelvis have fused into the hip bone that forms part of the hip region.

The hip joint, scientifically referred to as the acetabulofemoral joint, is the joint between the femur and acetabulum of the pelvis and its primary function is to support the weight of the body in both static (e.g., standing) and dynamic (e.g., walking or running) postures. The pelvic inclination angle, which is the single most important element of human body posture, is adjusted at the hips.

The pelvis is referred to as either the lower part of the trunk, between the abdomen and the thighs (sometimes also called pelvic region of the trunk), or the skeleton embedded in it (sometimes also called bony pelvis, or pelvic skeleton). The pelvic region of the trunk includes the bony pelvis, the pelvic cavity (the space enclosed by the bony pelvis), the pelvic floor, below the pelvic cavity, and the perineum, below the pelvic floor. The pelvic skeleton is formed in the area of the back, by the sacrum and the coccyx and anteriorly and to the left and right sides, by a pair of hip bones. The two hip bones connect the spine with the lower limbs. They are attached to the sacrum posteriorly, connected to each other anteriorly, and joined with the two femurs at the hip joints.

The waist or waist region is the part of the abdomen between the rib cage and the hips, and is often the narrowest part of the torso on proportionate people. The thigh or thigh region is considered the area between the pelvis and the knee.

The term "adduction" is defined as being a movement towards the trunk. The term "abduction" is defined as being a movement by which a body part is moved away from the axis of the body.

C. Various Embodiments of the Orthopedic Brace and Components for Use Therewith

In reference to FIGS. 1-5, a garment 10 for treating complications of the hip is illustrated. The garment includes an upper wrap in the form of a belt 12, a main body portion 14 extending over the thighs, and a lower band or wrap 16 located near the knees K. The upper and lower wraps 12, 16 serve as anchors to securing the garment on the user, and likewise for various straps attached to the garment. The lower wrap 16 may be secured below or above the knee, or both.

The belt 12 is attached around the user's pelvis/waist, anatomically shaped, and tightened using hook and loop, buckles or other fastener means. The belt 12 includes first and second belt segments arranged to overlap and secure to one another. By circumferentially compressing over the user's waist, the belt forms an upper anchor to the garment.

The belt 12 is preferably formed from a stretchable and compressible material arranged to extend over the user's waist and pelvis. The belt can have silicone patches integrated into the textile that creates a frictional interface to the skin or the user's undergarments to reduce migration, as shown in FIG. 6 under reference 46. The belt can be arranged with a tensioning or pulley system similar to a lumbar belt discussed in U.S. Pat. No. 8,172,779, granted on May 8, 2012, and incorporated by reference. The embodiments are not limited to pulleys and may include posts, sliders or other means for providing mechanical advantage for a cable. Alternatively, the tensioning system may be a plurality of straps replacing pulleys, cables and similar means.

A lateral strap 18 may be secured at a first end to the posterior of the garment and extend about the user's pelvis. The lateral strap 18 has a second end adjustably attachable to the garment. The lateral strap 18 is intended to provide localized and enhanced pressure over the user's trochanter to maintain the femoral head in the user's socket.

The body portion 14 may be formed from a generally sturdy fabric elastic material, such as Lycra or Spandex. The body portion 14 is configured to conform to the legs of the user and provide an interface over which the straps extend.

The lower wrap 16 may form a knee/thigh wrap anatomically shaped to slip onto the leg. The wrap can be solely around the thigh, or extend down below the patella. The knee/thigh wrap can have a hole for the patella, and include straps in the bottom, middle or top portion that allows for tightening to avoid migration. The wrap can also have integrated silicone patches, as discussed in connection with the upper wrap, to provide frictional resistance.

In the embodiments of FIGS. 2-5, the lower wrap 16 is arranged as a lateral strap extending adjacent to and below the user's knee. The lower wrap 16 forms a lower anchor to the garment, and prevents migration of the garment on the lower leg. In this configuration, the lower wrap 16 forms a gastroc strap that corresponds to the gastroc and secures the brace in place between the knee and the user's calf by the shape of the user's calf to inhibit migration. Alternatively, the lower wrap 16 may be located so it extends adjacent to and above the user's knee.

The lower wrap 16 may include a lower strap 32 (FIG. 4) allowing for tensioning of the lower wrap 16 over the leg. The lower wrap 16 may define an elasticized portion of the garment 10 having a channel through which the lower strap 32 extends. The lower wrap 16 is yet further tightened over the user's leg by adjustment of the elastic strap 32 relative to the channel. The lower strap 32 may be inelastic or elastic.

In a variation of the lower wrap 16 depicted in FIG. 1, the lower wrap 16 includes an upper circumferential strap 40 arranged to extend about the lower thigh above the knee, and a lower circumferential strap 50 arranged to extend about the lower leg below the knee. Medial and lateral elongate straps 42, 44 extend transversely relative to and connect the upper and lower circumferential straps 40, 50 to keep them secured to one another.

A longitudinal band or abduction strap 20 extends longitudinally along the lateral side of the garment, and is arranged to encourage abduction and prevents adduction of the hip. The abduction strap 20 is anchored at point 34 above the lower wrap 16, and is adapted to extend to the upper wrap 12 so a free end 28 secures to the upper wrap 12.

The body 14 may define a sleeve 24 having an opening 36 through which the abduction strap 20 extends from the lower wrap 16 to the upper wrap 12. The sleeve 24 has a greater width than the abduction strap 20 to permit adjustment of the abduction strap 20 relative to the sleeve 24. The sleeve 24 may be formed at least in part from a material inelastic to stabilize and support the area of the leg corresponding to the sleeve 24.

An oblique band or exorotational strap 22 extends from an anchor point at the posterior of the leg wrap 16 and spirals toward the medial posterior of the leg, over the anterior thigh and has a free end 26 securable to the posterior lateral side near or at the upper wrap. The exorotational strap 22 extends through a channel 30 formed from the lower wrap to a location on the anterior side of the garment. The channel 30 is wider than the exorotational strap 22 and is formed at least in part from a material inelastic to stabilize and support the exorotational strap 22 over the leg. The channel 30 assists in distributing pressure over the leg.

The garment 10 may be provided with a flexion strap 38 arranged from the lower wrap 16 and securing to the upper wrap 12 along the anterior of the garment generally along the midline. The flexion strap encourages flexion and prevents extension of the hip.

In a variation, the garment may be provided with an extension strap arranged on the posterior of the garment generally along the midline. The extension strap encourages extension and resists flexion.

FIG. 6 depicts various forces incurred by the various straps. The lateral strap 18 provides a circumferential force F1 about the pelvis to apply to the trochanter. The abduction strap 20 provides an upwardly force F2 from the knee to the pelvis to prevent adduction of a user's leg. The exorotational strap 22 provides a spiraling force F3 generally oblique to the forces F1, F2, to encourage abduction and therefore resist adduction. The lower strap 16 provides a circumferential force F4 to anchor a lower portion of the garment.

Figure 7C:
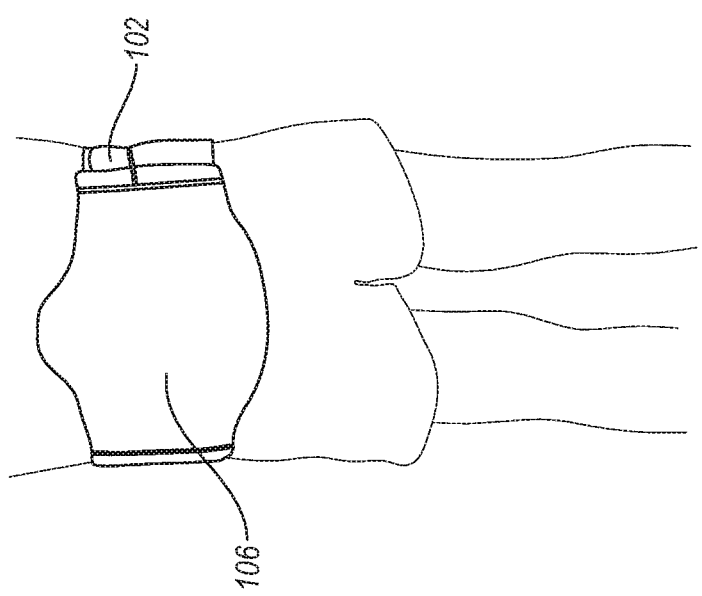

As shown in FIGS. 7A-7C, another embodiment of a hip orthosis includes a pelvic compression support 100 adapted to be secured about the user at the pelvis. This arrangement is distinguishable from a lumbar compression support discussed in U.S. Pat. No. 8,172,779 provided about the waist and intended to provide compression to the lumbar area of the user. The pelvic compression support 100 has a more significant width 112 than a conventional lumbar support, and is arranged to sit over the hips including the trochanter resting at least partially below a lumbar region of the user's back unlike the conventional lumbar support.

The pelvic compression support 100 includes first and second belt segments 102, 104 extending from a rear or posterior compression system 106 discussed more fully in U.S. Pat. No. 8,172,779. Tensioning devices 108, 110 extend from the compression system 106, and are intended to provide compressive adjustment to the rear compression system 106 and secure over the first and second belt segments 102, 104. Multiple tensioning devices may be provided on each side of the compression system. Each side may include upper and lower tensioning devices each selectively adjusting various locations of the compression system.

Figure 8:
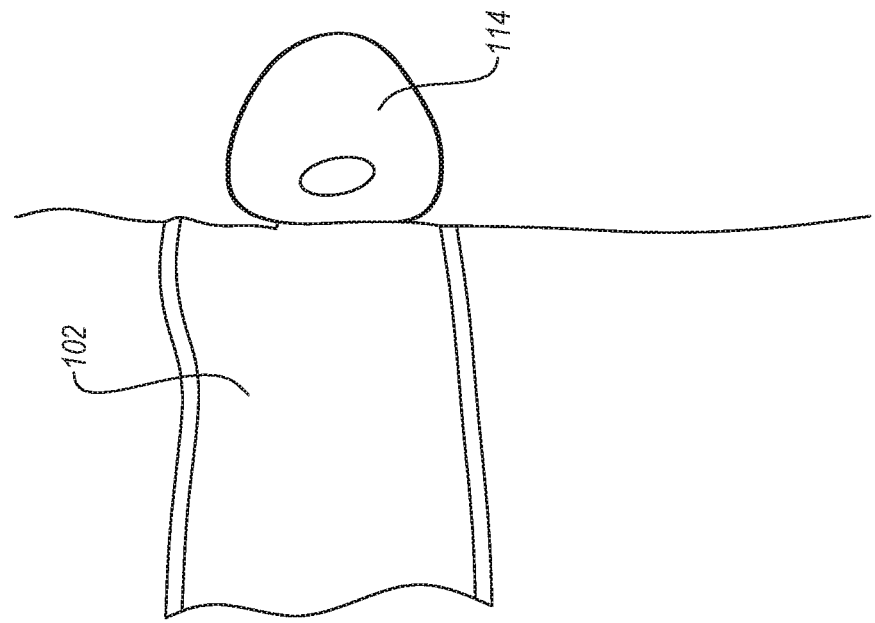
FIG. 8 is a schematic view of the hip orthosis of FIGS. 7A-7C with the first belt segment open showing a trochanter support.

FIG. 8 shows a trochanter support 114 located underneath the first belt segment 104, and adjacent the user's body. As the first and second belt segments 102, 104 are secured to one another, and the tensioning devices 108, 110 are used to tension the rear compression system, compressive support is provided particularly at the trochanter support 114, which urges the femoral head into the hip socket (acetabular) to provide relief to the user. The garment may be provided with inelastic fabric that is hook receivable to include a trochanter pad carried by the trochanter support.

Figure 1:
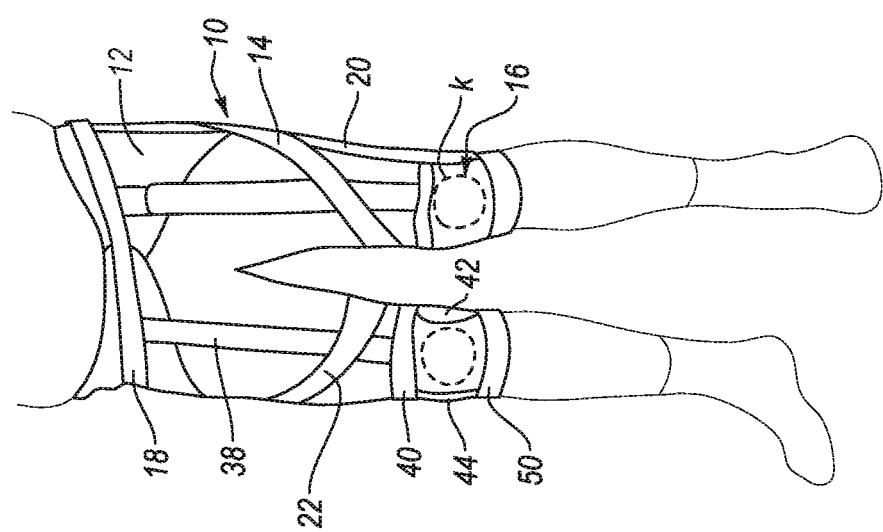
FIG. 1 is a perspective front view of an embodiment of a garment according to the disclosure.
Figure 4:
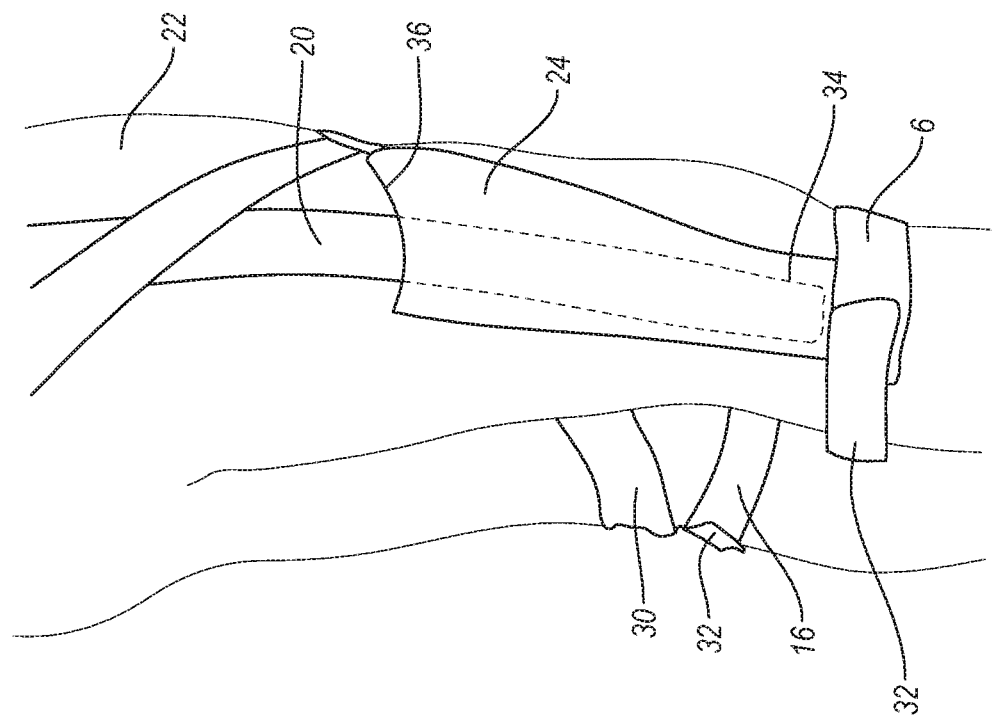
FIG. 4 is a detailed lateral side view of the garment according to FIG. 1.
Figure 3:
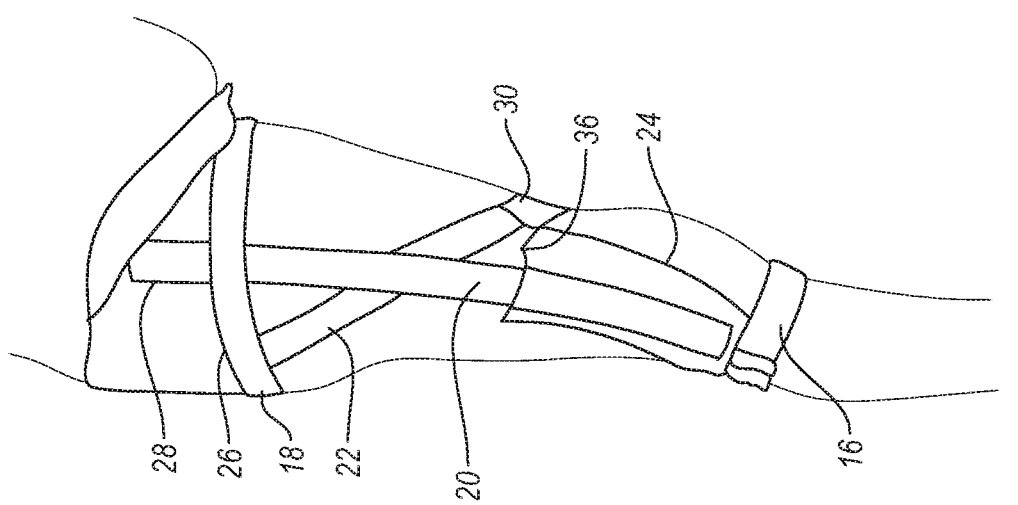
FIG. 3 is a side view of the garment according to FIG. 1.
Figure 9B:
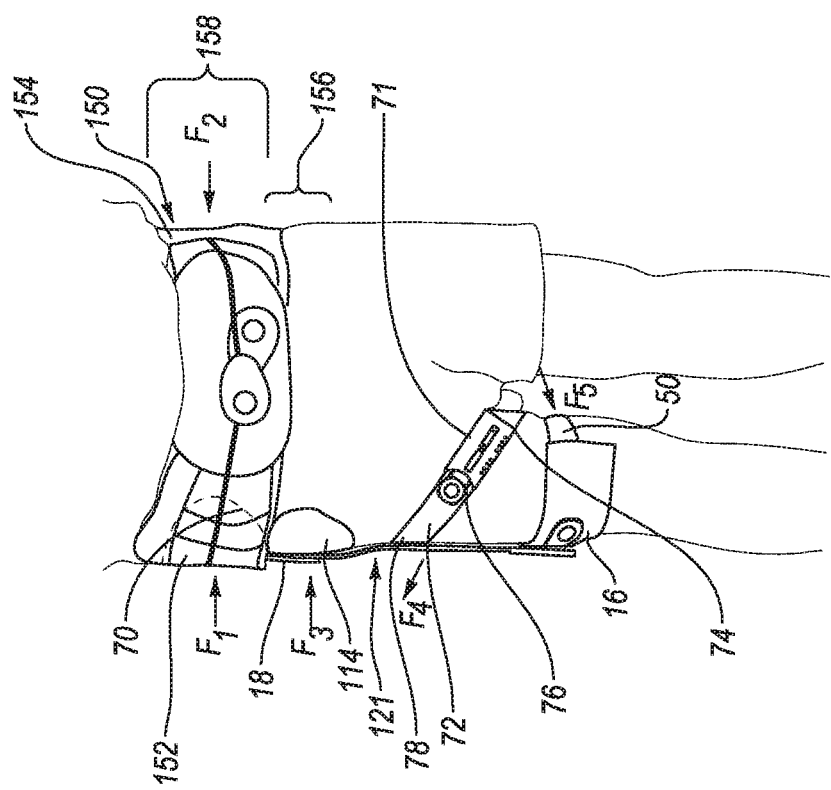
FIGS. 9A-9B are side and front views showing the hip orthosis of FIG. 1 in combination with a compression belt on a user.
Figure 9A:
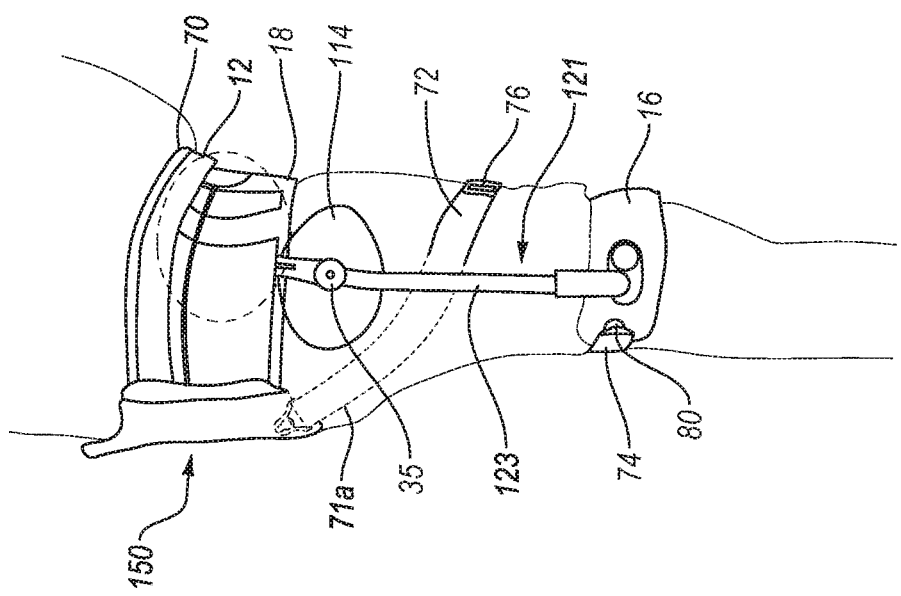

FIGS. 9A and 9B show the hip orthosis of FIG. 1 in combination with a compression belt or upper wrap 150. Unlike the compression belt of FIGS. 7A-7C, the compression belt 150 sits higher toward the waist of the user by a difference 156, and has a narrower width 158.

In this embodiment, the pelvic support 12 is located adjacent the user and underneath a first belt segment 152 which secures to a second belt segment 154. A pad 70 covering at least part of the pelvic support 12 may be retained by the pelvic support 12 to the first belt segment 152.

An exorotation strap 71 secures to a strut assembly 121 at an upper anchor 78 and wraps around the leg and secures to a lower anchor 80 on the lower support 16. The exorotation strap 71 defines a first segment 72 depending from the upper anchor 78 and couples to a second segment 74 by a tensioning device 76 providing incremental tensioning of the exorotation strap 71. The tensioning device 76 may correspond to the strap tightener assembly for an orthopedic device according to U.S. application Ser. No. 13/739,491, filed on Jan. 11, 2013 and published as U.S. patent application publication 2013/01846628 A1 on Jul. 18, 2013. Alternatively, the exorotation strap 71A (shown in dashed lines) may run underneath the strut assembly 121 and secure to the posterior side of the upper wrap 150.

The strut assembly 121 includes a strut 123 connecting to the lower wrap 16 and the pelvic support 12. The strut may carry a trochanter support 114, and a strut adjustment or pivot mechanism 35 may adjust position of the trochanter, as discussed more fully regarding the strut assembly of FIG. 30.

Figure 10B:
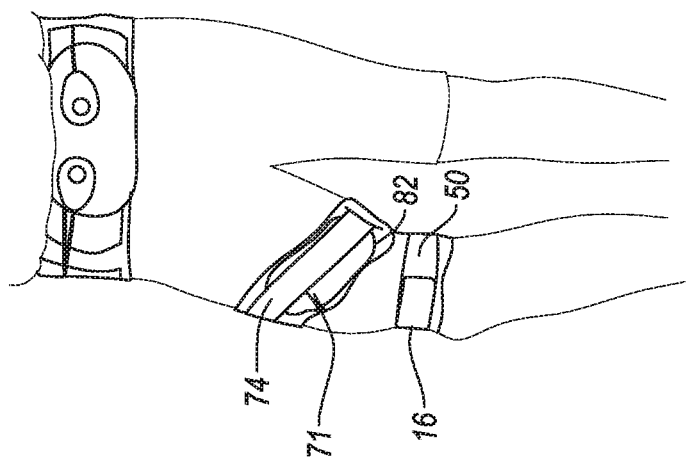
FIGS. 10A-10B are side and front views showing another hip orthosis embodiment according to the disclosure.
Figure 10A:
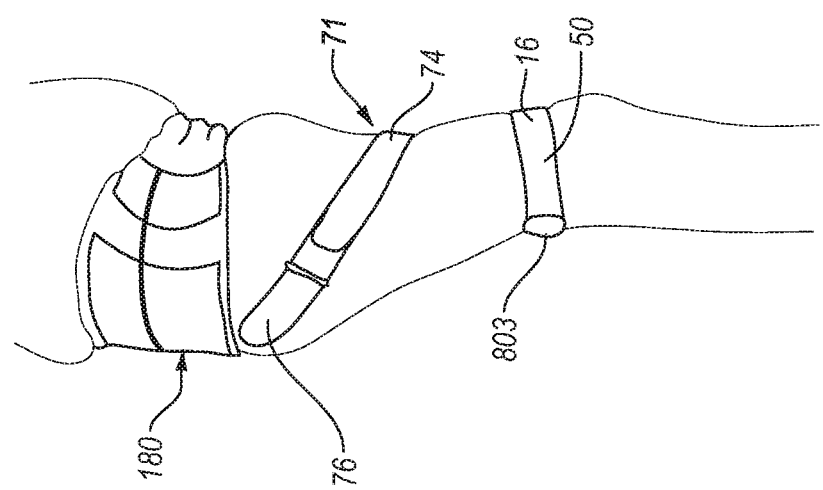

FIGS. 10A-10B show another embodiment of a hip orthosis employing the compression belt 150 of FIGS. 9A-9B and the exorotation strap 71 attached directly to a generally posterior side of the compression belt 150 on a lateral side of the leg. The tensioning device 76 is secured directly to the compression belt and allows for adjustment of the exorotation strap 71. The tensioning device 76 allows for tensioning of the second strap segment 74, which couples to the lower support 16. A strap support 82 may be in combination with the exorotation strap 71 to distribute pressure over the thigh.

Referring to the embodiment of FIGS. 11A-18, the orthopedic device 200 combines a garment and hip orthosis and includes first and second upper belt members 202, 204 adapted to wrap about a user's hip. A waist band 211 is located at a generally uppermost portion of the orthopedic device, and is adapted to secure to the waist of the user. Lower bands 213 are located at generally lowermost portions of the orthopedic device, and the inside surface of the lower bands 213 may include a frictional interface to engage the skin and prevent migration of the garment on the user.

The upper belt members 202, 204 having posterior or lateral ends that are joined to the garment 216 on the lateral and/or posterior sides of the orthosis by a joint 244 such as permanently by stitching or removably by hook and loop fastening. The upper belt members 202, 204 freely extend from the joint or stitching, and have anterior ends that are secured to one another by a buckle assembly 205. The anterior ends of the upper belt members have trimmable sections 207 bordered by trim lines allowing for sizing of the upper belt members to the specific dimensions of an individual user. The trim lines may be reduced thickness regions of the upper belt members.

Figure 11A:
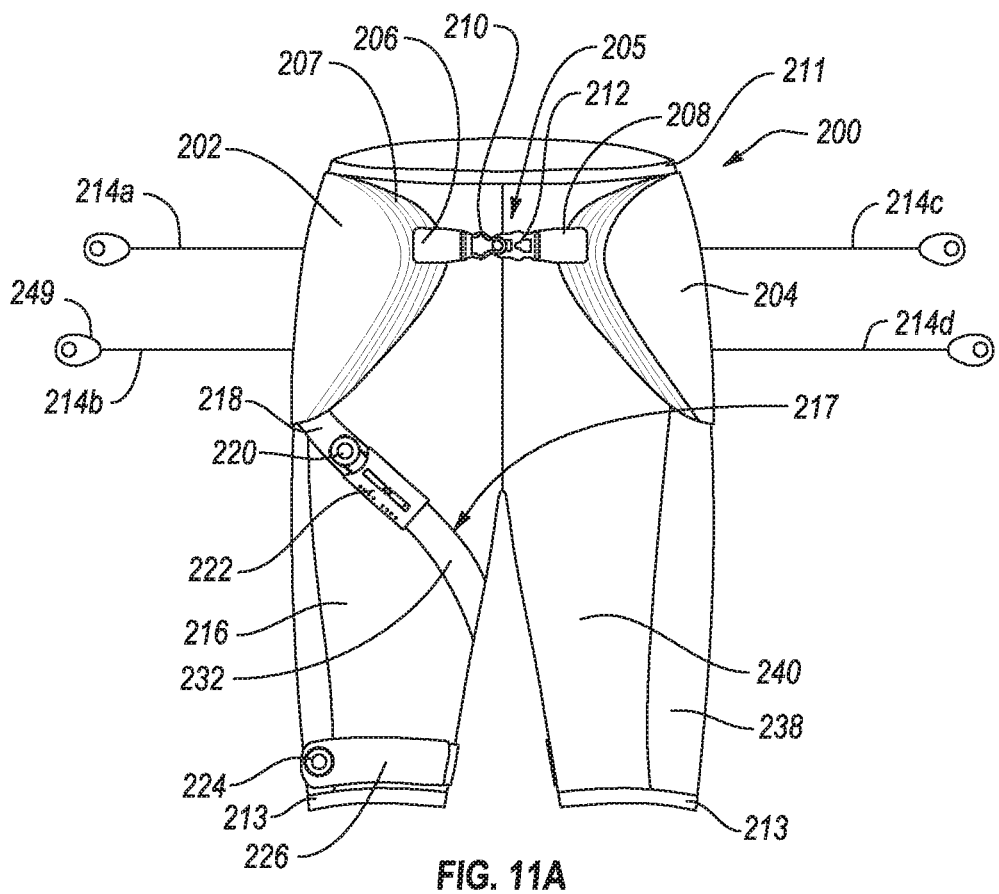
FIG. 11A is a front view showing another hip orthosis embodiment according to the disclosure.

The shape of the anterior side of the belt members is significant in that it extends more substantially toward the upper portion of the garment, as shown in FIG. 11A, and tapers in the extent it extends anteriorly toward the lower portion of the garment. The height of the belt members is preferably at its greatest at the joint to distribute forces created when the belt members are secured to one another. The tapering height of the belt members tracks generally the anatomy of the pelvic region of the user so that the anterior-most portion does not interfere with normal activities.

The garment 216 may include different sections having different stretchability, stiffness, or carry various surface textures for securing to various straps. Lateral portions 238 may have a stiffer property than portions 240 outside of the lateral portions 238. The lateral portions may be reinforced or possess the stiffer properties to provide additional resistance for controlling movement of the hip and legs. The lateral portions may also be substantially inelastic as compared to other portions of the garment outside the lateral portions.

Figure 11B:
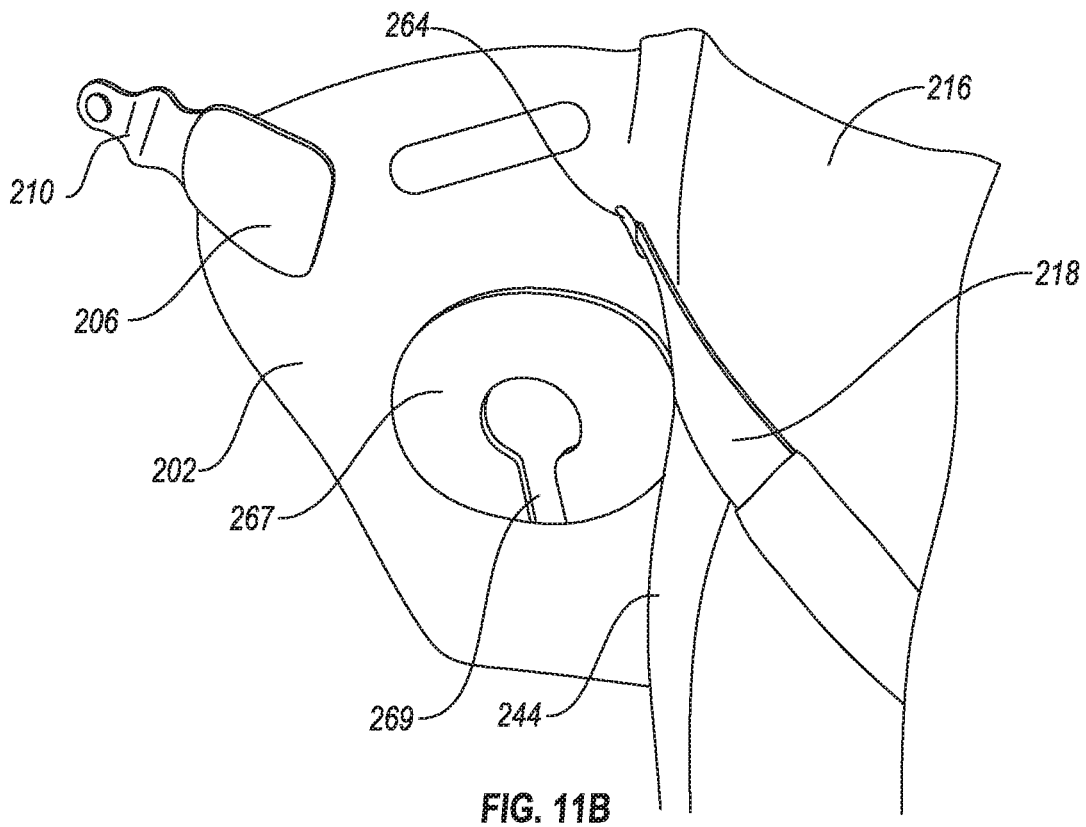
FIG. 11B is a schematic view showing opening of the hip orthosis of FIG. 11A and installation of a trochanter pad.

FIG. 11B shows insertion of a trochanter pad 267 along an inner surface of the upper belt member 206. The trochanter pad 267 may be removably secured along the inner surface by a hook and loop system, whereby the trochanter pad 267 includes a hook material segment arranged to secure to loop material formed along the inner surface. The trochanter pad 267 may have a pocket 269 arranged for receiving a frame element of a strut assembly, as discussed herein.

Figure 15A:
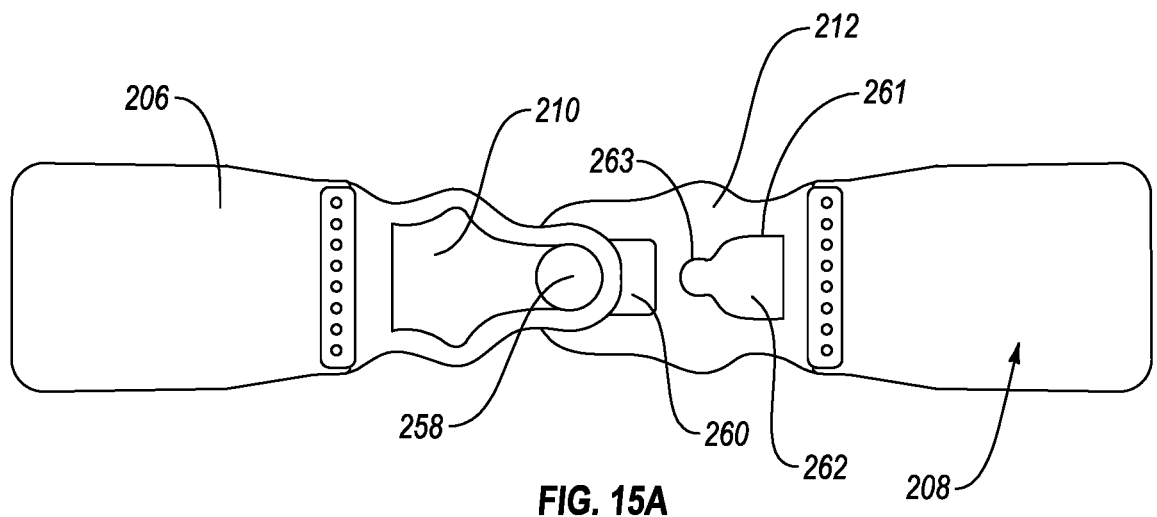
FIG. 15A is a schematic view of a closure system in the hip orthosis of FIG. 11A.

Observing FIGS. 11A and 15A, the buckle assembly 205 includes first and second segments 206, 208 depending from the first and second belt members 202, 204. The first and second segments may be trimmable to size according to an individual user, and may be elastic or inelastic. The first and second segments 206, 208 may comprise "alligator" type hook clamps forming opposed hook surfaces arranged to clamp onto a hook receivable surface of the first and belt members.

The first segment 206 carries a tab 210 having a catch 258, such as a pin or other protrusion, adapted to be received by a clip 212 carried by the second segment 208, thereby forming a buckle. The clip 212 may define a plurality of engagement openings 260, 262 for receiving and allowing the catch 258 to engage with the clip 212.

Each of the engagement openings 260, 262 is sized and configured for quick attachment of the catch 258. In the depicted embodiment, a larger opening 261 permits insertion of the catch 258 therethrough and a smaller opening 263 continuously depends from the larger opening 261 so the tab 210 can be pulled toward an end of the clip 212 to firmly engage the catch 258 within the smaller opening 263.

Figure 15B:
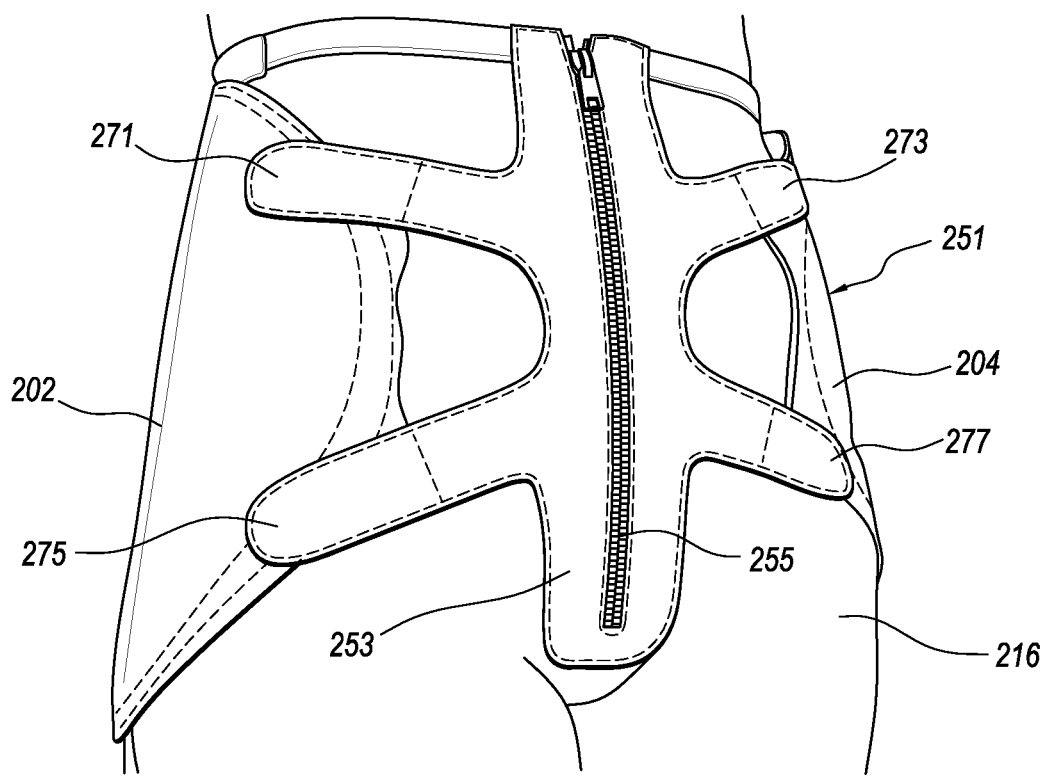
FIG. 15B is a schematic view of another closure system in the hip orthosis of FIG. 11A.

FIG. 15B illustrates an alternate closure system 251 for closing the anterior aspect of the orthosis or orthopedic device 200 of FIG. 11A. In this embodiment, the front closure 251 includes a plurality of straps 271, 273, 275, 277 that are arranged to secure at their outer ends to the first and second belt members 202, 204. The straps 271, 273, 275, 277 extend from a central panel 253 and a closure 255, such as a zipper, series of buttons or other known means, is located along the center of the central panel 253. The straps 271, 273, 275, 277 may be releasably tensioned to the belt members and the closure 255 permits a user to quickly open the anterior aspect of the garment, in the event it is desired to loosen, open or remove the garment for various activities, such as for bathroom activities.

The closure system of FIG. 15B may be modified so the closure is not straight, as depicted in FIG. 15B, but rather it may be arranged at an angle, and there may be a plurality of zippers. The closure may not be arranged centrally but instead, for example, may be located along either or both sides of the hip down toward the contralateral leg with at least one strap bearing hook material and loop material continuous.

Figure 15C:
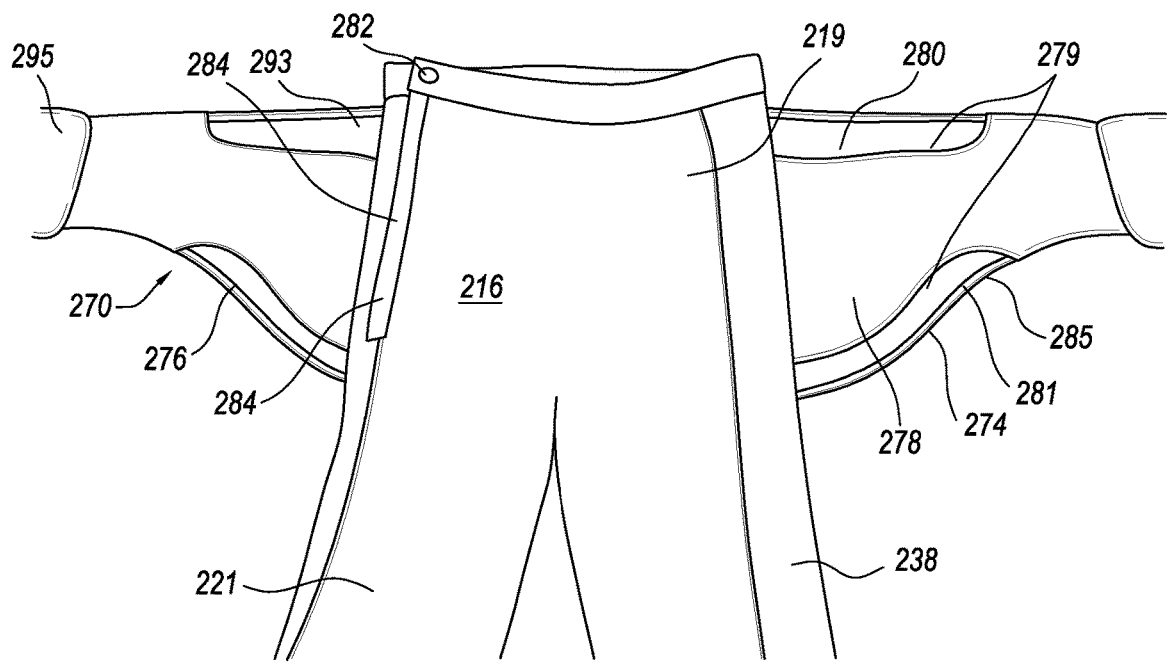
FIG. 15C is a schematic view of another closure system in the hip orthosis of FIG. 11A in an open configuration.
Figure 15D:
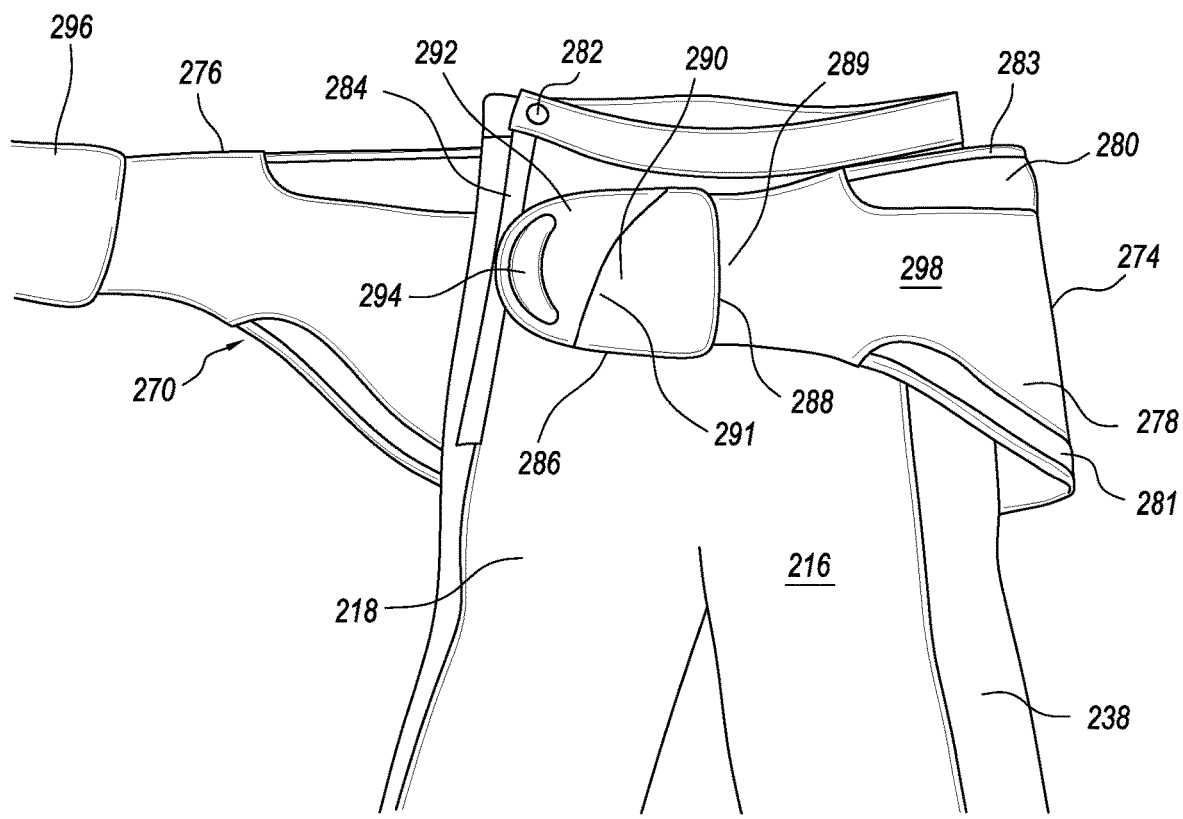
FIG. 15D is a schematic view of the closure system of FIG. 15C in a partially open configuration.
Figure 15E:
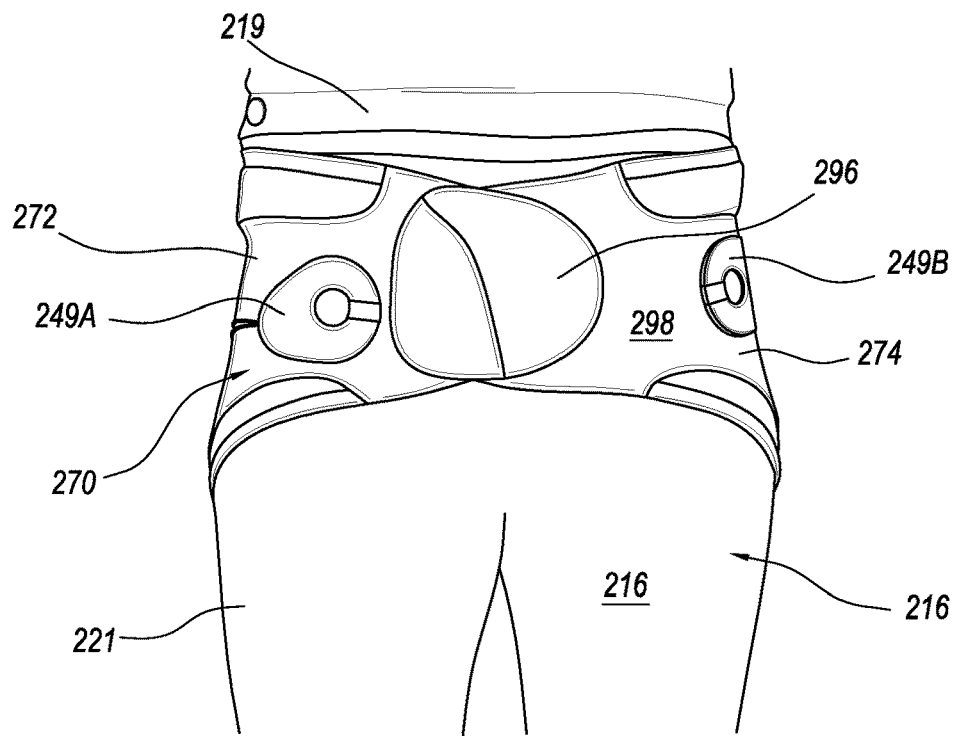
FIG. 15E is a schematic view of the closure system of FIG. 15C in a closed configuration.

FIGS. 15C-15E depict another closure system 270 in which the belt members 274, 276 secure to one another. The hip portion 219 of the garment 216 includes a fastener 282, such as a button, zipper, hook and loop, securing a flap 284 to a remainder of the garment 216. The flap 284 is arranged to open from a first side of the garment so a user has access to opening the anterior aspect of the garment 216. The flap 284 may be additional or alternatively secured to the garment by a closure of the type in the embodiment of FIG. 15B. In yet another alternative, the flap may be centrally located rather than located on a side.

The first and second belt members 274, 276 secure to and extend generally from first and second sides of the sides between the posterior and anterior regions of the garment or from the posterior region of the garment. The belt members 274, 276 are arranged to extend over the anterior region of the garment so as to overlap one another. The first and second belt members 274, 276 are arranged to extend over a posterior pelvic region of a user and exert pressure over the garment along with the compression system.

As shown in FIGS. 15C and 15D, the first and second belt members 274, 276 have a greatest width at first end 293 located at the posterior region of the garment 216 and have an upwardly taper toward a second end 295 adapted to be secured at the anterior region of the garment 216. The first and second belt members 274, 276 have a main panel 278 that is inelastic and opposed auxiliary panels 280, 281 secured to a periphery of the main panel 278 along its length and which are elastic relative to the main panel 278. An elastic edge bind 283 surrounds an outer periphery and joining to the main panel. The first and second auxiliary panels 280, 281 are located on opposed upper and lower sides, respectively of the main panel 278, and generally extend from the first end 293 at the side or posterior region of the garment and terminate before the second end 295 of the belt members 274, 276.

The belt members 274, 276 preferably have a taper 285 extending from the side or posterior region such that the first end 293 has a broadest height so as to encompass the side of the hip and the taper proceeds to the second end 295 to minimize the belt members over the anterior aspect of the orthosis. The belt members 274, 276 preferably extend above a leg portion 221 of the garment 216, such that the belt members 274, 276 are preferably confined within the hip portion 219.

In a variation, one of the belt members 274, 276 may be substantially longer than another one of the belt members. The longer of the belt members may extend to the posterior of the garment 216 and secure thereto by an appropriate fastener, such as by a buckle, strap, lock, etc. In another variation, the belt members may be modified with a closure system such as in the strap of FIGS. 18C-18E wherein a first one of the belt members defines an elongate slot through which an end of a second one of the belt members extends and secures to the first belt members.

The second end 295 of the first belt member 274 includes a removable clip 286 that secures over an end portion 289. The end portion 289 is trimmable and the clip 286 includes an attachment 288, such as an alligator clip arrangement for securing at least one side of the second end 295 of the first belt member 274. The trimmable end portion 289 enables better sizing of the orthosis by customizing for an individual user while minimizing the amount of sizes in which the orthosis may be offered. The second belt member 276 may also have a second clip 296 similarly arranged as the first clip 286, and is likewise trimmable in length from the second end portion thereof. The belts are not just arranged for being trimmed, but can alternatively be folded over so they are only temporarily reduced in size.

Either of the first and second clips 286, 296 may comprise a main portion 290 formed from an inelastic material, and a cover portion 292 formed from an elastic material. The cover portion 292 forms an opening 291 with the main portion 290 to define a pocket for insertion of a user's hand or fingers to belt manage tensioning of the belt members. A gripping or attaching element 294 may be provided on the clips so as to enable better grasping of the belt members or it may be replaced with a hook material for securing the belt members. A surface 298 of the belt members may comprise a hook receivable material to enable one or both of the clips to secure therewith as well as handles 249a, 249b of the first and second tensioning devices.

The orthosis 200 includes tensioning devices 214A-214D arranged for tensioning a compression system 229, and arranged to function similarly to the compression system in the embodiment of FIGS. 7A and 7B. Tensioning devices 214A and 214B correspond to the first belt member 202 and tensioning devices 214C and 214D correspond to the second belt member 204. Handles 249 of the tensioning devices are secured to the upper belt members, which may bear hook receivable material, and the handles themselves may carry hook material. As the compression system 229 is arranged on the posterior of the hip orthosis 200, the tensioning devices extend freely from the compression system 229 and pulling of the tensioning devices from the compression system 229 tensions the compression system over the pelvis.

Figure 15G:
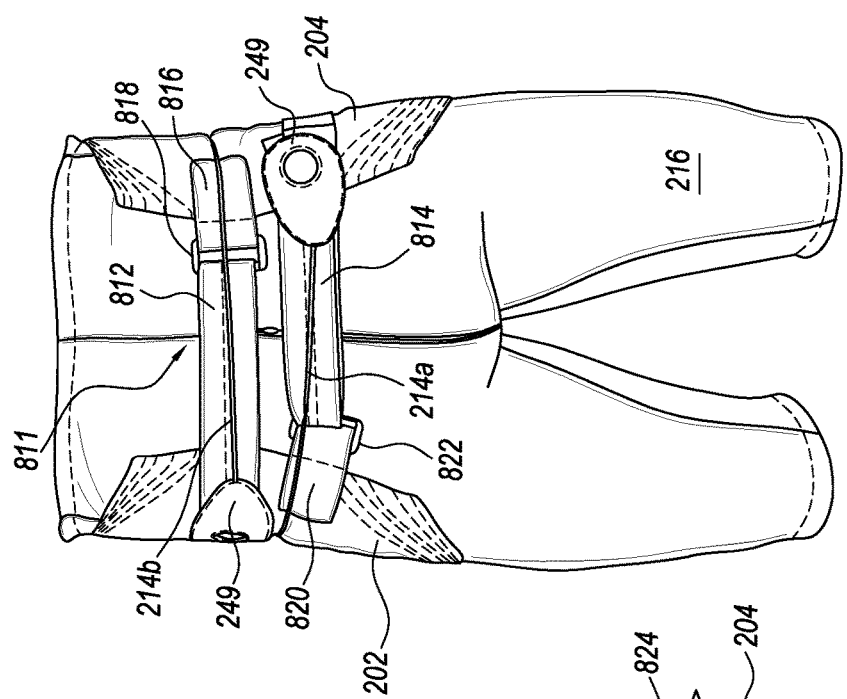
FIG. 15G is a schematic view of another closure system in the hip orthosis of FIG. 11A.
Figure 15H:
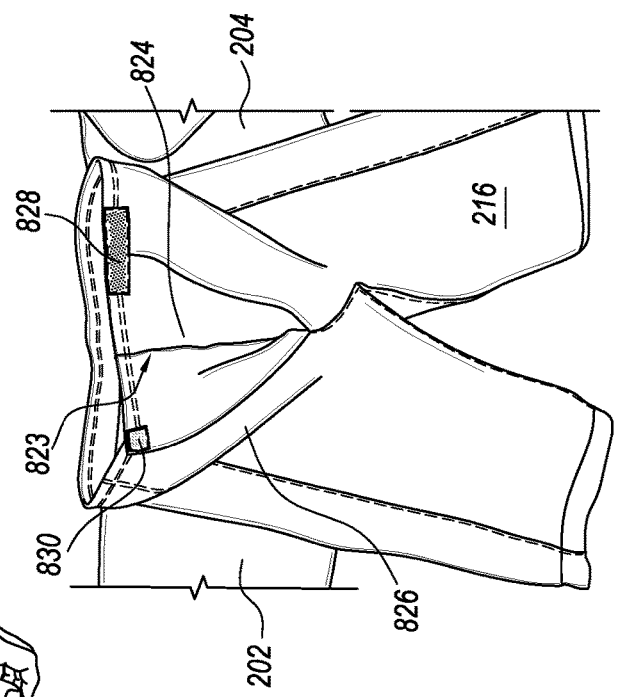
FIG. 15H is a schematic view of another closure system in the hip orthosis of FIG. 11A.
Figure 15F:
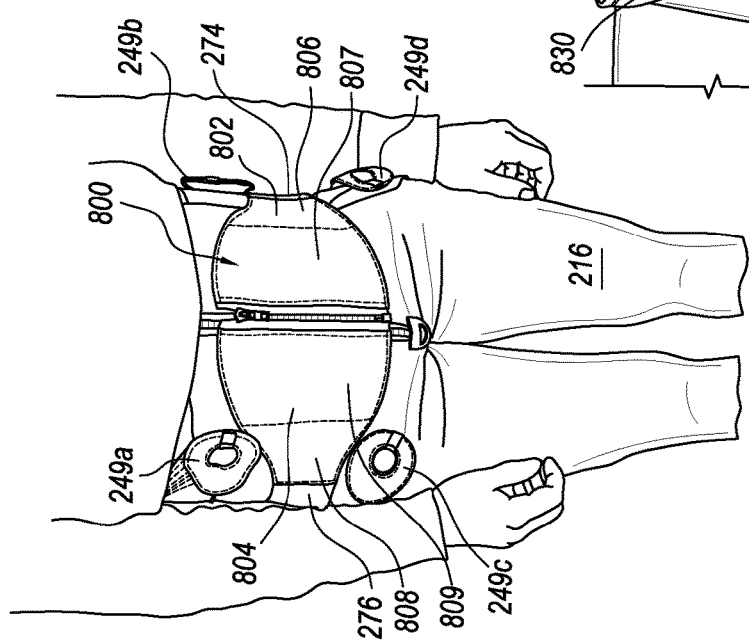
FIG. 15F is a schematic view of another closure system in the hip orthosis of FIG. 11A.

FIG. 15F illustrates another variation of a closure system 800 in which first and second panels 802, 804 secure to the first and second belt members 274, 276, as in the embodiment of FIG. 15C without the first and second clips. The first and second panels 802, 804 replace the first and second clips. Each of the first and second panels 804, includes a first section 806, 808 securing to the first and second belt members. The first section 806, 808 may comprise an alligator-type hook clamp or just comprise a single surface securing to an of the first and second belt members.

The first and second panels 802, 804 also include a second portion 807, 809 comprising mating zipper portions that form a zipper 810. The zipper 810 can be engaged and fully zipped to assure the belt members 274, 276 are secure about the user. Handles 249a-d may secure outside of the first and second panels 802, 804, or the first and second panels 802, 804 may have hook-receivable surfaces upon which the handles 249a-d may secure.

FIG. 15G shows another variation of a closure system 811. In this closure system 811, first and second belts 812, 814 are juxtaposed and secure to the first and second belt members 202, 204 via attachments 816, 820. The attachments 816, 820 may be permanently secured, as in being stitched to the belt members 202, 204, or removably secured such as by alligator-type clamps or other fastener means such as snaps, buckles, hook-and-loop, etc. Each of the attachments 816, 820 carries a buckle or D-ring 818, 822 upon which the belts 812, 814 are adjustably secured. While not shown, the first and second belts are adjustably secured to the first and second belt members 202, 204, and may be secured thereto by any of the fastener means described herein.

A user can easily remove the belts from the belt members to open up the closure system, and can likewise easily tension the belts to better secure the orthopedic device to the user. The handles 249 may be secured to the belts and the belt members, and the tensioning devices 214a, 214b may overlap the belts.

FIG. 15H depicts another variation of a closure system 823 including a fold portion 824 allowing for wrap panel 826 to extend thereover for quick adjustment of the garment 216. The wrap panel 826 includes a fastener 830 and the garment 216 has a receiving portion for the fastener 828 generally about the waistline of the garment 216 permitting the wrap panel 826 to secure over the fold portion 824. A user can easily adjust the girth and position of the wrap panel for donning and doffing the garment, and making adjustments as necessary during the course of wearing the garment.

Figure 13A:
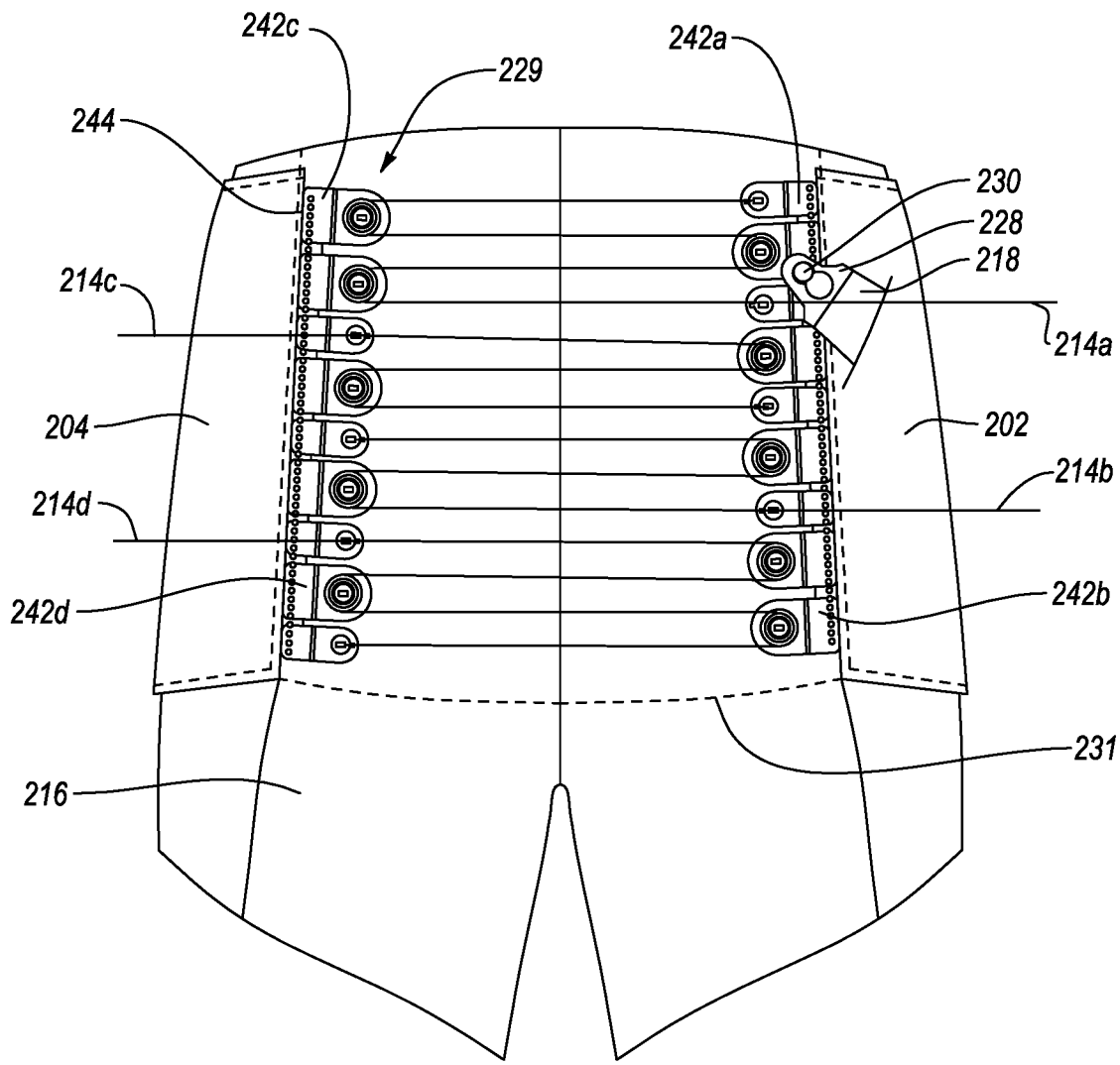
FIG. 13A is a detailed view showing a rear view of the compression system without a cover.
Figure 13B:
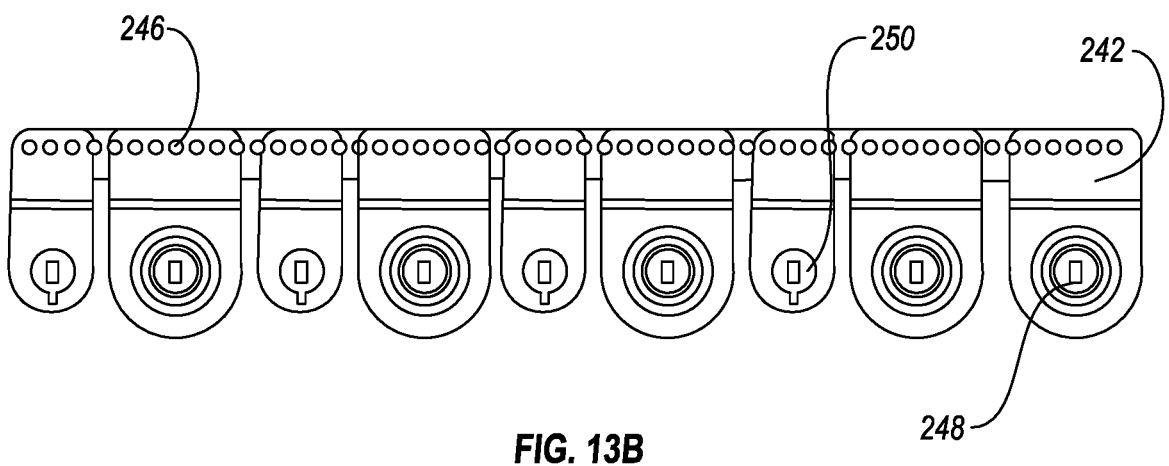
FIG. 13B is a detailed view of a set of pulleys in the compression system in the hip orthosis of FIG. 11A.

As shown in FIGS. 13A and 13B, the compression system 229 includes a plurality of tensioning sets such as those including pulleys 242A-242D corresponding to the tensioning devices 214A-214D. The pulley sets function in a manner similarly as the pulley sets described in U.S. Pat. No. 8,172,779, in that the pulley sets include pulleys 248 corresponding to each tensioning device 214A-214D, and anchors 250 for each tensioning device. A cover 231 may be provided to cover the compression system 229. The tensioning sets are not limited to using pulleys, but may include other means known to one skilled in the art such as using posts, bosses, or other elements by which a tensioning device, such as a cable or cord, may be biased to provide a mechanical advantage.

Figure 14A:
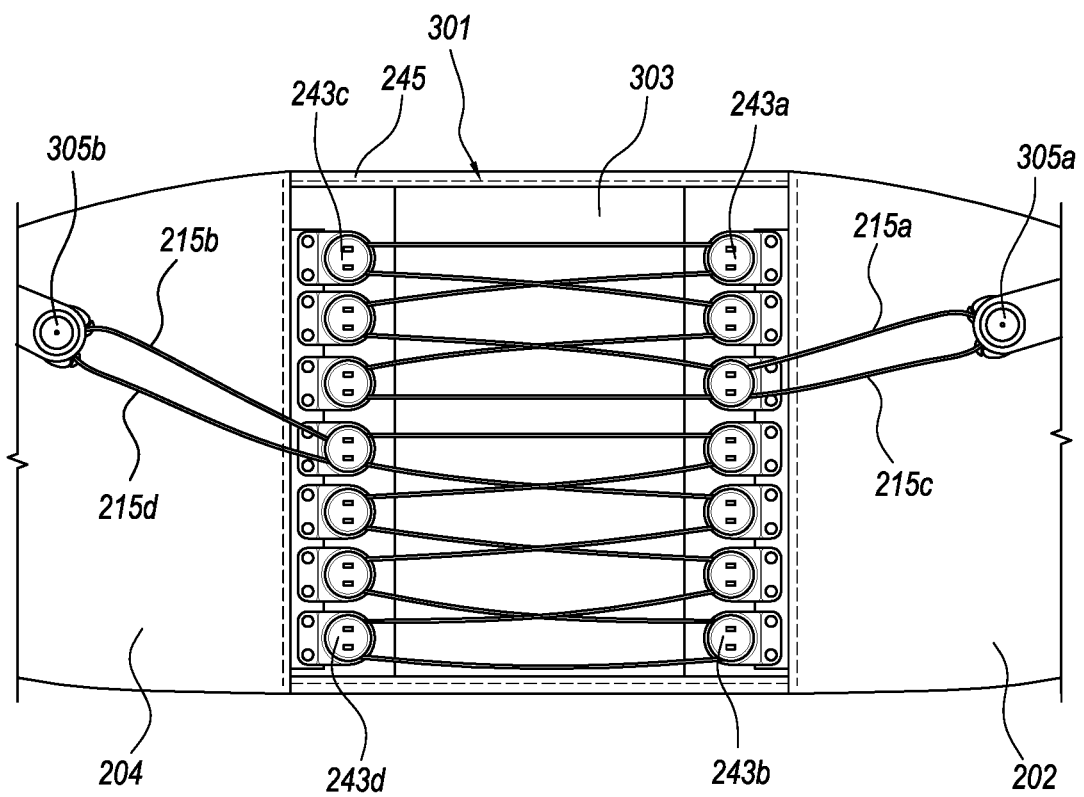
FIG. 14A is a detailed view showing a rear view of another compression system without a cover.

FIG. 14A displays an alternate embodiment of the compression system of FIGS. 13A and 13B. The compression system 301 includes a first group of tensioning sets 243a, 243c through which a first tensioning device 215a extends. A second group of tensioning sets 243b, 243d is located below the first group, and a second tensioning device 215b extends through the second group of tensioning sets 243b, 243d. While the first and second tensioning devices 215a, 215b are located on first and second sides of the posterior region of the first and second belt members 202, 204, they may be mounted on a same side, or alternatively replaced with a single group of tensioning sets.

The tensioning sets may be mounted on an inelastic segment 245 to anchor the compression system as the tensioning devices are tightened about a user. The inelastic segment isolates the tensioning sets from a remainder of the garment which may be generally elastic at least in part. The inelastic segment enables for better comfort and may protect the user from the tensioning sets inadvertently pinching the user. An elastic panel 303, which may be formed by the garment, is located between the first and second tensioning sets, and may expand and contract according to activation of the adjustment mechanisms 305a, 305b. The elastic panel may be formed with the entirety of the garment but distinguishable from the inelastic segments in which is it located in between.

Each of the first and second tensioning devices 215a, 215b engage first and second adjustment mechanisms 305a, 305b which may be mounted on the first and second belt members 202, 204. The adjustment mechanisms 305a, 305b may be permanently mounted to the belt members 202, 204, or they may be removably attached to the belt members 202, 204 at a plurality of locations to provide coarse adjustment of the tensioning devices. Finer adjustment of the adjustment mechanisms may be obtained once the adjustment mechanisms are mounted on the belt members.

The adjustment mechanism may be dial tensioning device provided by BOA Technology Inc., or an adjustment device described in U.S. Pat. No. 7,198,610, granted Apr. 7, 2007, and U.S. patent application publication no. 2009/0287128, published Nov. 19, 2009, which are incorporated herein by reference. Alternatively, the adjustment mechanism may be a linear ratchet as taught in U.S. patent application publication no. 2006/0135900, published Jun. 22, 2006, and incorporated herein by reference. Other adjustment mechanisms known to one having ordinary skill in the art may be used that provide locking unidirectional tensioning and release of an elongate element.

Figure 14B:
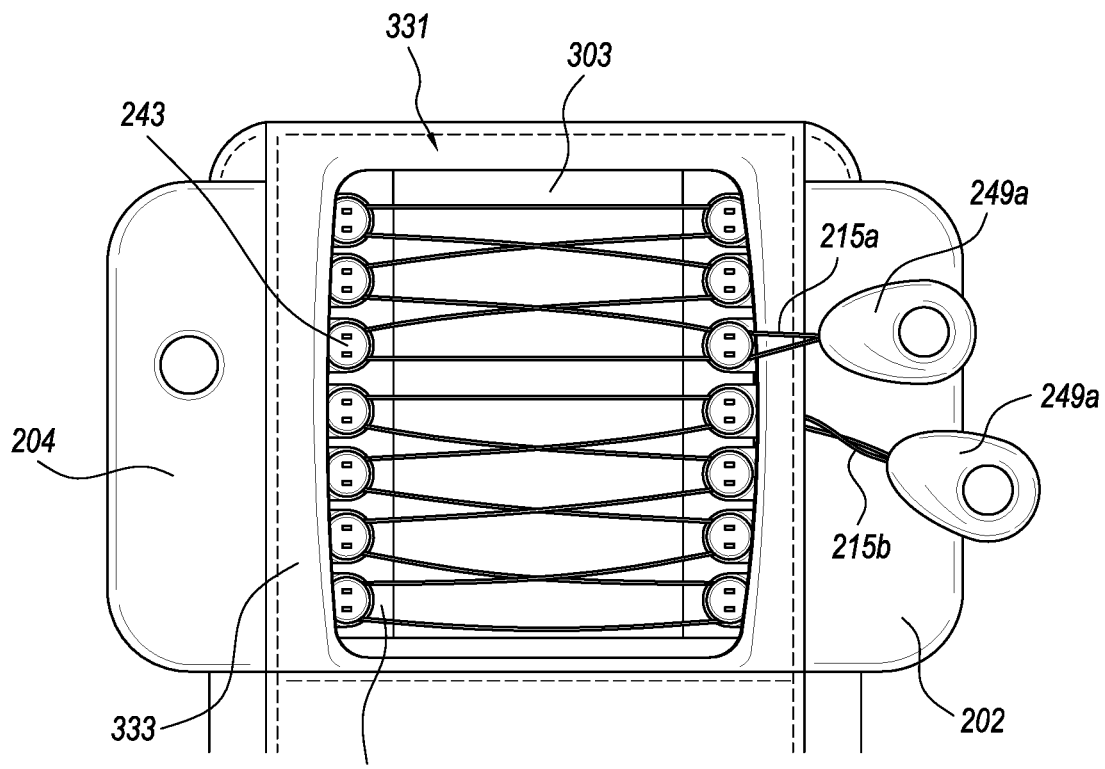
FIG. 14B is a detailed view showing a rear view of another compression system without a cover.

Referring to FIG. 14B, another embodiment of a compression system 331 is arranged similarly to the embodiment of FIG. 14A. The tensioning devices 215a, 215b generally extend from a single side of the compression system at the posterior region of the orthopedic device. The handles 249a, 249b mounted to the tensioning devices 215a, 215b may be secured over a surface of the belt members 202, 204 which preferably includes a hook receivable material whereas the handles 249a, 249b may bear a hook material. A back panel 333 may extend over the compression system 331 to protect it from damage or the tensioning devices being caught inadvertently on an object.

In both FIGS. 14A and 14B, the compression system does not involve termination points for the tensioning devices. The tensioning sets are preferably arranged in a zig-zag or alternate configuration and are therefore not configured in the straight across configuration of the embodiment of FIGS. 13A and 13B. While not shown, in any of the embodiments the tensioning elements may exit the cover from an opening formed near a first end of the belt members.

Either of the compression systems of FIGS. 14A and 14B, and other compression systems described herein may be modified so that the pulleys are tensioning sets are not alternate, but are opposite one another. The amount of tensioning sets may vary depending on the height of the compression system. The compression systems may or may not include termination points where one end of the tensioning device or cable secures and is at an end opposite a handle and/or adjustment mechanism.

For example, for a shorter or smaller compression system, a first end of the tensioning device secures to an anchor on a first side of the compression system. The tensioning device extends to a first pulley or tensioning set on a second side of the compression system, routing back to a second pulley on the first side back to a third pulley on the second side and out of the compression system with the handle at a second end of the tensioning device. The first and second pulleys may be opposite from one another or alternate relative to one another. For a taller or larger compression system, the tensioning device may extend through at least more pulleys than in the shorter compression system before the handle extends from the compression system.

The handle may be adapted to include a reel permitting the tensioning device to allow a portion of the tensioning device to be free and adjusted between two termination points. An example of such an arrangement may be modified according to U.S. patent application publication no. 2012/0204381, published Aug. 16, 2012, which is incorporated herein by reference.

In yet another variation, the orthopedic device may not include a compression system, but rather the posterior of the orthopedic device includes an elastic panel securing to opposed ends of the belt members. The elastic panel provides sufficient support and tensions over the posterior side of the user such that the orthopedic device is generally adjusted by the belt members without the need for tensioning devices.

Returning to the embodiment of FIG. 13A, as the first and second belt members 202, 204 may be stitched at their posterior ends to the garment 216 by the joint 244, the distance between the pulley sets 242A-242D is adjustable to provide tension on the pelvis. The stitching occurs along a plurality of openings 246 formed along a tab of the pulley sets such that the belt members extend toward the anterior side of the garment from the joint and the tensioning sets extend toward one another posteriorly from the joint. The belt members and the tensioning sets preferably are arranged to counteract one another.

An oblique band or exorotation strap 217 secures at one end to an anchor 230 protruding from the pulley sets. The upper belt members 202, 204 may each define an opening 236, 238 through which the exorotation strap 217 can secure so as not to interfere with operation of the belt members 202, 204, and the exorotation strap 217.

The exorotation strap 217 may include a tab 228 having means such as a keyhole to secure to the anchor 230. As with the embodiment of FIGS. 9A and 9B, the exorotation strap 217 defines a first segment 218 depending from the upper anchor 230 and couples to a second segment 232 by a tensioning device 220 and indicia sleeve 222 which provides incremental tensioning of the exorotation strap 217.

The exorotation strap may be arranged on the leg in different orientations depending on the desired rotation, internal or external. The strap is either taken between the legs and to the front of the thigh or directly to the front of the thigh or then fastened to a lower portion of the garment.

Figure 12:
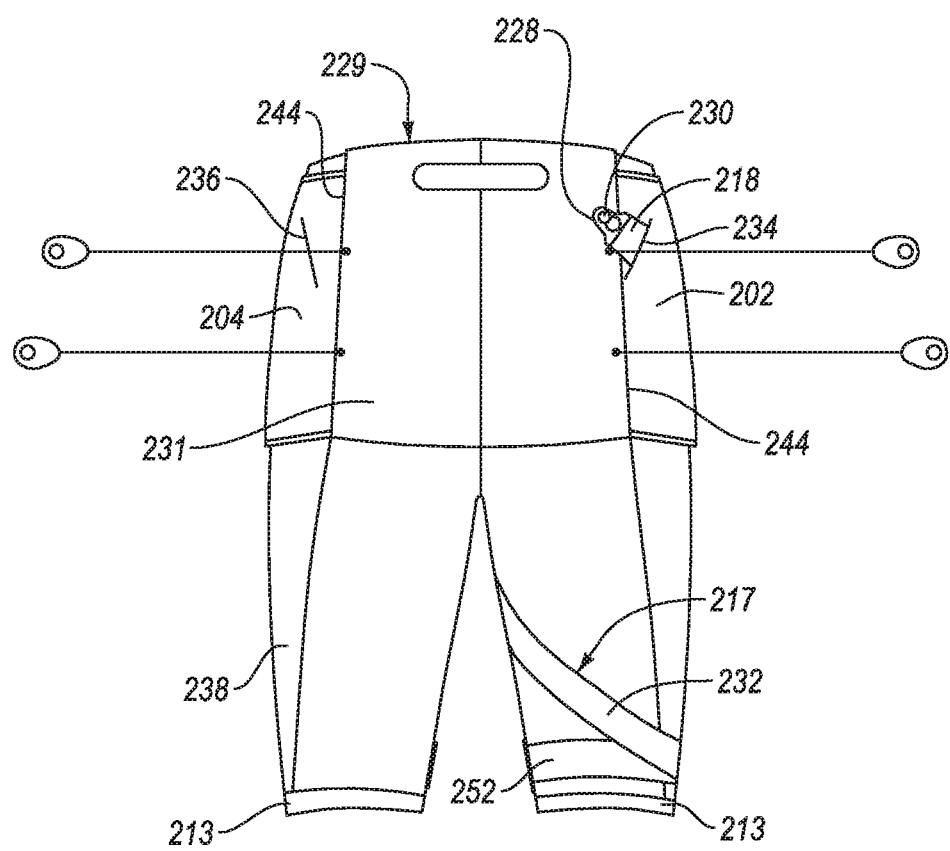
FIG. 12 is a rear view showing the hip orthosis of FIG. 11A.
Figure 16:
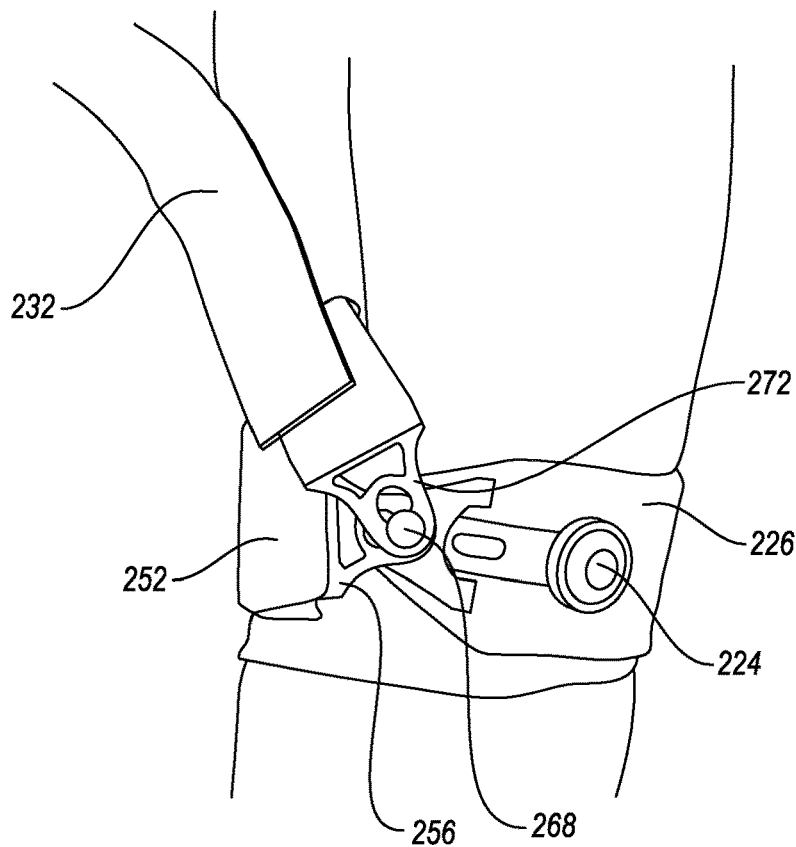
FIG. 16 is a detailed view of the lower support in the hip orthosis of FIG. 11A.

Referring to FIGS. 11A, 12 and 16, a lower tightening unit or wrap 226 includes a junction for receiving the second segment 232 of the exorotation strap 217 and carries a dial tensioning unit 224 for adjusting the tightness in the lower wrap 226. In the illustrated embodiment of FIG. 16, the lower wrap 226 has a strap 252 with opposed ends connected to locking elements or buckles 254, 256 enabling quick attachment to secure the lower wrap onto the leg. The locking elements 254, 256 may secure about the junction 227 with the second segment of the exorotation strap.

Figure 17:
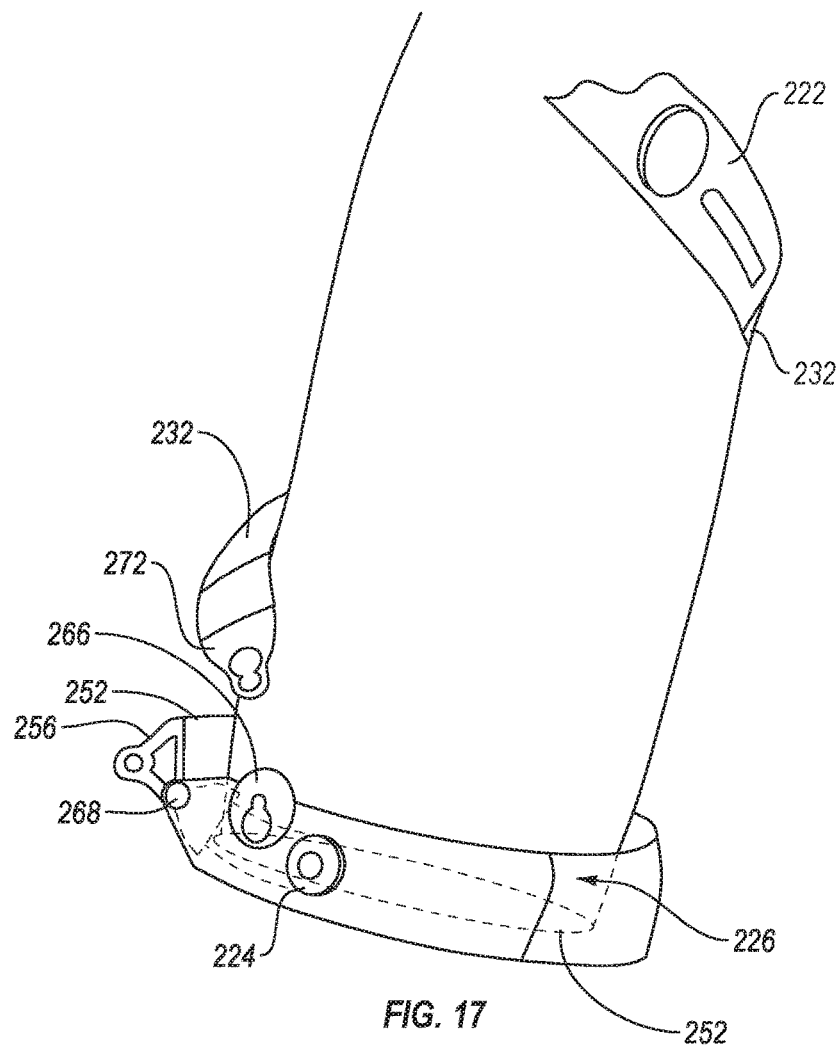
FIG. 17 is a schematic view of the lower support in FIG. 16 and attachment of straps.
Figure 18A:
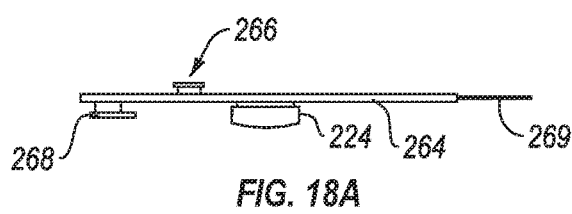
FIG. 18A is a plan view of a support element in the lower support of FIG. 17.

Referring to the embodiment of FIGS. 17 and 18A, the lower wrap 226 includes an elongate tab 264 carrying an anchor point 268. The anchor point 268 is used to secure to the locking element 256 carried by a second end of the strap 252, whereas the tab 264 connects to a first end of the strap 252. The tab 264 includes another anchor 266 extending along a rear portion of the tab and adapted to secure to a locking element 272 carried by the second segment 232 of the exorotation strap.

The tab 264 carries a dial tensioning device 224 coupled to a cable system 269 securing to the first end of the strap 252. The dial tensioning device 224 allows for fine adjustment of the tensioning of the strap 252.

The exorotation strap may be formed from an elastic or inelastic material. In the depicted embodiments, the exorotation strap is elastic. The exorotation strap is preferably trimmable in length at both ends for correct placement of the tensioning device over the user's leg. The exorotation strap may removably secure to the tensioning device 220 and the lower wrap 226 by means such as "alligator" type hook clamps and/or with keyhole connections. A pad may be on a body facing surface of the indicia sleeve 222 to provide for improved comfort.

The lower wrap strap 252 is preferably an elastic strap for improved comfort. Alternatively, the lower wrap strap may be inelastic or elastic, and formed from a loop material/foam material/loop material laminate.

Figure 18B:
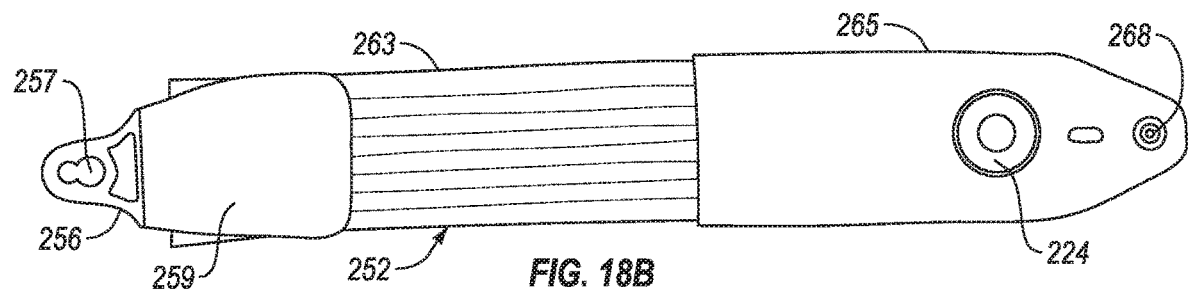
FIG. 18B is a front view of a strap of the lower support in FIG. 17.

FIG. 18B shows the strap 252 as having an elastic segment 263 with an inelastic segment 259 located at a first end carrying the locking element 256 with a keyhole 257. The strap 252 includes a sleeve 265 extending over a second end of the strap carrying the dial-tensioning device 224. The second end of the strap carries the anchor point 268, which is arranged to couple with the locking element 256 on the second end. The second end, by the dial tensioning device features or otherwise may be inelastic so the elasticity of the strap 252 is confined by the elastic segment 263, which provides comfort to the user. Of course other combinations of elastic and inelastic segments may be envisioned for the strap.

Figure 18C:
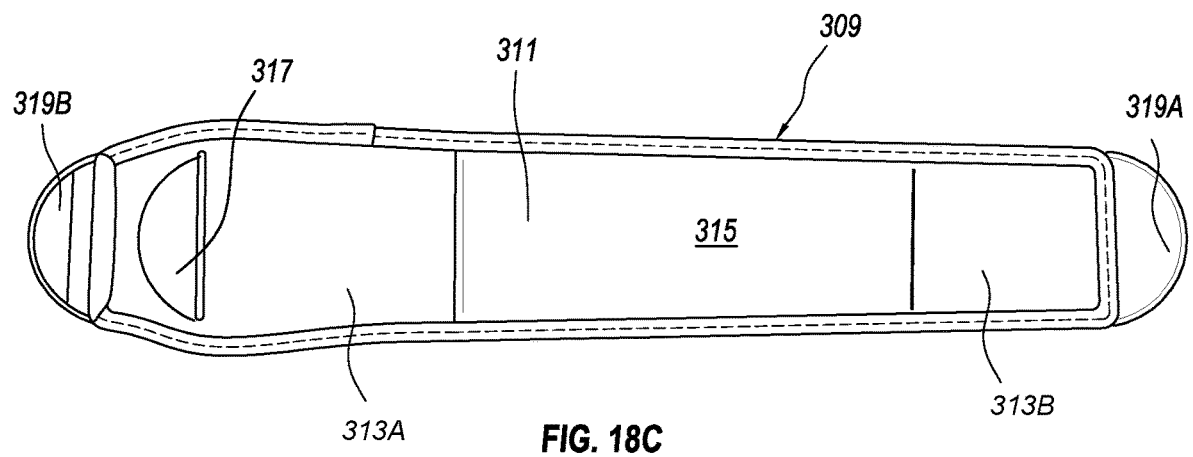
FIG. 18C is a front view of an alternate strap for the lower support in FIG. 17.
Figure 18D:
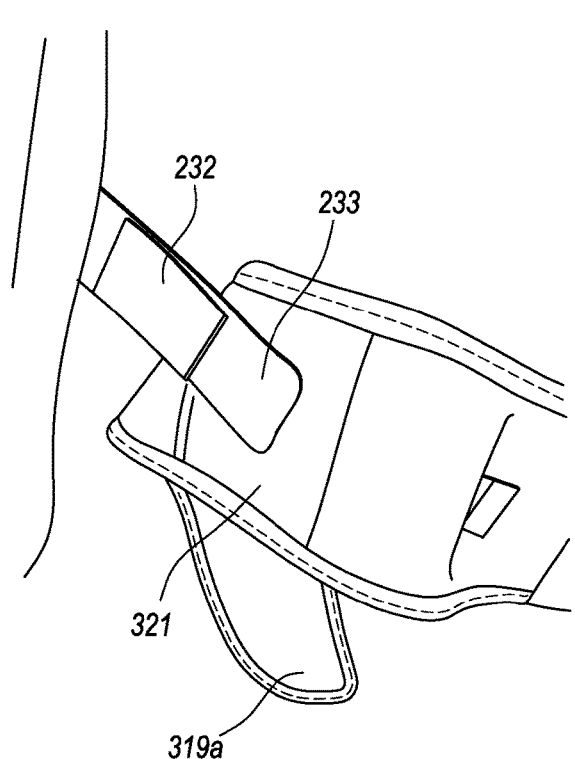
FIG. 18D is a schematic view showing attachment of an exorotation strap to the strap of FIG. 18C.
Figure 18E:
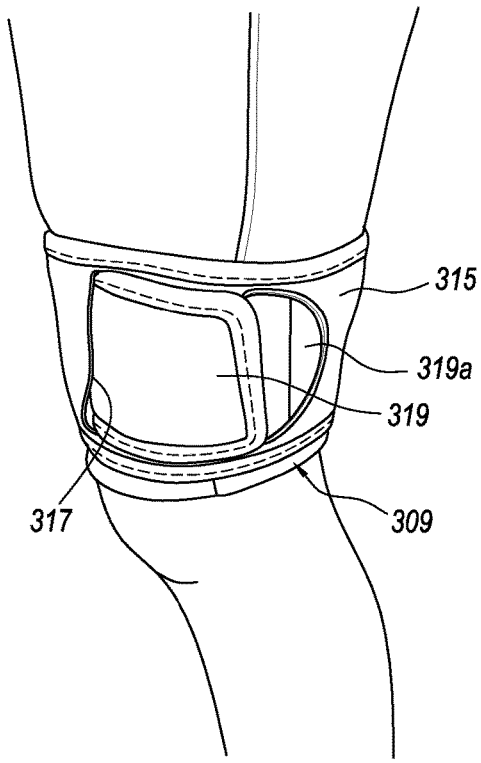
FIG. 18E is a schematic view showing the assembly of the strap in FIG. 18C.
Figure 22:
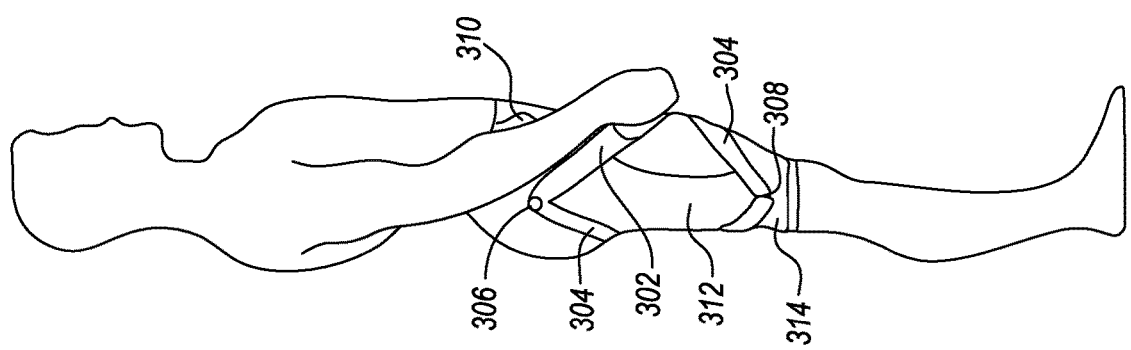
FIGS. 20-22 are rear, front and side views of the hip orthosis embodiment of FIG. 19.
Figure 21:
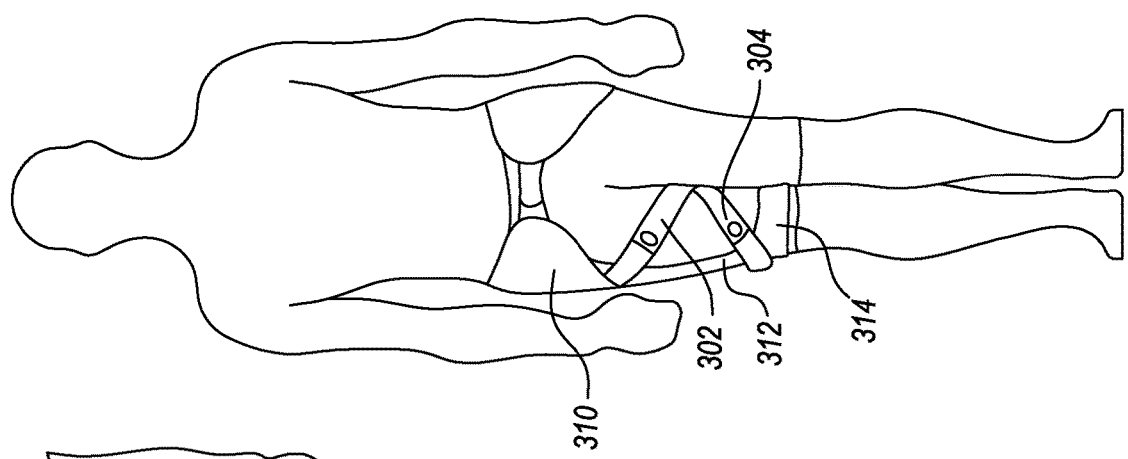
Figure 20:
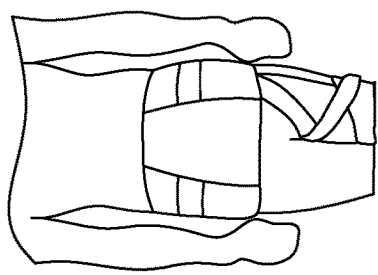
Figure 19:
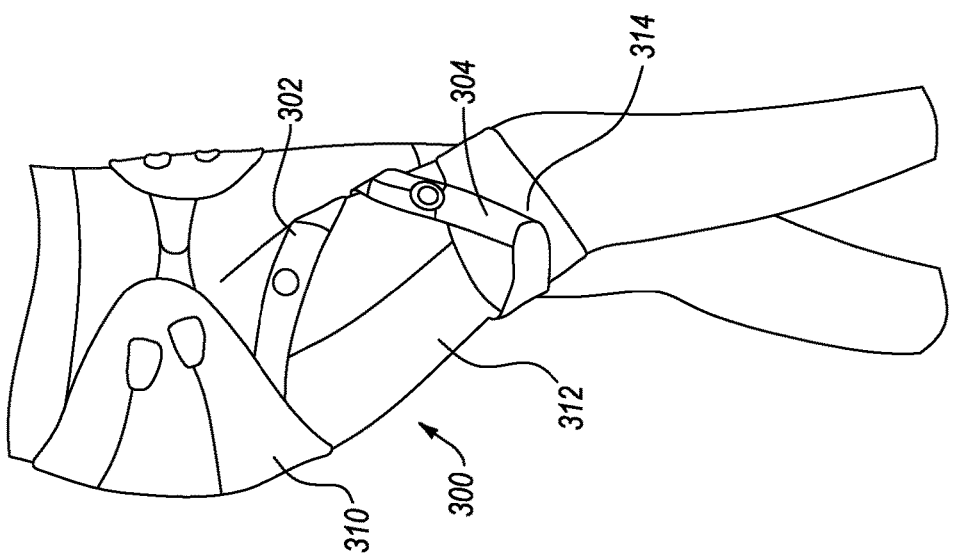
FIG. 19 is a perspective view of another hip orthosis embodiment according to the disclosure.

Referring to FIGS. 18C-18E, an alternate strap 309 for use in the lower wrap of FIG. 17 does not include any snaps, brackets or other hard elements. The strap 309 includes a first segment 311 that is elastic, a second segment 313A that secures to an end of the first segment and a third segment 313B secured to another end of the first segment; the second and third segments are generally inelastic. The first segment 311 generally has a hook receivable surface 315. First and second tabs 319a, 319b preferably secure to opposed ends of the strap 309 at the second and third segments 313A, 313B, respectively.

The second segment 313A defines an elongate slot 317 arranged for insertion of the first tab 319a through which the first tab 319a may extend and couple to the hook receivable surface 315. The first and second tabs 319a, 319b may include appropriate fastener material. An end 233 of the exorotation strap 232 may secure to a section 321 of the strap 309 preferably within the second segment due to its inelasticity.

Any of the orthopedic device embodiments may be provided with a plate system arranged for securing against at least the lumbar region and/or abdomen of the user. Various back plate systems useable with the orthopedic device embodiments may be found in U.S. Pat. No. 8,172,779. The difference from the lumbar-sacral orthosis in U.S. Pat. No. 8,172,729 is that the orthosis in such patent is arranged as a lumbar belt whereas the embodiments described herein are arranged for the hip and pelvis. The embodiments herein may be configured with at least a higher posterior portion to accommodate a plate system or have a connection for plate system to extend above the orthopedic device for placement against a lumbar region if the orthopedic device is configured for securing below such region.

For example, a back plate may slidably connect to the posterior portion of the orthopedic device. According to this embodiment, the back plate is flexible or bendable to accommodate the anatomy of a wearer's back when the closure system is employed. The ability to bend about the wearer's back is particularly advantageous since the back plate can be used to support a variety of anatomical contours of a single wearer or a variety of wearers. However, while the back plate is bendable about the wearer's back, it provides sufficient rigidity to support the lumbo-sacral region of the wearer. In an alternative, the back plate may be custom formed so as to correspond to exact contours of a particular wearer wherein the back plate is substantially rigid or semi-rigid.

The back plate of the plate system may have a particular anatomical geometry that is arranged to closely accommodate a wide variety of different back anatomies. For example, the plate may be configured to relieve pressure over a spinal region of a human back by having an outwardly directed curvature generally protruding away from the spinal region. The plate may be arranged to apply even pressure over a paraspinal musculature of a human back by having an inwardly directed contour extending over the paraspinal musculature. The plate may include side wing portions which are inwardly contoured toward the wearer, a tapered top portion and generally rounded side portions, which provide coverage over side portions of the lumbar region of a wearer's back, and contribute to better pressure distribution over sensitive and less sensitive areas of a wearer's back.

The plate may define a general arcuate contour providing lordosis support for the wearer. This contour, in combination with pressure exerted on the plate via the closure system, introduces and maintains correct lumbar lordosis for pain relief, spinal stabilization and improved posture, such for decreasing lordosis and increasing pelvic tilt. Because the plate is anatomically contoured with the aforementioned features, better hydrostatic lift is also created when the abdominal cavity is gently compressed and the intra-abdominal pressure is increased.

As discussed in U.S. Pat. No. 8,172,729, the anatomical shape of the plate creates better pelvic stabilization since it is arranged to properly align the pelvis in relation to the spine, thereby reducing pain in the lumbo-sacral region of a wearer's back. Again, in combination with closure system, the plate allows for improved immobilization of a wearer's back by immobilizing flexion, extension, pelvic tilt, spinal rotation and lateral bending.

Referring to FIGS. 19-22, a hip orthosis 300 embodiments is shown wherein exorotational straps 302, 304 are arranged in a neutral configuration to keep the hip in neutral position and to restrict both internal and external rotation. Both upper ends of the exorotational straps 302, 304 are secured to an upper anchor point 306 on the compression system and to a lower anchor point 308 on the lower wrap 314.

FIGS. 19-22 exemplify how the exorotational straps 302, 304 may be anchored to the belt member 310 with a tensioning system and the lower wrap 314 without the necessity of a garment, as described in various embodiments herein. The upper and lower wraps 310, 314 may be connected with an elongate lateral segment 312 which may include a strut assembly.

Figure 23:
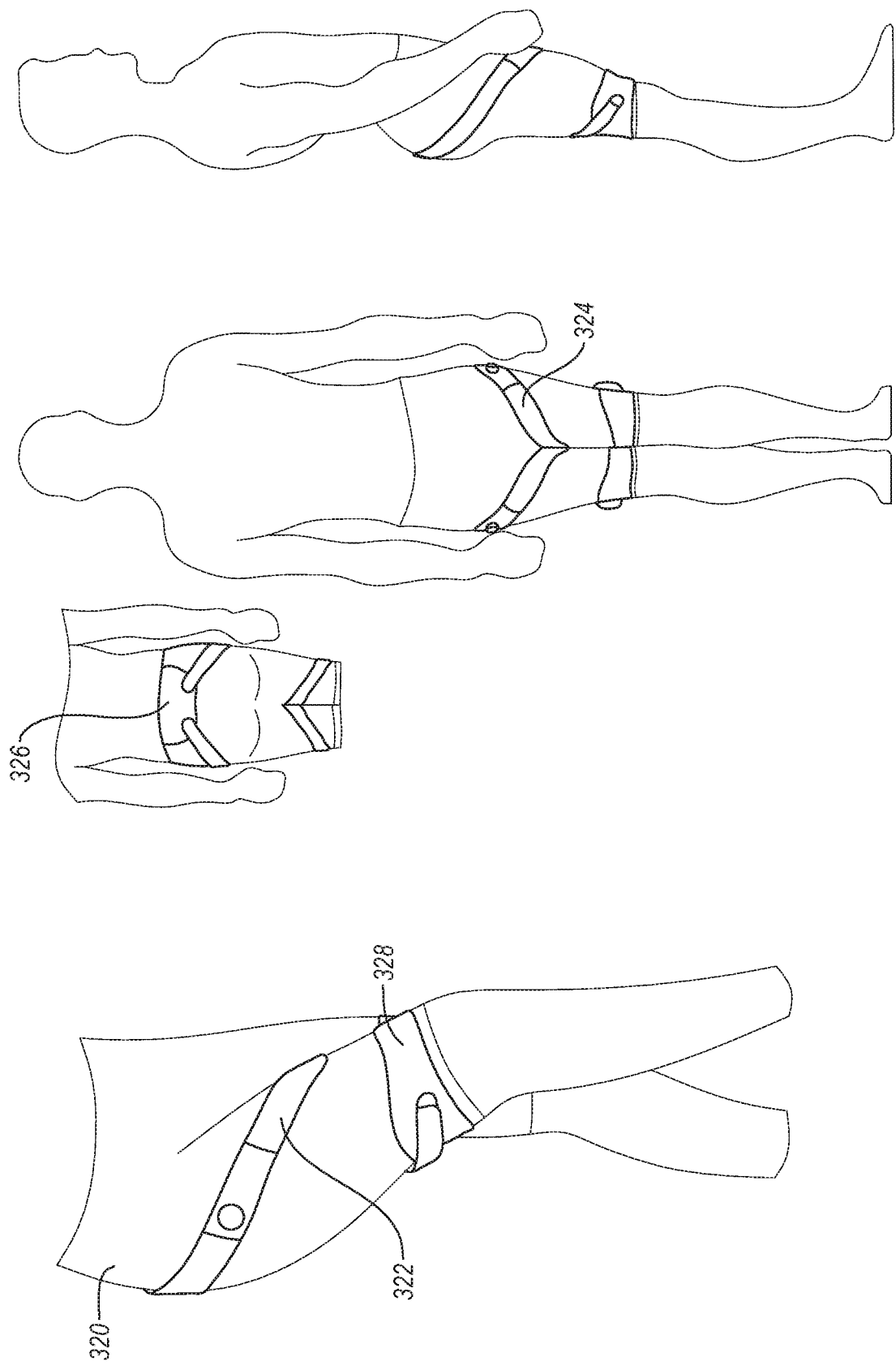
FIG. 23 exemplifies views of another hip orthosis embodiment according to the disclosure.

FIG. 23 shows an embodiment without a belt member, rather the embodiment includes a garment 320 on which the exorotation strap 322, 324 secures to a posterior portion or panel 326 and a lower wrap 328 of the embodiments described herein. In this embodiment, exorotation straps are on both legs for stabilization of both hips.

FIG. 24 exemplifies an embodiment in which the strap provides derotational strapping in the hip. In the configuration in FIG. 24, there is minimal rotation, minimal abduction and little or no flexion resistance or assistance. The strap 340 includes a lower wrap 342 having portions that may extend above and below the knee to anchor the strap 340. A rotational strap 344 extends from the medial side of the lower wrap and spirals along the medial leg and over the buttocks to an upper belt member 346 at about a frontal or anterior portion of the hip generally between the lateral and medial sides.

Figure 25:
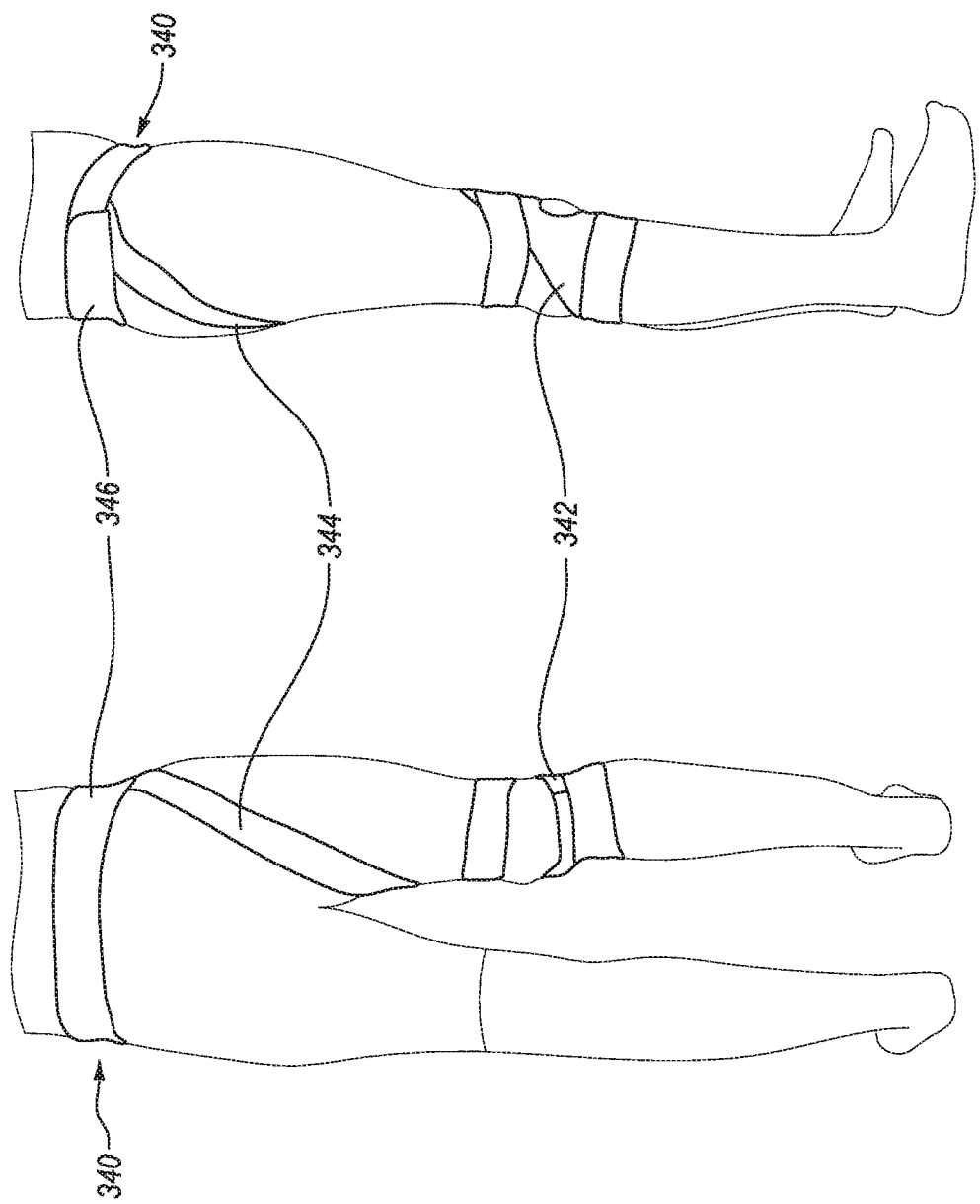
FIG. 25 includes schematic views showing another hip orthosis embodiment arranged for derotational strapping in a hip.

FIG. 25 offers another configuration of the strap 340 including the lower wrap 342 and the rotational strap 344 in the embodiment of FIG. 24. Similarly to the embodiment of FIG. 24, the rotational strap 344 extends from the medial side of the lower wrap 342 and spirals along the medial leg and over the buttocks. Unlike in the configuration of FIG. 24, the rotational strap 344 is secured to a lateral side of the upper belt member 346. In this configuration, there is internal rotational and abduction control, and flexion and resistance and extension assistance.

Figure 26:
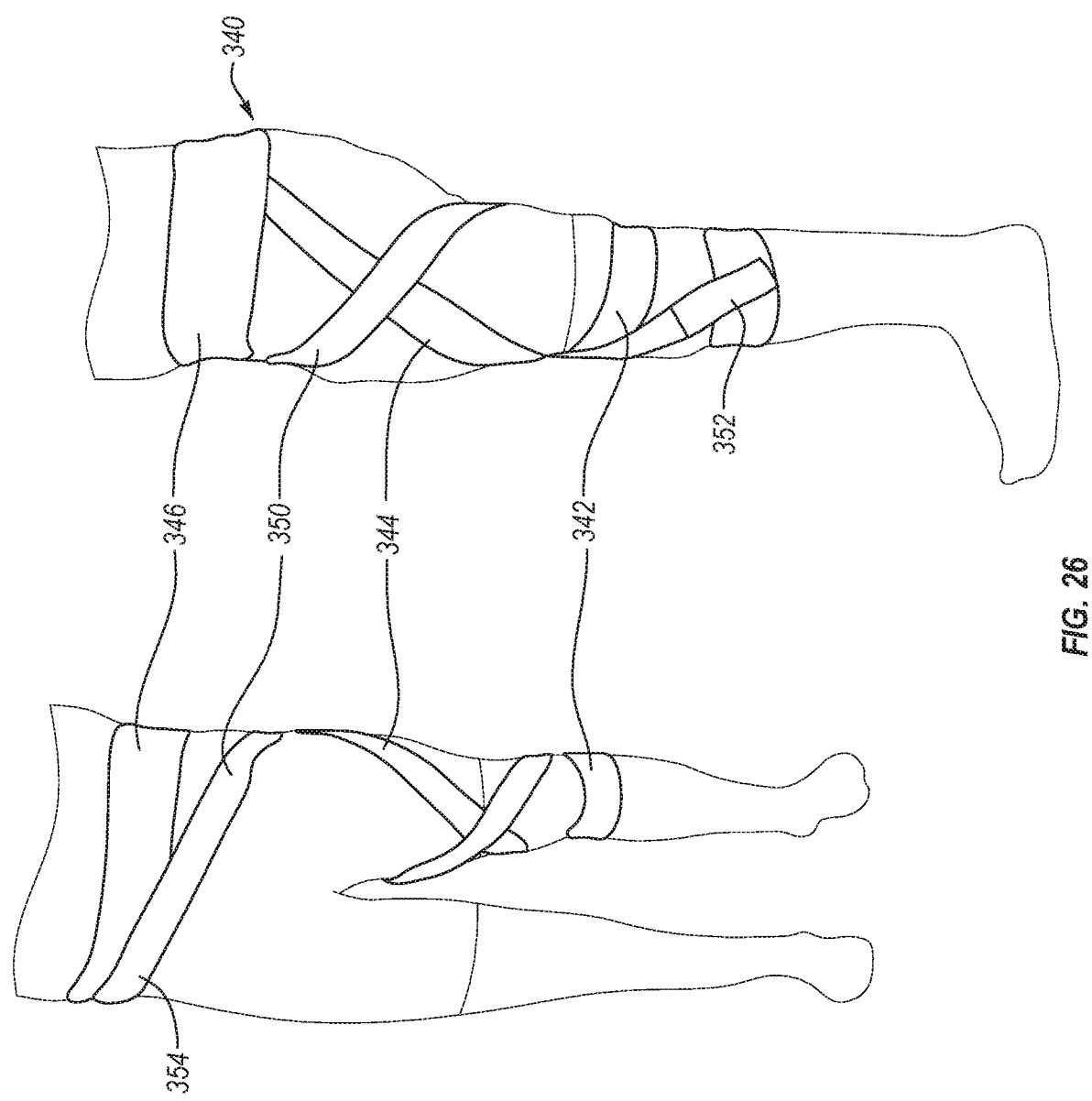
FIG. 26 includes schematic views showing another hip orthosis embodiment arrangement for rotational strapping in a hip.

Referring to the embodiment of FIG. 26, a variation of the hip orthosis of FIGS. 10A-10B or FIGS. 24-25 is employed in combination with a derotational strap 350. The derotational strap 350 secured to the lower wrap 342. In this configuration, the rotational strap 344 is arranged to extend from the medial side of the lower wrap 342, over the anterior thigh and secures to the lateral side or lateral-posterior side of the upper belt member 346.

Besides the rotational strap 344, the derotational strap 350 extends from a lateral side of the lower wrap 342 whereat a lower end 352 secures to the lower wrap 342, crossing over the rotational strap as it is directed toward the medial side of the thigh, about the lateral waist and securing to the upper belt member 346 and secured to a plurality locations on the upper belt member. As shown, the derotational strap 350 has an upper end 354 securing over the hip above the other leg. According to this configuration, the hip orthosis provides internal and external rotation control.

FIGS. 27 and 28 exemplify a strut assembly 360 for use with the hip orthosis for connection to the upper and lower wraps in the embodiments disclosed herein. The frame 360 includes a strut 362 extending between an upper frame 364 and a lower connection 368 to the lower wrap 226. The lower connection 368 may secure to the lower wrap 226 to an anchor such as the anchor 266 disclosed with the embodiment of FIGS. 17 and 18 whereby a pin or button 374 secures within a slot 368 defined by the lower connection.

The strut 362 has a pivot point 366 within upper frame 364, and the upper end of the strut 362 can slidably engage within a recess or area 370 defined within the upper frame 364 to accommodate movement of the user. The strut 362 may be rigid or substantially rigid to provide for additional thigh support. As shown in FIG. 9A, the strut 362 may carry a trochanter pad to urge against the trochanter.

The frame 360 may be configured to be attachable and detachable to the hip orthosis embodiments described herein. The garment may include pockets to receive the upper frame, or the upper frame may be attached by hook and loop fasteners. The upper frame may be flexible to accommodate the shape of the hip of the user. The strut may reduce or prevent adduction and provides more rigidity to the orthosis to avoid the risk of dislocation.

FIG. 29 shows an embodiment of a length adjustment assembly for the tensioning device or cable 400. The handle 402 is flexible and defines a pocket 408. The embodiment includes a retainer 404 arranged for wrapping excess or an undesired length 406 of the cable 400 thereabout. The retainer 404 may include grooves or channels 410 arranged to hold the cable 400. The pocket 408 is sized and configured to accommodate the retainer 404 and excess length 406.

The embodiments of FIGS. 30-35 are directed to an embodiment of a hip orthosis arranged to maintain an upper leg positioned correctly regarding a trunk during use.

Figure 30:
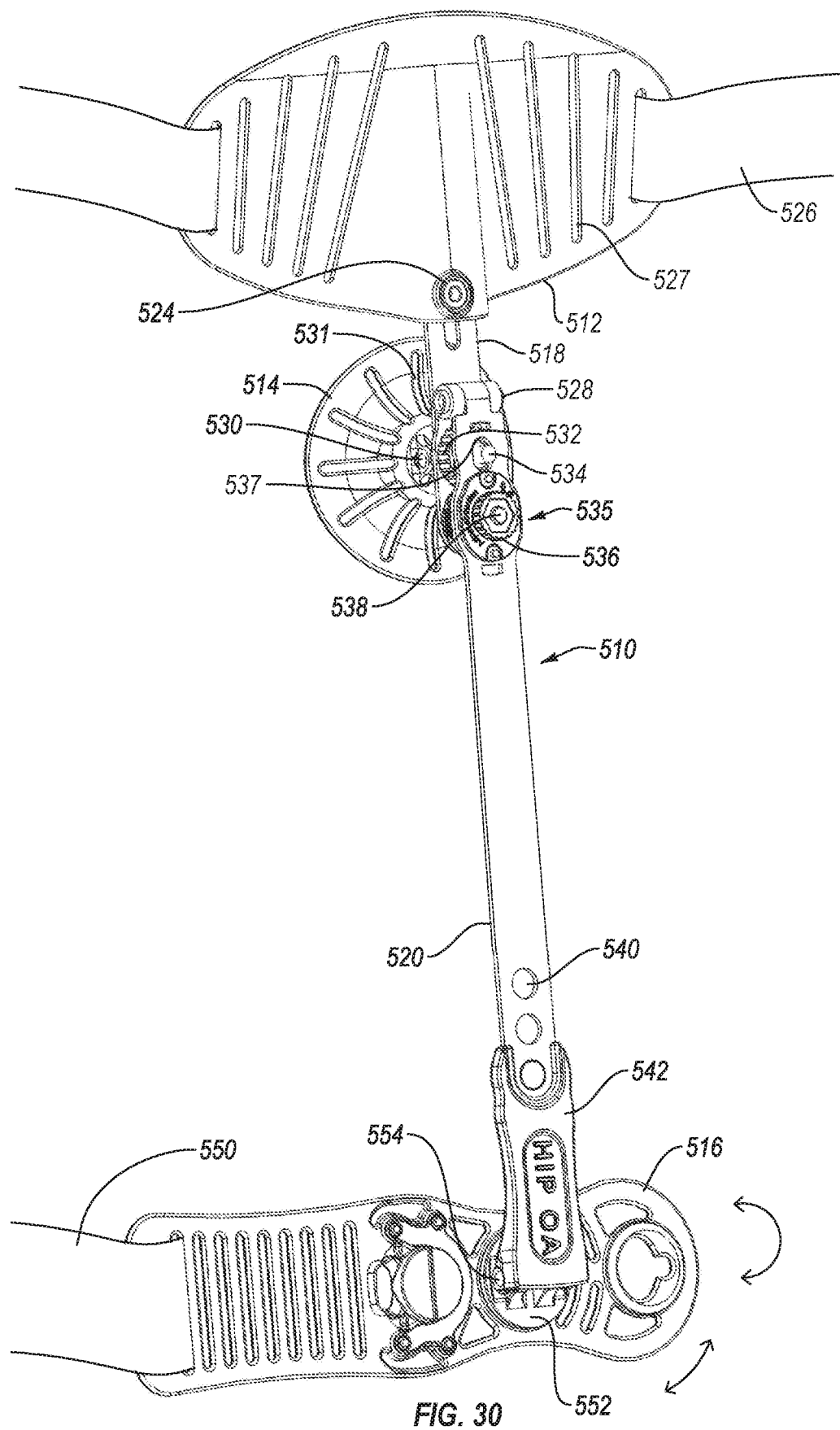
FIG. 30 is a perspective of an embodiment of a hip orthosis according to the disclosure.

In reference to the embodiment of FIG. 30, the hip orthosis 510 includes a pelvic support 512, a trochanter support 514 and a lower support 516. The pelvic support 512 is arranged for placement at or near the pelvis of the wearer, whereas the trochanter support 514 is arranged for placement at or near the trochanter of the femur opposite the femoral head. The lower support 516 is preferably arranged near and above the knee of the wearer. The pelvic, trochanter and lower supports 512, 514, 516 are connected to one another by a strut assembly comprising at least upper and lower struts 518, 520.

The strut assembly comprises a leaf spring from, for instance, metal or plastic. Due to the resiliency of the strut assembly, the hip orthosis can exert a force and/or a moment on the upper leg, which makes the upper leg abduct, viewed from the front side of the person, preferably independently of the position of the upper leg regarding the waist or trunk. The wearer has more freedom of movement, since the upper leg can preferably move in all directions.

The upper strut 518 has a first end slidably connected to the pelvic support 512 by a slot formed by the upper strut 518 and a fastener 524 extending through and securing against the pelvic support 512 and the upper strut 518. By loosening the fastener 524 from the pelvic support 512, the pelvic support 512 can be slidably adjusted along the length of the upper strut 518 to accommodate the wearer's size. At least one strap 526 secures through slots 527 formed along the pelvic support, and is sized and configured to extend around the trunk, waist or pelvis of the wearer to anchor the hip orthosis at an upper end of the wearer's leg.

Figure 31A:
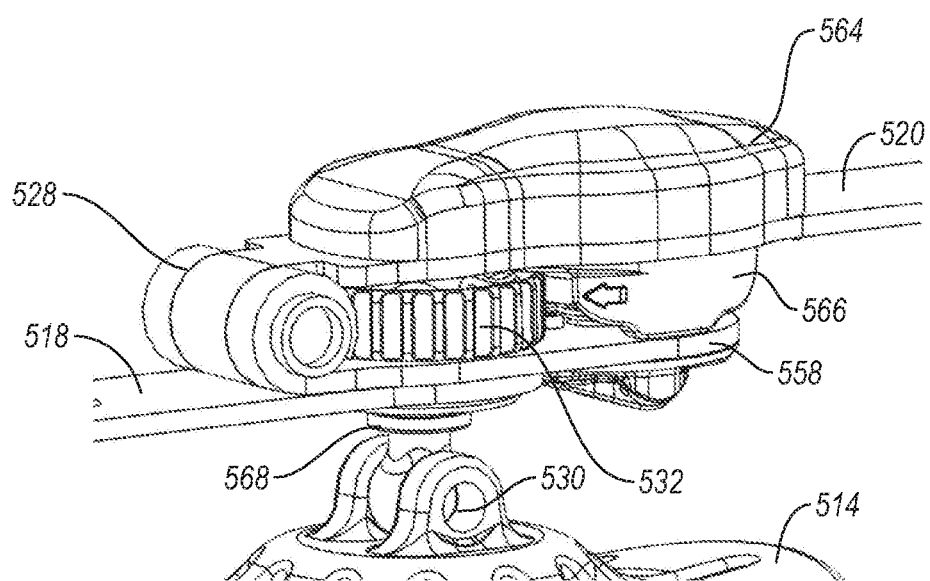
FIG. 31A is a perspective view of an adjustment assembly of the hip orthosis according to FIG. 30.
Figure 31B:
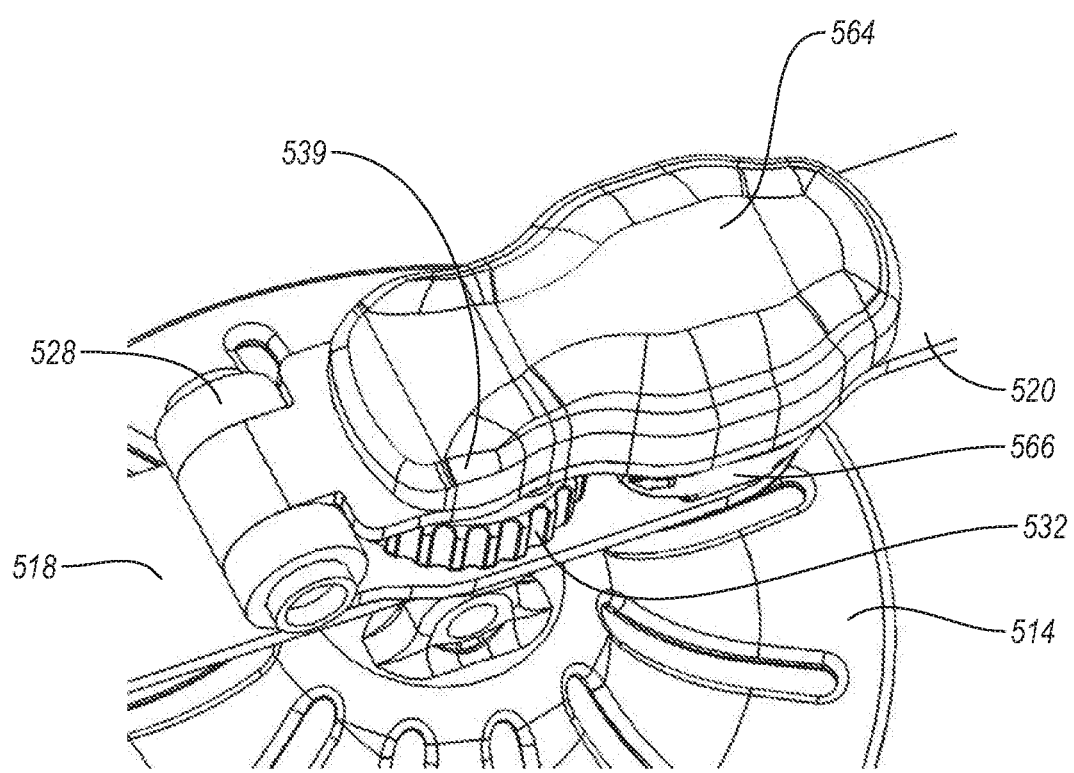
FIG. 31B is another perspective view of the adjustment assembly of the hip orthosis according to FIG. 30.
Figure 32:
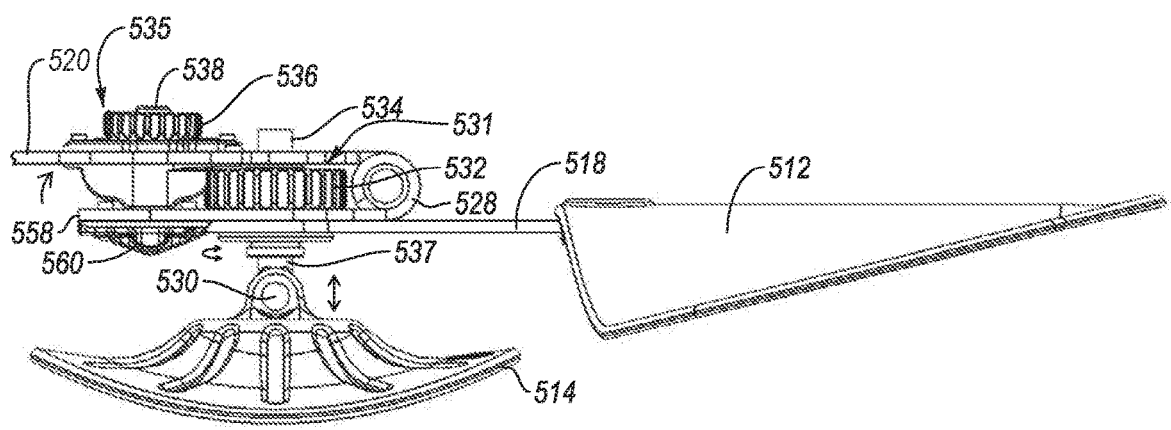
FIG. 32 is a detailed sectional side view showing an upper portion of the hip orthosis according to FIG. 30.

In referring to FIGS. 31A-32, a second end of the upper strut 518 is pivotally connected to a first end of the lower strut 520 by a hinge 528. The hinge 528 has a plate 558 secured to an outer surface of the upper strut 518 and permits the lower strut 520 to pivot away from the outer surface of the upper strut 518. Both the upper and lower struts are preferably resilient bars or plates, and are flexible and resilient so they return to a predetermined shape after they are bent.

A strut adjustment or pivot mechanism 535 is secured to the second end of the upper strut 518, and to the first end of the lower strut 520. The pivot mechanism 535 includes a dial 536 and a pin 538 connected to the dial 536. A first end of the pin 538 is coupled to the upper strut 518 by a pin mount 560, and a second end extends through an opening formed through the lower strut 520 to engage the dial 536 that rests upon an outer surface of the lower strut 520. A cover plate 566 may be included to cover at least part of the pin 538 located between the upper and lower struts 518, 520.

Figure 33:
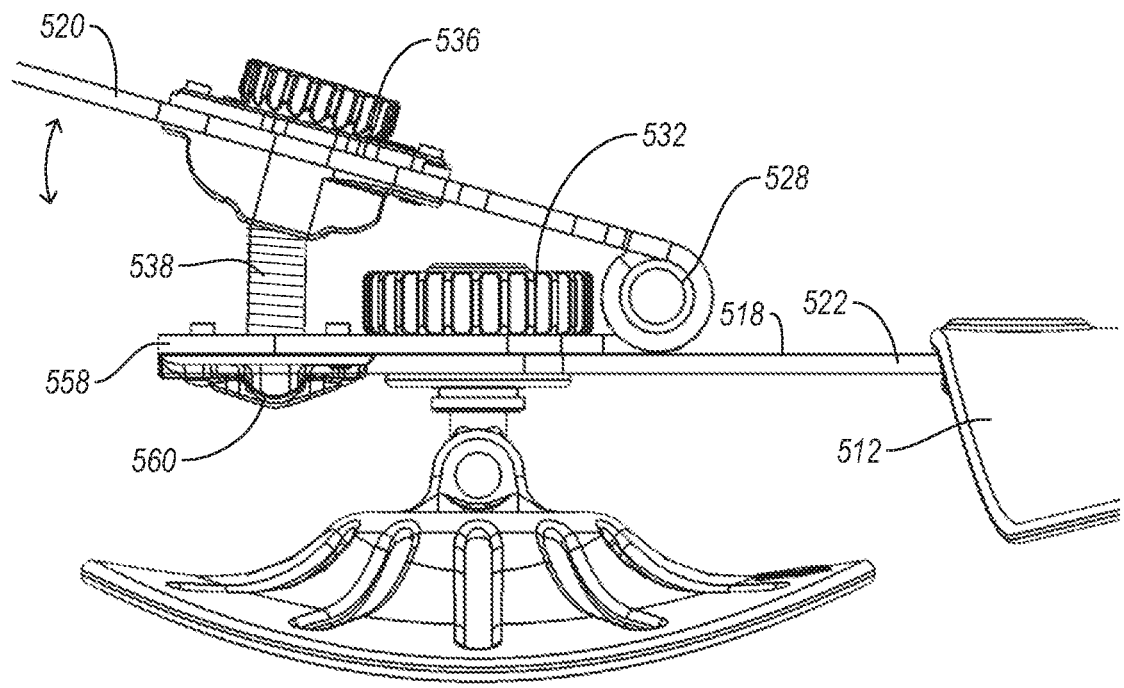
FIG. 33 is a detailed view showing adjustment of the pivot adjustment mechanism in the hip orthosis according to FIG. 30.

FIG. 33 depicts rotation of the dial 536 that urges the pivoting of the lower strut 520 relative to the lower strut 518. This arrangement is advantageous in that the wearer can adjust the force exerted by the strut assembly on the trochanter via the trochanter support 514 to urge the femoral head into the hip socket. The dial 536 may include indicia, which would allow the wearer to have an understanding how much force to exert onto the hip joint.

The wearer may in an initial fitting set the lower strut 520 so it pivots significantly away from the upper strut 518, and then rotate the dial so the lower strut 520 is drawn toward the upper strut 518 to exert more pressure on the trochanter. The dial may be coupled to a gear system that provides mechanical advantage to enable easier adjustment and locking of the dial as it is adjusted.

The trochanter support 514 is pivotally and rotatably secured to the inner surface of the upper strut 518 by a swivel 568 and hinge 530. This arrangement permits the trochanter support 514 to adjust to the specific anatomy of the wearer and to adapt to movement of the wearer's leg.

A pressure adjustment mechanism 531 is secured to the upper strut 518 and preferably located between the pin 538 and the hinge 528. The pressure mechanism 531 is adapted to urge linear movement of the trochanter support 514 relative to the inner surface of the upper strut 518.

The pressure mechanism 531 includes a dial 532 and a pin 534. The dial 532 is on the outer surface of the upper strut 518, and the pin 534 extends between the dial 532 and a pin mount 537 on or part of the swivel 568. The lower strut 520 may include a slot 539 enabling the pin 534 at least partly through when the trochanter support 514 is fully drawn toward the upper strut 518.

Figure 34:
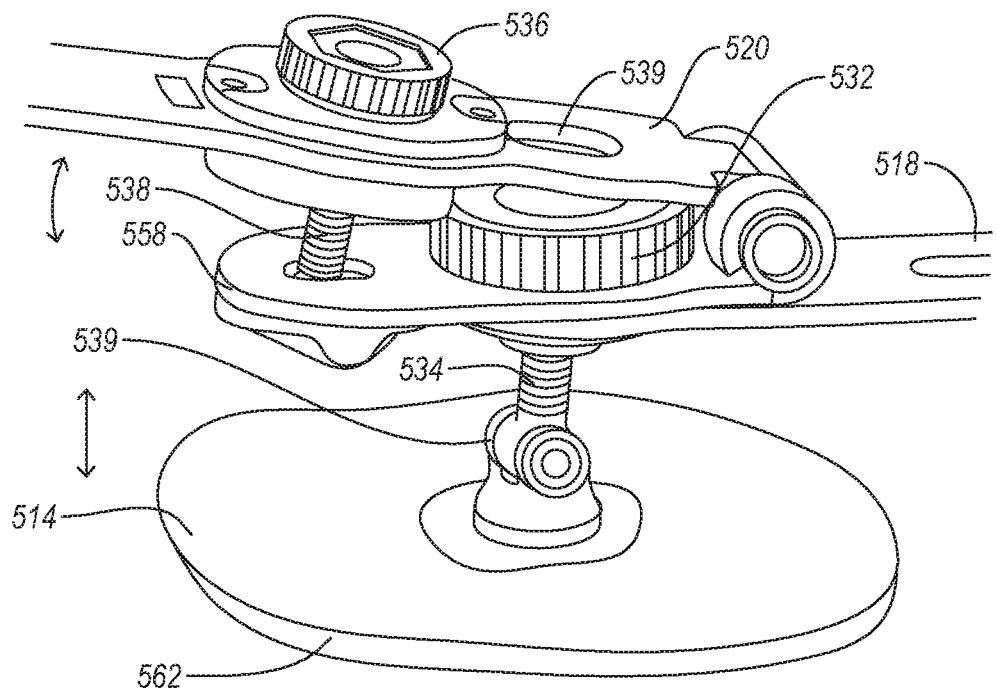
FIG. 34 is a detailed view showing adjustment of the pressure adjustment mechanism in the hip orthosis according to FIG. 30.

As shown in FIG. 34, rotation of the dial 532 causes the trochanter support 514 to linearly travel relative to the inner surface of the upper strut 518. This allows for fine adjustment of the pressure of the trochanter support 514 without further adjusting the upper and lower struts 518, 520 relative to one another. The trochanter support 514 may include padding 562 to provide more compression as the trochanter support 514 is adjusted against the wearer.

A cover 564 is used to cover both portions of the pressure mechanism 531 and the pivot mechanism 535 when they are not being used for adjustment. Portions of the dial 536 may be exposed from the cover 564 for quick adjustment of the trochanter support 514, whereas the pivot mechanism 535 is concealed.

Figure 35:
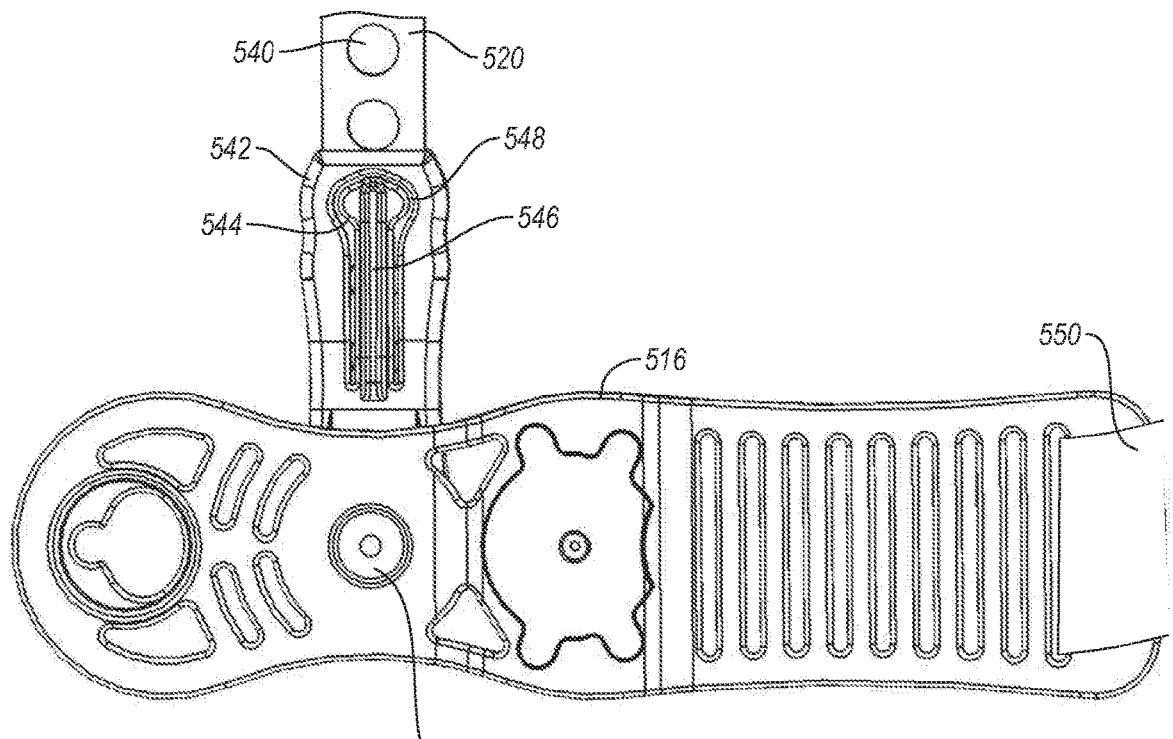
FIG. 35 is a detailed sectional rear view showing a lower portion of the hip orthosis according to FIG. 30.

Referring to FIG. 35, the lower support 516 is adjustably secured to the lower strut 520 by a sleeve 542 engaging one of apertures 540 formed by the lower support 516. The apertures 540 are formed along the length of the lower strut 520, and the sleeve 542 defines an adjustment device 544 that engages one of the apertures 540. The adjustment device 544 includes a flexible tab 546 having a head 548 biased toward the lower strut to flexibly engage one of the apertures 540. The adjustment device 544 allows for sliding the lower support 516 along the second end of the lower strut 520 to adjust the position of the lower support 516 to the length of the wearer's leg.

The lower support 516 is rotatably and pivotally adjustably secured to the sleeve 542. A pivot mount secures to the lower support 516 by a pivot pin 556 and a hinge attaches to the lower support 516 via the pivot mount. A strap 550 secures to the lower support 516 to circumferentially secure to the lower leg of the wearer.

In any of the embodiments described, they may include means to allow for quick removal of the garment if the user desires its removal, such as using a restroom. A zipper may be provided to enable opening the opening of the garment to facilitate removal or as an opening for male users.

The garment may include various sections including silicone on the inner surface to resist movement of the garment on the body of the user. These sections may include the waist portion of the garment and at the lower portion over the thigh. When added with the tension from the tensioning system, the silicone and the tension of the garment tightly secures the garment to the body of the user.

The garment may be used in combination with various means for therapy including cold or hot therapy, such as at the trochanter pad, or various forms of electrotherapy including NMES, TENS, PEW and heat therapy.

The embodiments described provide compression, skin protection, sealing, load transfer (compression/rotation), and reduction in pelvis drop and stability. The garment provides compression for those users having superior or lateral osteoarthritis of the hip. Compression at the hip by applying force to the femoral head moves the point of contact, or may be placing a counter force on to the femur to reduce the load on the hip socket. Compression of the pelvis may also assist hip muscles to relax and reduce muscle pain.

Sealing of the labrum is helpful by placing pressure on the greater trochanter by the trochanter pad and assisting the labrum to seal the internal pressure of the joint. The main function of the acetabular labrum improves hip joint stability by deepening the hip socket by providing it with extra structural support, and partially sealing the joint to create a negative intra-articular pressure which contracts any distractive or pulling-apart forces. The second function of the acetabular labrum increases joint congruity. By placing pressure on the labrum, the femoral head may get pulled into the socket and moved away from the affected osteoarthritis area of the joint.

The exorotation strap may provide pain relief when the hip joint is externally rotated. By rotating the femoral head, either internally or externally, sealing of the labrum may occur. Correcting the posture of the muscles placed in a more normal position may assist reduction of pelvis drop and reduce muscle pain. By stabilizing the hip, pain may be reduced since it is placed in a more correct position. Various embodiments of the garment may be formed from a slippery elastic material, such as a spandex, which assists in compressing against the body of the user and reduces the possibility of irritation.

Figure 36:
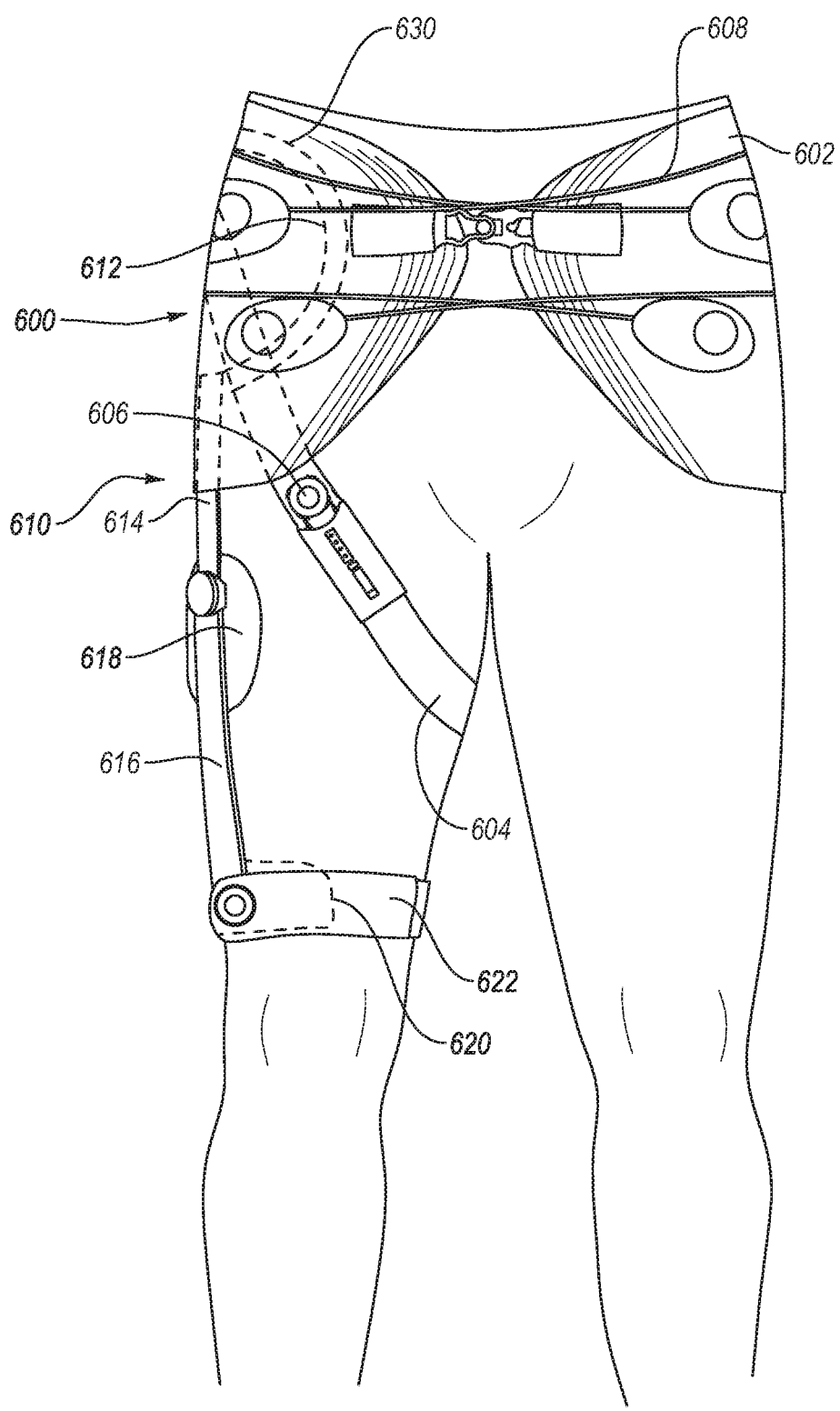
FIG. 36 is schematic view showing another embodiment of the orthopedic device.

Referring to the embodiment of FIG. 36, features of the embodiments described herein may be combined in an orthopedic device 600 arranged to aid in hip arthroscopy procedures by distracting the hip joint to allow entry of the arthroscope. The orthopedic device may serve to alleviate pain arising from indications such as femoral acetabular impingement.

The orthopedic device 600 includes a belt assembly 602 with tensioning device 608 that may be arranged similarly to the first and second belt members 202, 204, and tensioning devices 214 of the orthopedic device 200. The tensioning device 608 may be spread out so the upper tensioning devices adjust compression in the lumbar region while the lower tensioning devices apply pressure in the trochanter region. The lumbar compression system delivers active vertebral offloading and a better grip of patient's hips.

An exorotation strap 604 with a tensioning device 606 may likewise be provided similarly to the exorotation strap 217 and the tensioning device 220. The exorotation strap 604 may secure to a lower strap 622 that may be similar to the lower strap 226. Alternatively, the exorotation strap 604 may strap to the lower wrap with a buckle that enables the user to open the buckle for removal or loosening of the exorotation strap. A known buckle that may be used is described in U.S. Pat. No. 7,198,610, granted on Apr. 3, 2007, and incorporated herein by reference in its entirety.

The orthopedic device 600 is preferably without a garment, but rather it includes a hip orthosis 610. The hip orthosis is secured to the belt assembly 602 by appropriate means such as a pocket 630 or other fastener means such as hook and loop, and to the lower wrap 622. The hip orthosis may be arranged similarly to the hip orthosis described in U.S. application Ser. No. 13/528,032, filed on Jun. 20, 2012, and published as U.S. patent application publication 2012/0323154 A1 on Dec. 20, 2012, and incorporated herein in its entirety. The hip orthosis may employ the features in U.S. application Ser. No. 12/353,555, filed on Jan. 14, 2009 and published as U.S. patent application publication 2009/0124948 A1 on May 14, 2009, U.S. Pat. No. 8,172,779, granted on May 8, 2012, U.S. Pat. No. 7,597,672, granted on Oct. 6, 2009, and U.S. Pat. No. 7,198,610, granted on Apr. 3, 2007, incorporated herein by reference in their entirety.

Figure 37:
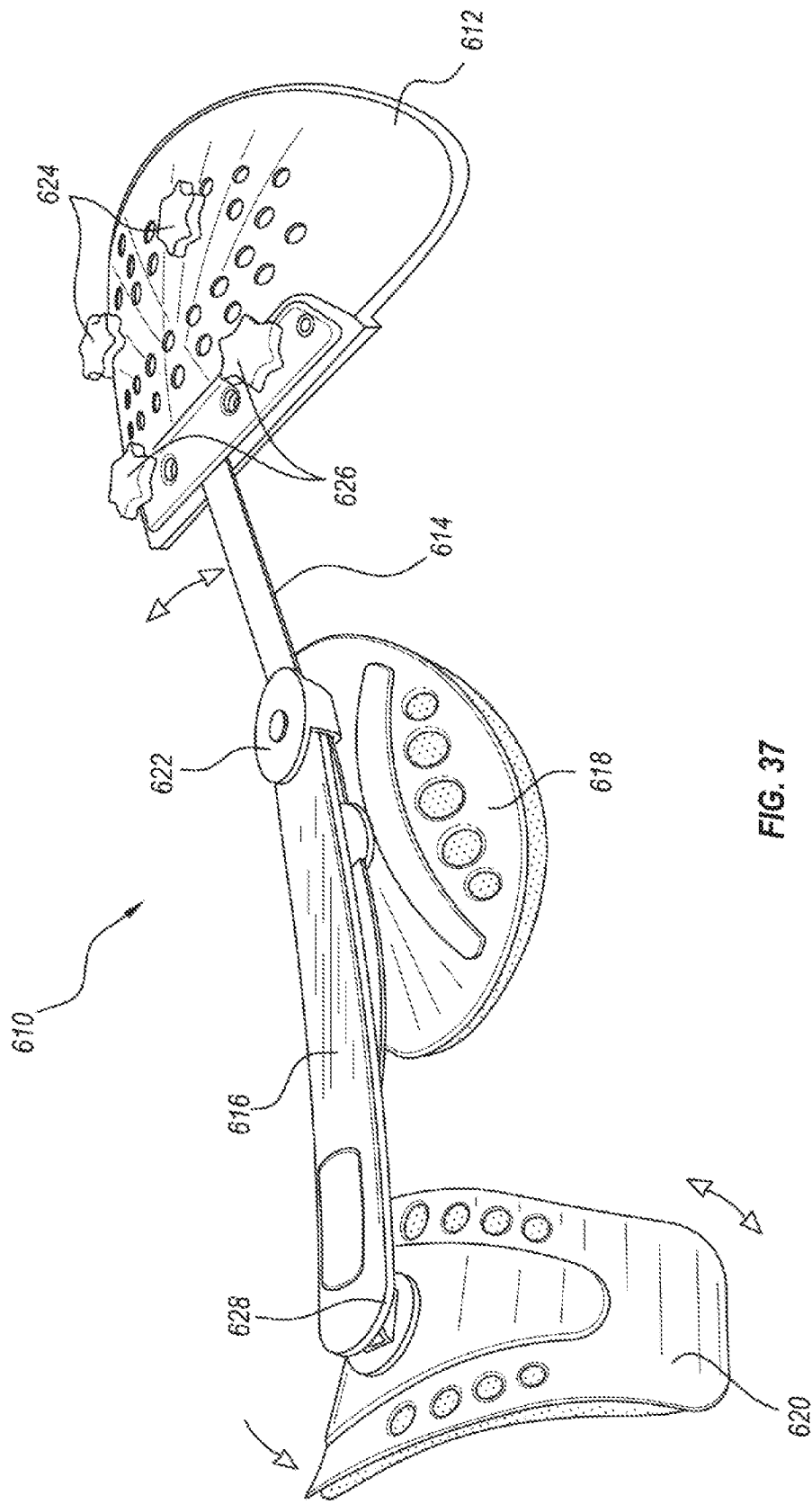
FIG. 37 is a perspective view showing a frame assembly in the orthopedic device of FIG. 36.

In referring to FIGS. 36 and 37 illustrate an embodiment of the hip orthosis 610, which incorporates some of the basic functions of the hip orthosis taught in part in U.S. Pat. No. 7,597,672. According to this embodiment, the hip orthosis 602 includes a hip plate 612 adapted to secure to the hip of the user and remain in place with the belt assembly 602. The orthosis includes a lower thigh cuff 620 adapted to secure to the thigh of the user and remain in place with the lower wrap 622.

A spring rod 614 connects the hip plate 612 and the lower thigh cuff 620 to one another. A lower spring rod support 616 and an upper spring rod support 622 engage the spring rod 614. A thigh pad or shell 618 slidably engages and is carried by the spring rod 614. The thigh pad or shell 618 may or may not be arranged to rotate relative to the thigh of a user. The spring rod 614 is pivotally connected to the lower thigh cuff 620 at pivot connection 628. The lower thigh cuff 620 may be arranged for height adjustment such that it can slide up and down relative to the spring rod 614 and snap in place among a plurality of predetermined locations.

As for the hip plate 612, the spring rod 614 has an end portion inserted within the hip plate 612, and slides side to side relative to the hip plate 612 with the motion restricted by restriction stops 626, and flexion and extension stops 624 limit movements of the hip plate 612 and the spring rod 614 relative to one another. The flexion and extensions stops 624 and the restriction stops 626 are adjustable on the hip plate 612.

The stops are preassembled for the right hip and range of motion of 0° extension to 70° flexion. If the hip orthosis is fitted for the left hip and the range of motion restriction is adjusted, the restriction stops and the flexion/extension stops can be placed in the correct location. Two restriction stops, one flexion stop and one extension stop, are arranged to restrict the range of motion. Guides may be provided on the inside and outside portions of the hip plate for reference, however the resultant flexion and extension angle should be verified to assure that the correct angle is set.

If the desired angle is between 0° and 70°, the restriction stops are placed in two inner openings (closest to the spring rod). If the desired angle is between 60° and 90°, the restriction stops are placed in two outer openings (farthest from the spring rod). The flexion/extension stops are placed according to indicia on the inside and/or the outside of the hip plate.

Figures 38, 39:
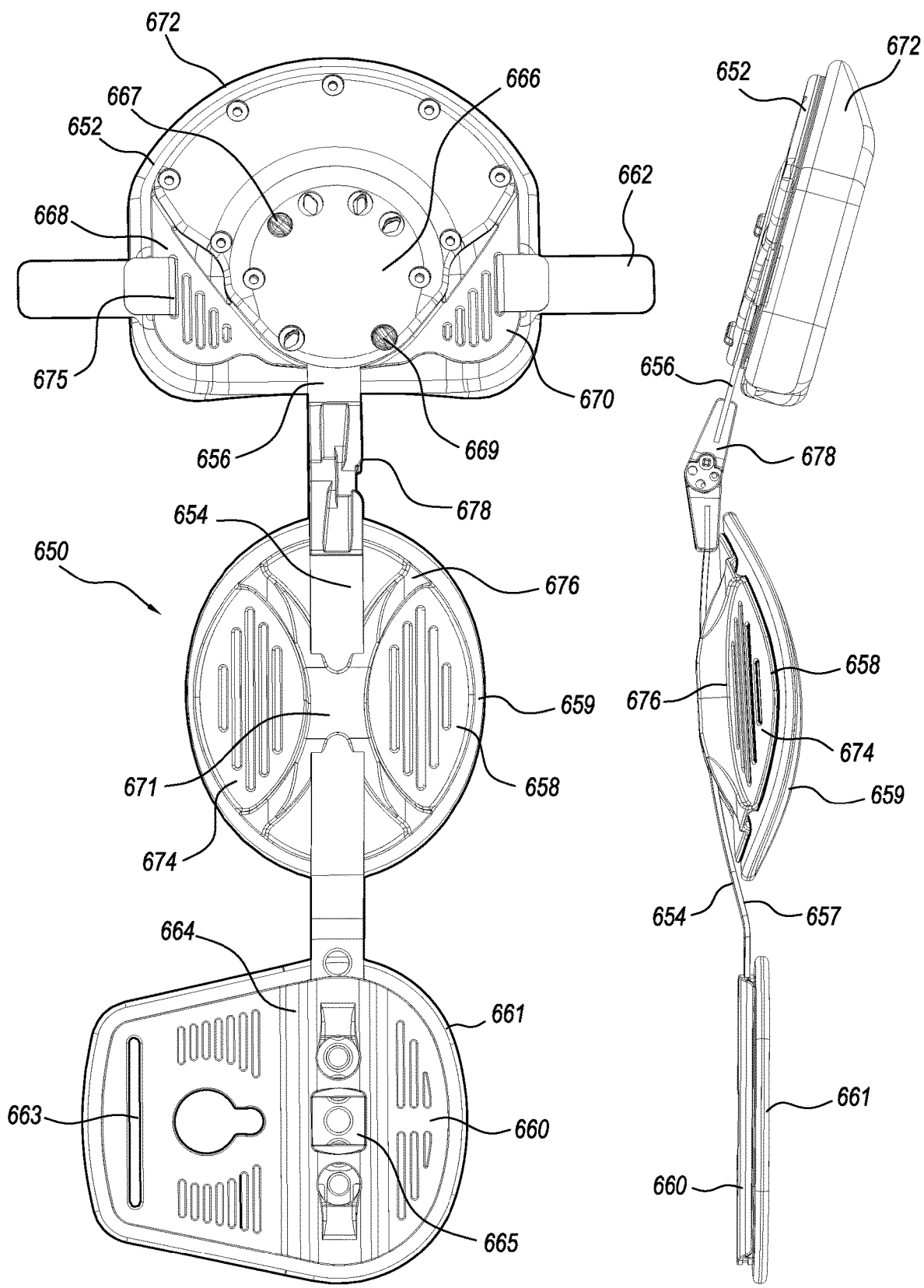
FIG. 38 is an elevational front view of another hip orthosis embodiment.
FIG. 39 is an elevational side view of the hip orthosis of FIG. 38.

FIGS. 38 and 39 disclose another hip orthosis or orthopedic device 650 arranged similarly in function as in FIGS. 27-37. According to this embodiment, the device includes a hip plate 652 with a pad 672, and a first strut 654 coupling at a hinge 678 to a second strut 656 received by the hip plate 652. At least the first strut 654 may define an anatomical curvature 657 along which an intermediate shell 658 carrying a pad 659 slidably engages. The curvature 657 assists in biasing the hip plate 652, the intermediate shell 658 and a thigh cuff 660 with a pad 661 inwardly toward the user. By reference to "inwardly," it is indicated the hip plate, intermediate shell and thigh cuff are directed or encouraged for movement in generally a same direction when the orthopedic device 650 is donned and secured to a user.

The first strut 654 is preferably longer than the second strut 656 in part due to the placement of the hinge 678 proximate the hip plate 652 and for permitting sliding of the intermediate shell 658. The second strut 656 is preferably straight and flat in contrast to the anatomical curvature 657 of the hip plate 652. The intermediate shell 658 is preferably received within an apex of the anatomical curvature 657 although it may be adjustable along the length of the first strut 654.

Figure 40:
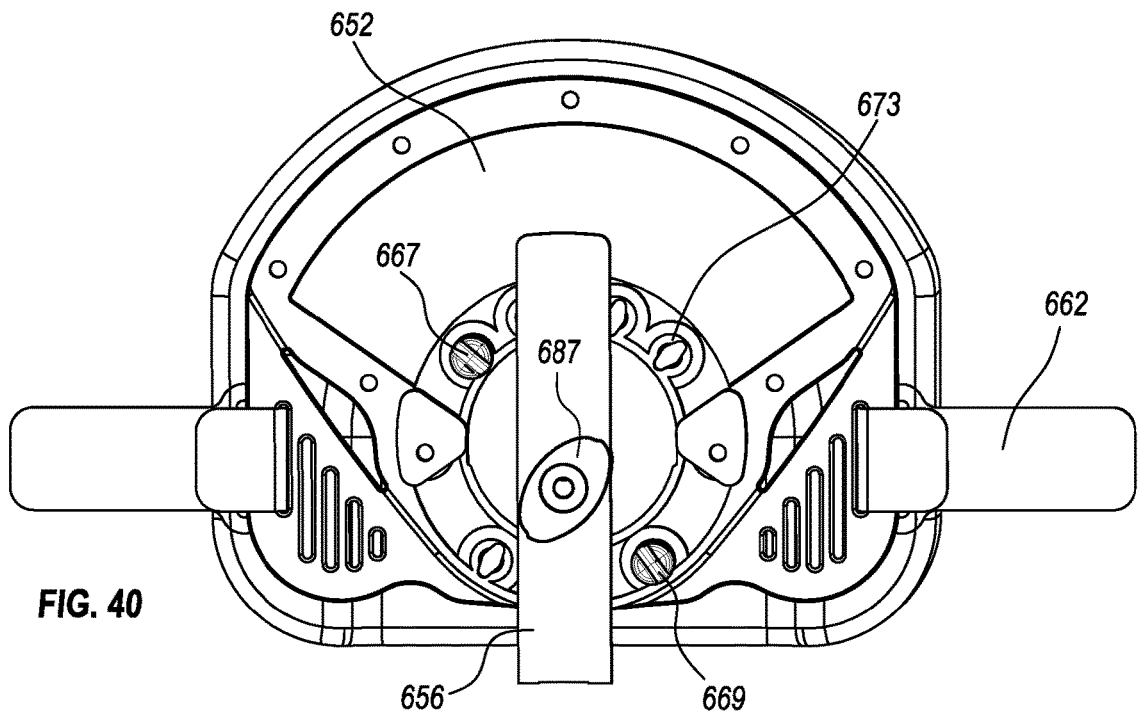
FIG. 40 is a schematic view of an upper frame of the hip orthosis of FIG. 38 without a cover plate.

Referring to FIG. 38, with the cover, and FIG. 40 without the cover, the hip plate 652 includes a cover 666 which encases a portion of the second strut 656 which slides within the hip plate between flexion and extension positions selectively delimited by range of motions stops 667, 669 to form a floating hinge. The range of motion stops can be secured into any of the flexion stop slots 673 among a plurality of settings, such as 0, 45 or 90 degrees. The range of motion stops can also be secured in any of the extension stop slots 669 which may be arranged at a variety of angles, which are shown as being close to 0 degrees. A sliding stop 687 may be attached to the second strut 656 to maintain the strut within a space defined between the hip plate 652 and the cover 666. The hip plate 652 includes a pair of slots 675 through which extend straps 662 arranged to secure to a strap or lumbar support or other suitable means for securing about the waist or hips of a user.

The various straps, wraps and tensioning devices may be trimmed to accommodate the various size profiles of users. Hook materials, buckles and other fastening devices may be removably secured to these various components to permit quick sizing changes. The straps may be oriented in different directions, such as the exorotation strap, to allow for modular placement of these straps to allow for extension or flexion control, and internal or external control. Various pads may be removably secured to frame elements, such as the trochanter pad that can have a cutout of inner foam for better fit and comfort around the trochanter.

The intermediate shell 658 defines a sleeve 671 along which the first strut 654 slidingly engages with a close fitting relationship to permit the user to adjust the location as needed but does not move or generally remains in place once positioned. The intermediate shell 658 includes rib portions 676 having an arcuate profile which delimit flexible portions 674 on opposed sides of the first strut 654. The rib portions 676 maintain rigidity of the intermediate shell 658 while permitting the flexible portions 674 to anatomically bend about the anatomy of a user according to the arcuate profile of the rib portions 676.

The thigh cuff 660 may include a slot 663 permitting insertion of a strap, as discussed in connection with FIG. 35 and strap 550. The thigh cuff 660 defines a plurality of living hinges 664 enabling the thigh cuff 660 to better contour to the leg of a user. The thigh cuff 660 may include a height adjustment or telescoping mechanism 665 corresponding similarly to other embodiments mentioned herein.

Figure 41:
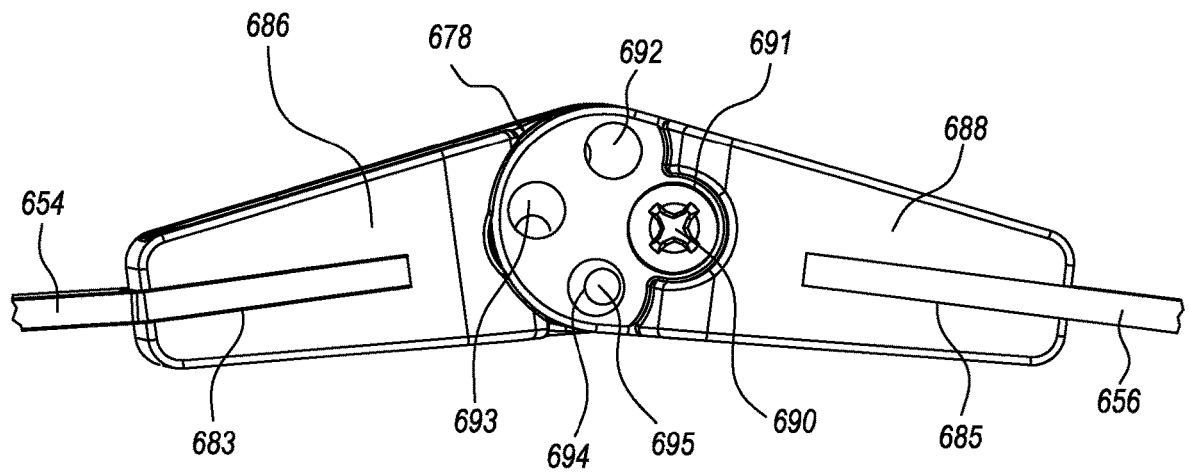
FIG. 41 is a schematic plan view of the hinge in the hip orthosis of FIG. 38.
Figure 42:
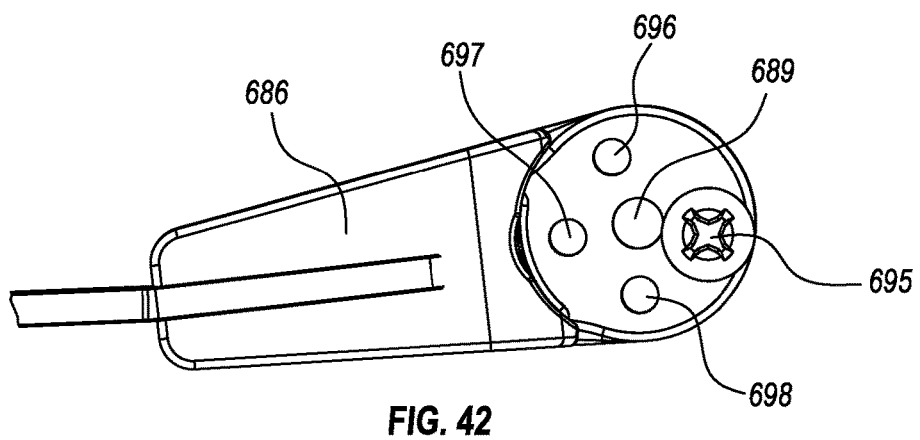
FIG. 42 is a schematic partial view of the hinge in FIG. 41.

Referring to FIGS. 41 and 42, the hinge 678 is arranged to provide adjustable abduction ranging from a plurality of angles. For example, the hinge 678 permits adjustable abduction ranging from 0-30 degrees with indications at 0, 10, 20 and 30 degrees. The hinge 678 includes first and second parts 686, 688 which rotate about pivot point 689. The degree settings are obtained by selectively mating of one of holes 691, 692, 693, 694 defined by the first part 686 with a corresponding one of holes 695, 696, 697, 698 of the second part 686. A fastener 690 is arranged to engage the first and second parts 686, 688 at the corresponding holes, such as in FIG. 41 which shows the hinge at a 10 degree abduction setting. The first and second hinge parts 686, 688 define slots 683, 685 into which the first and second struts 654, 655 secure.

Figure 43:
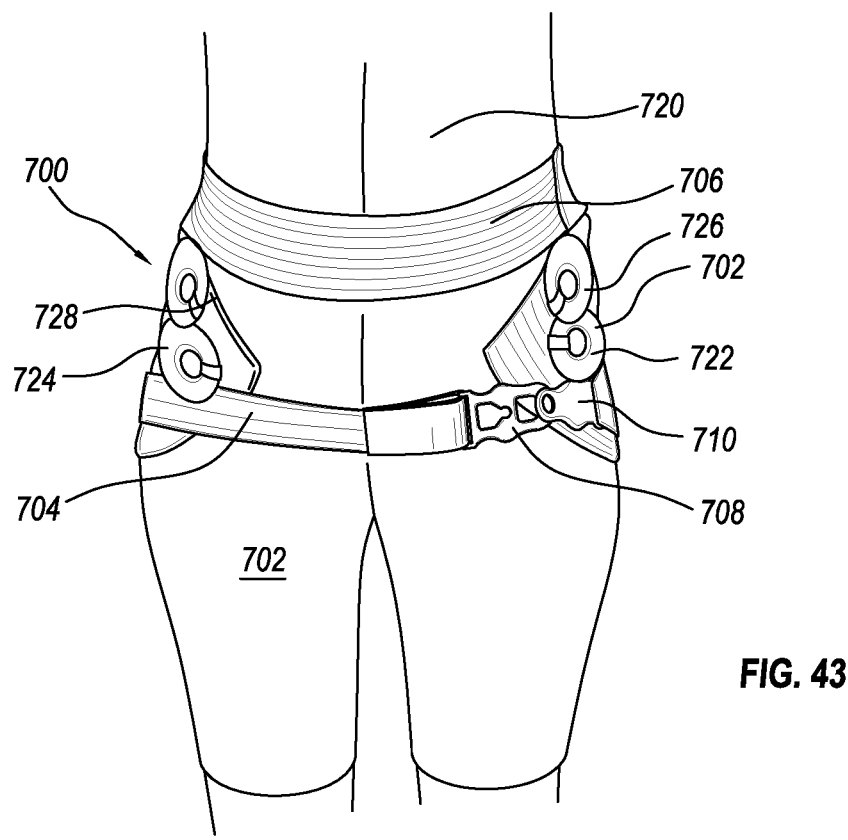
FIG. 43 is a schematic front view of another embodiment of a hip orthosis for maternity use.
Figure 44:
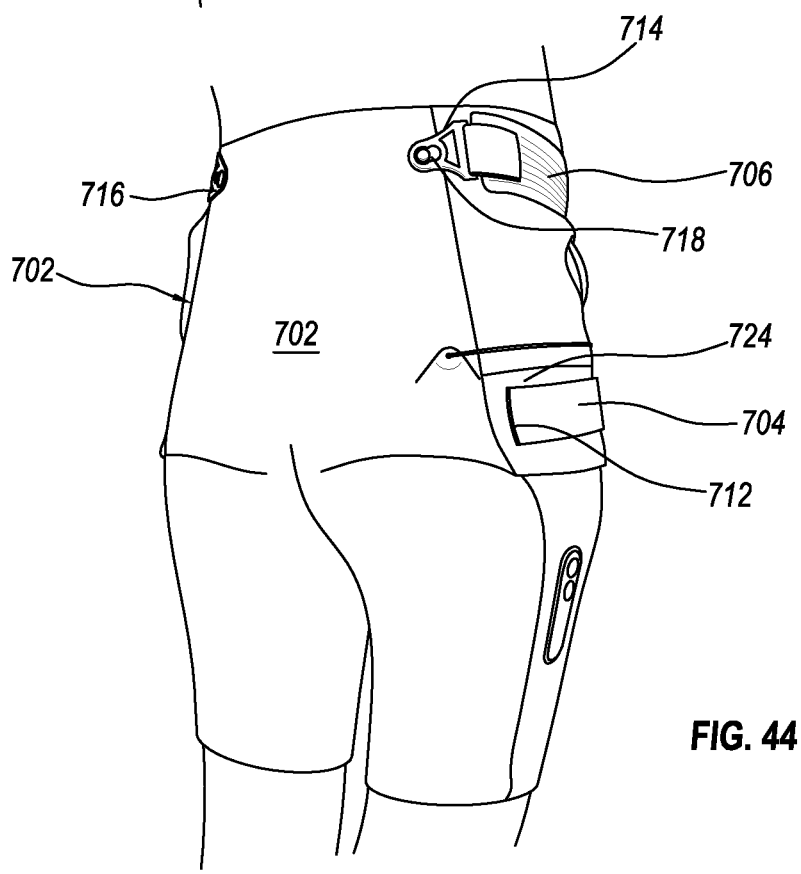
FIG. 44 is a schematic rear view of the hip orthosis of FIG. 43.

FIGS. 43 and 44 depict a hip orthosis 700 converted for maternity use. The hip orthosis 700 includes a garment 702 and first and second belt members 722, 724, similar to any of the aforementioned embodiments including the embodiment of FIG. 11.

A lower strap 704 is arranged to secure over and connect to the first and second belt members 722, 724 to preferably sit just above the symphysis pubis joint. The lower strap 704 may be anchored at the end of the first and second belt members 722, 724 at a location 712 where the belt members secure to the garment 702. The lower strap is preferably but not limited to being inelastic.

To create compression, the handles of the tensioning devices 726, 728 of a compression unit, according to any of the aforementioned embodiments, are arranged to be pulled to create compression around the pelvis. The compression generated by the compression unit is generally focused on the sacroiliac joints in the back (posterior) and the symphysis joint in the front (anterior). As with other embodiments described herein, compression is likewise generated over the greater trochanter.

To each application and sizing of the lower strap 704, opposed first and second segments of the lower strap include first and second buckles 708, 710, similar to the embodiment of FIG. 15A. Other suitable means for securing opposed ends of the first and second segments of the lower strap 704, and permitting adjustment may be used, as discussed above.

An upper strap 706 may be used so the user can place the strap under the belly to transfer some of the weight to the user's back. The upper strap 706 may be elastic to accommodate movement of the belly and ease in comfort. The upper strap 706 is preferably secured to the posterior region or sides of the garment at pins 718 upon which catches 714, 716 at end portions of the upper strap 706 removably engage. The catches permit selective use of the upper strap 706. The upper strap 706 is preferably mounted above the compression system at the posterior of the hip orthosis, at locations in which the compression system is described in aforementioned embodiments.

The garment of the hip orthosis 700 may be constructed according to any of the aforementioned embodiments, but the hip orthosis 700 may be modified as follows. The garment 702 may be modified to include supplemental material 720 to accommodate sizing of a belly, particularly during maternity phases.

Figure 45:
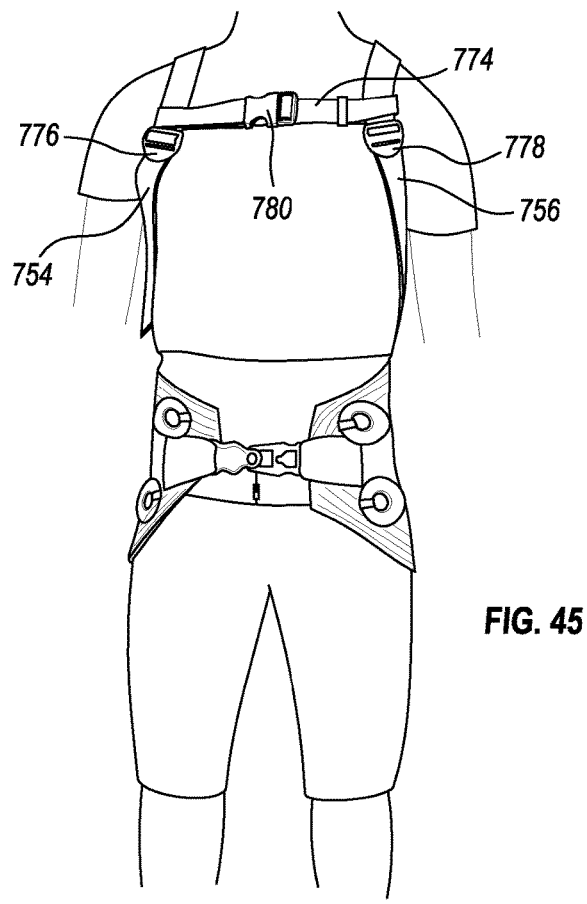
FIG. 45 is a schematic front view of another embodiment of a hip orthosis for treating spinal stenosis.
Figure 47:
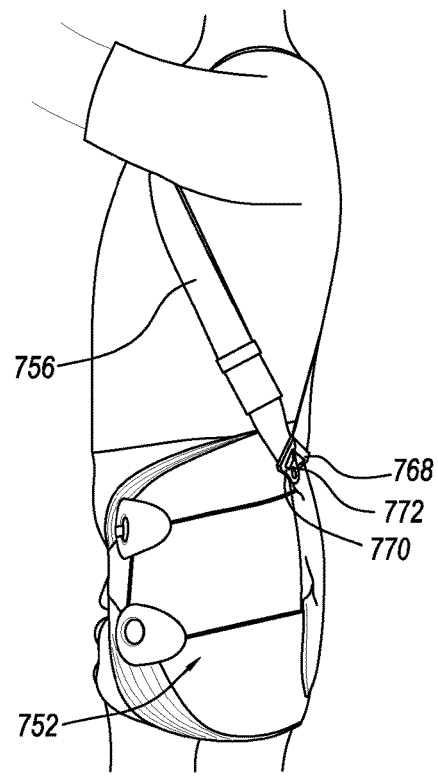
FIG. 47 is a schematic side view of the embodiment of FIG. 45.
Figure 46:
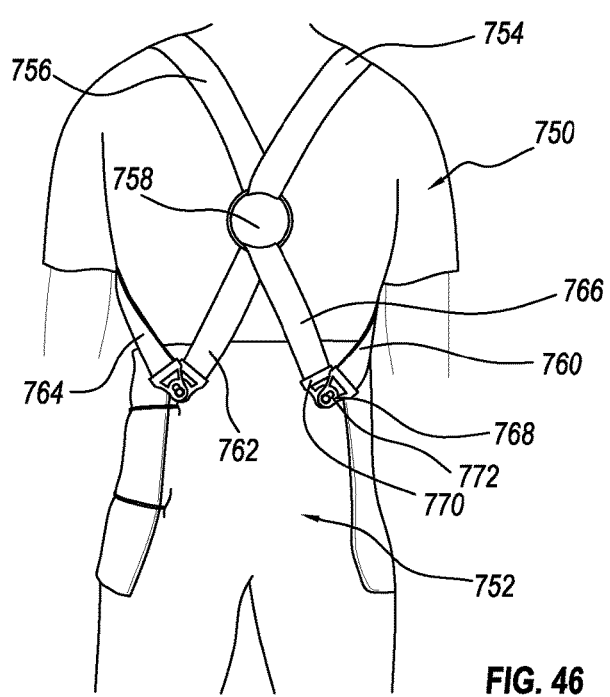
FIG. 46 is a schematic rear view of the embodiment of FIG. 45.

FIGS. 45-47 depict another modification to any of the hip orthosis 752 embodiments described above to include a spinal stenosis kit 750. The spinal stenosis kit is arranged to treat the condition when the femurs of a user are externally rotated, the pelvis will tilt forward slightly creating a "shopping trolley" posture. People suffering from spinal stenosis often report they can walk all day while pushing a shopping trolley but struggle to walk back to a car afterwards. By creating some flexion in the lower lumbar area, the spinal canal is opened thereby reducing pressure on the spinal and spinal nerves. The spinal stenosis kit provides a harness that allows the user to flex the back into the harness and from that position create the same or similar posture as pushing the shopping trolley.

The spinal stenosis 750 includes first and second straps 754, 756 having first and second ends that secure to the posterior region or sides of the hip orthosis, and a guide 758 that retains the first and second straps 754, 756 to one another on the posterior side over a user's back. For example, the first strap 754 has a first end 760 attached to the posterior region on a first side of the hip orthosis and a second end 762 attached to the posterior region on a second side of the orthosis. The first and second ends of the second strap 756 are similarly arranged. It is preferred that the first and second ends of the straps secure to the posterior region of the hip orthosis to pull the user's back rearward. The strap ends have buckles 768, 770 preferably removably securing to a pin 772 on the compression system or garment to enable selective use of the spinal stenosis kit 750.

The anterior side of the spinal stenosis is arranged to include a sternum strap 774 extending between the first and second straps 754, 756 as they loop over the user's shoulder. The sternum strap enables better distribution of pressure exerted by the straps, and have opposed ends that connect at a buckle 780. The first and second straps 754, 756 have adjustment buckles 776, 778 for adjusting pressure and length of the first and second straps 754, 756.

The embodiments of the orthopedic device described above in accordance with present disclosure at provide solutions to reduce pain, speed healing processes, and impart improved stability and mobility of the hip, knee and associated pelvic, lumbar and lower leg indications. The orthopedic device is lightweight and has a streamlined profile that is simple to use for wearers of various age groups. The orthopedic device permits more precise adjustment and enables efficient coordination between a medical professional and the wearer on the degree the orthopedic device should be configured. Patient comfort is also enhanced and donning and doffing of the orthopedic device is eased with the novel features described.

It is to be understood that not necessarily all such objects or advantages may be achieved under any embodiment of the disclosure. For example, those skilled in the art will recognize that the orthopedic device may be embodied or carried out in a manner that achieves or optimizes one advantage or group of advantages as taught without achieving other objects or advantages as taught or suggested.

The skilled artisan will recognize the interchangeability of various features from different embodiments. Besides the variations described, other known equivalents for each feature can be mixed and matched by one of ordinary skill in this art to construct a an orthopedic device under principles of the present disclosure.

Although the orthopedic device has been disclosed in certain preferred embodiments and examples, it therefore will be understood by those skilled in the art that the present invention extends beyond the specifically disclosed embodiments to other alternative embodiments and/or uses of the orthopedic device and obvious modifications and equivalents thereof. It is intended that the present disclosure should not be limited by the particular disclosed embodiments described above, but should be determined only by a fair reading of the claims that follow.

The invention claimed is:

1. A hip orthosis, comprising:
a garment adapted to secure about a user's hip, the garment including a main body configured to extend over thighs and hips of the user, a waist band located at an uppermost portion of the main body, and first and second lower bands located at a lowermost portion of the main body and corresponding to first and second thigh portions of the main body;
an exorotation strap having a first end securing to the garment and a second end securing to a wrap adapted to secure about one of the user's legs, the exorotation strap spiraling between the garment and the wrap, the wrap extending over the first thigh portion of the garment and proximate to the first lower band;
first and second belt members having first ends each joined by permanent stitching to opposed first and second posterior sides of the garment at first and second joints, respectively, the first ends of the first and second belt members at the first and second joints being spaced apart by a clearance and separated by a midline of the garment adapted to correspond to a midsagittal plane of the user, and the first and second belt members extending freely from the first and second joints such that second ends of the first and second belt members are arranged to connect on an anterior side of the garment, the first and second belt members located proximate the waist band, the exorotation strap extending underneath the first belt member, the first and second belt members each being arranged to wrap about the user's right and left hips including the trochanters of such right and left hips;
wherein at least one of the first and second belt members defines a slit at a posterior side thereof and through which the first end of the exorotation strap extends, such that a tab at the first end of the exorotation strap secures to an anchor on the respective first or second posterior side of the garment adjacent the respective stitched first or second joint.

2. The hip orthosis of claim 1, further comprising a trochanter pad securable along an inner surface of the first belt member.

3. The hip orthosis of claim 1, wherein the exorotation strap is detachable from the wrap.

4. The hip orthosis of claim 1, wherein the exorotation strap extends along its entirety over the garment.

5. The hip orthosis of claim 1, wherein the wrap includes a first segment that is elastic, a second segment that secures to an end of the first segment and a third segment secured to another end of the first segment, the second and third segments are generally inelastic.

6. The hip orthosis of claim 1, wherein the second end of the exorotation strap secures to an inner surface of the wrap.

7. A hip orthosis, comprising:
a garment adapted to secure about a user's hip;
an exorotation strap having a first end securing to the garment and a second end securing to a wrap adapted to secure about one of the user's legs, the exorotation strap spiraling between the garment and the wrap;
first and second belt members having first ends each joined by permanent stitching to opposed first and second posterior sides of the garment at first and second joints, respectively, the first ends of the first and second belt members at the first and second joints being spaced apart by a clearance and separated by a midline of the garment adapted to correspond to a midsagittal plane of the user, and the first and second belt members extending freely from the first and second joints such that second ends of the first and second belt members are arranged to connect on an anterior side of the garment, the first and second belt members located proximate a waist band, the exorotation strap extending underneath the first belt member, the first and second belt members each being arranged to wrap about the user's right and left hips including the trochanters of such right and left hips;
wherein the exorotation strap includes a first segment depending from the garment, and a second segment coupled to the first segment;
wherein the first belt member extends over at least a segment of the exorotation strap;
wherein at least one of the first and second belt members defines a slit at a posterior side thereof and through which the first end of the exorotation strap extends, such that a tab at the first end of the exorotation strap secures to an anchor on the respective first or second posterior side of the garment adjacent the respective stitched first or second joint.

8. A hip orthosis, comprising:
a garment adapted to secure about a user's hip;
an exorotation strap having a first end securing to the garment and a second end securing to a wrap adapted to secure about one of the user's legs, the exorotation strap spiraling between the garment and the wrap;
first and second belt members having first ends each joined by permanent stitching to opposed first and second posterior sides of the garment at first and second joints, respectively, the first ends of the first and second belt members at the first and second joints being spaced apart by a clearance and separated by a midline of the garment adapted to correspond to a midsagittal plane of the user, and the first and second belt members extending freely from the first and second joints such that second ends of the first and second belt members are arranged to connect on an anterior side of the garment, the first and second belt members located proximate a waist band, the exorotation strap extending underneath the first belt member, the first and second belt members each being arranged to wrap about the user's right and left hips including the trochanters of such right and left hips;
a compression system at a posterior of the garment located within the clearance between first ends of the first and second belt members, a first tensioning device corresponding to the first belt member, and a second tensioning device corresponding to the second belt member, the first and second tensioning devices extending freely from the compression system for attachment to the first and second belt members, and the first and second tensioning devices arranged for tensioning the compression system over a pelvis of the user;

wherein the first tensioning device extends over the first belt member;

wherein at least one of the first and second belt members defines a slit at a posterior side thereof and through which the first end of the exorotation strap extends, such that a tab at the first end of the exorotation strap secures to an anchor on the respective first or second posterior side of the garment adjacent the respective stitched first or second joint.

\* \* \* \* \*